US008435513B2

(12) United States Patent
Gurney et al.

(10) Patent No.: US 8,435,513 B2
(45) Date of Patent: May 7, 2013

(54) NOTCH1 RECEPTOR ANTIBODIES AND METHODS OF TREATMENT

(75) Inventors: Austin L. Gurney, San Francisco, CA (US); Timothy Hoey, Hillsborough, CA (US); Maureen Fitch Bruhns, San Mateo, CA (US); Fumiko Takada Axelrod, Palo Alto, CA (US)

(73) Assignee: OncoMed Pharmaceuticals, Inc., Redwood City, CA (US)

( * ) Notice: Subject to any disclaimer, the term of this patent is extended or adjusted under 35 U.S.C. 154(b) by 176 days.

(21) Appl. No.: 13/003,013

(22) PCT Filed: Jul. 8, 2009

(86) PCT No.: PCT/US2009/003995
§ 371 (c)(1),
(2), (4) Date: Apr. 7, 2011

(87) PCT Pub. No.: WO2010/005567
PCT Pub. Date: Jan. 14, 2010

(65) Prior Publication Data
US 2011/0311552 A1    Dec. 22, 2011

Related U.S. Application Data

(60) Provisional application No. 61/079,095, filed on Jul. 8, 2008, provisional application No. 61/112,699, filed on Nov. 7, 2008, provisional application No. 61/112,701, filed on Nov. 7, 2008.

(51) Int. Cl.
*A61K 39/395* (2006.01)
*C07K 16/00* (2006.01)
*C07K 16/18* (2006.01)
*C07K 16/28* (2006.01)
*C07H 21/04* (2006.01)
*C12N 5/00* (2006.01)
*C12N 5/10* (2006.01)

(52) U.S. Cl.
USPC .................. 424/130.1; 424/133.1; 424/135.1; 424/136.1; 424/141.1; 424/143.1; 435/325; 435/326; 435/328; 435/334; 514/19.2; 514/19.3; 514/19.4; 514/19.5; 530/387.1; 530/387.3; 530/388.1; 530/388.22; 530/389.1; 536/23.1; 536/23.5

(58) Field of Classification Search .................. None
See application file for complete search history.

(56) References Cited

U.S. PATENT DOCUMENTS

| | | | |
|---|---|---|---|
| 5,648,464 A | 7/1997 | Artavanis-Tsakonas et al. |
| 5,786,158 A | 7/1998 | Artavanis-Tsakonas et al. |
| 5,789,195 A | 8/1998 | Artavanis-Tsakonas et al. |
| 5,854,027 A | 12/1998 | Steipe et al. |
| 6,004,528 A | 12/1999 | Bergstein |
| 6,080,588 A | 6/2000 | Glick |
| 6,083,904 A | 7/2000 | Artavanis-Tsakonas |
| 6,090,922 A | 7/2000 | Artavanis-Tsakonas et al. |
| 6,180,370 B1 | 1/2001 | Queen et al. |
| 6,379,925 B1 | 4/2002 | Kitajewski et al. |
| 6,537,775 B1 | 3/2003 | Tournier-Lasserve et al. |
| 6,689,744 B2 | 2/2004 | Gao et al. |
| 6,692,919 B1 | 2/2004 | Artavanis-Tsakonas et al. |
| 6,984,522 B2 | 1/2006 | Clark et al. |
| 7,091,323 B2 | 8/2006 | Pan et al. |
| 7,115,360 B2 | 10/2006 | Clarke et al. |
| 7,282,203 B2 | 10/2007 | Coignet |
| 7,432,364 B2 | 10/2008 | Pan et al. |
| 7,632,926 B2 | 12/2009 | Kim et al. |
| 7,713,710 B2 | 5/2010 | Clarke et al. |
| 7,754,206 B2 | 7/2010 | Clarke et al. |
| 7,850,961 B2 | 12/2010 | Clarke et al. |
| 7,919,092 B2 | 4/2011 | Lewicki et al. |
| 8,088,617 B2 | 1/2012 | Gurney et al. |
| 8,206,713 B2 | 6/2012 | Lewicki et al. |
| 2002/0086014 A1 | 7/2002 | Korman et al. |
| 2002/0119565 A1 | 8/2002 | Clarke et al. |
| 2002/0122802 A1 | 9/2002 | Wands et al. |
| 2003/0082651 A1 | 5/2003 | Gao et al. |
| 2003/0083465 A1 | 5/2003 | Zimrin et al. |
| 2003/0186290 A1 | 10/2003 | Tournier-Lasserve et al. |

(Continued)

FOREIGN PATENT DOCUMENTS

DE    44 25 115 A1    1/1996
EP    0 662 827 B2    7/1995

(Continued)

OTHER PUBLICATIONS

Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Rudikoff et al, 1982 (Proc Natl Acad Sci USA. vol. 79: 1979-1983).*
MacCallum et al (1996. J Mol Biol. 262: 732-745).*
de Pascalis et al (2002. The Journal of Immunology. 169: 3076-3084).*
Casset et al (2003. Biochemical and Biophysical Research Communications. 307: 198-205).*
Vajdos et al (2002. J Mol Biol. 320: 415-428).*
Holm et al (2007. Mol Immunology. 44: 1075-1084).*
Chen et al (1999. J Mol Biol. 293: 865-881).*
Wu et al (1999. J Mol Biol. 294: 151-162).*
Paul, W.E. Fundamental Immunology, 3rd Edition, Raven Press, New York, Chapt. 8, pp. 292-295 (1993).*
Al-Hajj et al., "Prospective Identification of Tumorigenic Breast Cancer Cells," Cell Biology 100:3983-3988 (2003), Proceedings of the National Academy of Science, 700 11th Street, NW Suite 450 Washington, DC 20001.

(Continued)

*Primary Examiner* — Bridget E Bunner
(74) *Attorney, Agent, or Firm* — Sterne Kessler Goldstein & Fox P.L.L.C.

(57) ABSTRACT

The present invention relates to compositions and methods for characterizing, diagnosing, and treating cancer. In particular the invention provides the means and methods for the diagnosis, characterization, prognosis and treatment of cancer and specifically targeting cancer stem cells. The present invention provides an antibody that specifically binds to a non-ligand binding membrane proximal region of the extracellular domain of a human Notch receptor and inhibits tumor growth. The present invention further provides a method of treating cancer, the method comprising administering a therapeutically effective amount of an antibody that specifically binds to a non-ligand binding membrane proximal region of the extracellular domain of a human Notch receptor protein and inhibits tumor growth.

22 Claims, 7 Drawing Sheets

U.S. PATENT DOCUMENTS

| | | | |
|---|---|---|---|
| 2004/0229301 | A1 | 11/2004 | Wang |
| 2005/0026831 | A1 | 2/2005 | Bodmer et al. |
| 2005/0089518 | A1 | 4/2005 | Clarke et al. |
| 2005/0112121 | A1 | 5/2005 | Artavanis-Tsakonas et al. |
| 2005/0142635 | A1 | 6/2005 | Tsuchiya et al. |
| 2005/0187179 | A1 | 8/2005 | Miele et al. |
| 2005/0232927 | A1 | 10/2005 | Clarke et al. |
| 2006/0030694 | A1 | 2/2006 | Kitajewski et al. |
| 2006/0051325 | A1 | 3/2006 | Clarke et al. |
| 2006/0073125 | A1 | 4/2006 | Clarke et al. |
| 2006/0083682 | A1 | 4/2006 | Bergstein |
| 2006/0263774 | A1 | 11/2006 | Clark et al. |
| 2007/0036800 | A1 | 2/2007 | Bergstein |
| 2007/0036801 | A1 | 2/2007 | Bergstein |
| 2007/0036804 | A1 | 2/2007 | Bergstein |
| 2007/0041984 | A1 | 2/2007 | Bergstein |
| 2007/0196047 | A9 | 8/2007 | Levner et al. |
| 2007/0212737 | A1 | 9/2007 | Clarke et al. |
| 2007/0265246 | A1 | 11/2007 | Clevers et al. |
| 2008/0076670 | A1 | 3/2008 | Sivan et al. |
| 2008/0112940 | A1 | 5/2008 | Liaw |
| 2008/0118520 | A1 | 5/2008 | Li et al. |
| 2008/0131434 | A1 | 6/2008 | Lewicki et al. |
| 2008/0131908 | A1 | 6/2008 | Li et al. |
| 2008/0132423 | A1 | 6/2008 | Kondo |
| 2008/0178305 | A1 | 7/2008 | Clarke et al. |
| 2008/0187532 | A1 | 8/2008 | Gurney et al. |
| 2008/0188405 | A1 | 8/2008 | Di Fiore et al. |
| 2008/0194022 | A1 | 8/2008 | Clarke et al. |
| 2008/0226621 | A1 | 9/2008 | Fung et al. |
| 2008/0260734 | A1 | 10/2008 | Clarke et al. |
| 2009/0004205 | A1 | 1/2009 | Clarke et al. |
| 2009/0028856 | A1 | 1/2009 | Chen et al. |
| 2009/0047285 | A1 | 2/2009 | Gurney et al. |
| 2009/0081238 | A1* | 3/2009 | Siebel et al. ............ 424/172.1 |
| 2009/0208491 | A1 | 8/2009 | Gurney et al. |
| 2010/0111958 | A1 | 5/2010 | Gurney et al. |
| 2011/0033481 | A1 | 2/2011 | Clarke et al. |
| 2011/0092378 | A1 | 4/2011 | Clarke et al. |
| 2011/0195065 | A1 | 8/2011 | Lewicki et al. |
| 2011/0311552 | A1 | 12/2011 | Gurney et al. |
| 2012/0308558 | A1 | 12/2012 | Gurney et al. |

FOREIGN PATENT DOCUMENTS

| | | |
|---|---|---|
| JP | 2002-526109 A | 8/2002 |
| WO | WO 94/07474 A1 | 4/1994 |
| WO | WO 97/37004 A1 | 10/1997 |
| WO | WO 97/45143 A1 | 12/1997 |
| WO | WO 98/57621 A1 | 12/1998 |
| WO | WO 00/20576 A2 | 4/2000 |
| WO | WO 00/52143 A2 | 9/2000 |
| WO | WO 02/00576 | 1/2002 |
| WO | WO 02/12447 A2 | 2/2002 |
| WO | WO 02/18544 A | 3/2002 |
| WO | WO 03/042246 A2 | 5/2003 |
| WO | WO 03/050502 A | 6/2003 |
| WO | WO 03/062273 A2 | 7/2003 |
| WO | WO 2004/001004 A2 | 12/2003 |
| WO | WO 2004/052389 A2 | 6/2004 |
| WO | WO 2004/091383 A2 | 10/2004 |
| WO | WO 2004/094475 A2 | 11/2004 |
| WO | WO 2005/026334 A2 | 3/2005 |
| WO | WO 2005/054434 A2 | 6/2005 |
| WO | WO 2005/074633 A2 | 8/2005 |
| WO | WO 2006/110581 A2 | 10/2006 |
| WO | WO 2007/145840 A2 | 12/2007 |
| WO | WO 2008/051797 A3 | 5/2008 |
| WO | WO 2008/057144 A2 | 5/2008 |
| WO | WO 2008/076960 A2 | 6/2008 |
| WO | WO 2008/091641 A2 | 7/2008 |
| WO | WO 2008/108910 A2 | 9/2008 |
| WO | WO 2008/136848 A2 | 11/2008 |
| WO | WO-2008150525 A1 * | 12/2008 |
| WO | WO 2009/025867 A2 | 2/2009 |
| WO | WO 2009/035522 A1 | 3/2009 |
| WO | WO 2010/005567 A2 | 1/2010 |

OTHER PUBLICATIONS

Arias et al., "Csl-Independent Notch Signalling: A Checkpoint in Ceu Fate Decisions During Development?," Current Opinion In Genetics & Development, 12:524-533 (2002), Elsevier Science Ltd, The Boulevard, Langford Lane, Kidlington, Oxford, OX5 1 GB, UK.

Artavanis-Tsakonas et al., "Notch Signaling: Cell Fate Control and Signal Integration in Development," Science 284:770-776 (1999), American Association for the Advancement of Science, 1200 New York Avenue, NW, Washington, DC 20005.

Brennan and Brown, "Is There a Role for Notch Signalling in Human Breast Cancer?," Breast Cancer Research, 5:69-75 (2003), BioMed Central Ltd, London WC1X 8HL, United Kingdom.

Brennan et al., "Repression by Notch is Required Before Wingless Signalling During Muscle Progenitor Cell Development in *Drosophila*," Current Biology, 9:707-710 (1991), Current Biology Publications, 34-42 Cleveland Street, London W1 P GLE, UK.

Cole et al., "The Ebv-Hybridoma Technique and its Application to Human Lung Cancer," Monoclonal Antibodies and Cancer Therapy, 77-96 (1985), Alan R. Liss, Inc, 41 East 11th Street, New York, NY 10003.

Del Amo et al., "Cloning, Analysis, and Chromosomal Localization of Notch-1, a Mouse Homolog of *Drospohila* Notch," Genomics, 15:259-264 (1993), Academic Press, Inc.

Domenga et al., "Notch3 is required for arterial identity and maturation of vascular smooth muscle cells," Genes & Development, 18:2730-2735 (2004), Cold Spring Harbor Laboratory Press.

Duncan et al., "Integration of Notch and Wnt Signaling in Hematopoietic Stem Cell Maintenance," Nature Immunology 6:314-322 (2005), Nature Publishing Group, 345 Park Avenue South, New York, NY 10010-1707.

Ellisen et al., "Tan-1, The Human Homolog of the *Drosophila* Notch Gene, Is Broken by Chromosomal Translocations in T Lymphoblastic Neoplasms," Cell, 66:649-661 (1991), Cell Press, 50 Church Street, Cambridge, Massachusetts 02138.

Gale et al., "Haploinsufficiency of Delta-Like 4 Ligand Results in Embryonic Lethality Due to Major Defects in Arterial and Vascular Development," PNAS, 101:15949-15954 (2004), National Academy of Science, 700 11th Street, NW Suite 450 Washington, DC 20001.

Gallahan et al., "Expression of a Truncated Int3 Gene in Developing Secretory Mammary Epithelium Specifically Retards Lobular Differentiation Resulting in Tumorigenesis," Cancer Research, 56:1775-1785 (1996), American Association for Cancer Research, Inc, Public Ledger Bldg., Suite 816, 150 South Independence Mall West, Philadelphia, PA 19106-3483.

Gridley, T., "Notch signaling and inherited disease syndromes," Human Molecular Genetics 12:R9-R13 (2003), Oxford University Press.

Gridley, T., "Notch signaling during vascular development," PNAS, 98:5377-5378 (2001), National Academy of Sciences, Washington, DC 20001.

Gridley, T., "Vessel guidance," Nature, 445:722-723 (2007) Nature Publishing Group, New York, NY 10013-1917, USA.

Gridley, T., "Notch Signaling in Vertebrate Development and Disease," Mol. Cell. Neurosci, 9:103-108, (1997), Academic Press, 6377 Sea Harbor Drive, Orlando, FL 32887-4900.

Hadland et al., "A requirement for Notch1 distinguishes 2 phases of definitive hematopoiesis during development," Blood, 104:3097-3105 (2004), The American Society of Hematology.

Hainaud et al., "The Role of the Vascular Endothelial Growth Factor-Delta-like 4 Ligand/Notch4-Ephrin B2 Cascade in Tumor Vessel Remodeling and Endothelial Cell Functions," Cancer Res, 66:8501-8510, (2006), American Association for Cancer Research.

Hallahan et al., "The SmoA1 Mouse Model Reveals that Notch Signaling is Critical for the Growth and Survival of Sonic Hedgehog-Induced Medulloblastomas," Cancer Research, 64:7794-7800 (2004), American Association for Cancer Research, Philadelphia, PA 19106-4404.

Hitoshi et al., "Notch Pathway Molecules are Essential for Tile Maintenance, but not the Generation of Mammalian Neural Stem Cells," Genes & Development, 16:846-858 (2002), Cold Spring Harbor Laboratory Press, Cold Spring Harbor Laboratory Press 500 Sunnyside Boulevard Woodbury, New York 11797.

Iso et al., "Notch Signaling in Vascular Development," Arterioscler Thrombosis and Vascular Biology, 23:543-553 (2003), Lippincott Williams & Wilkins, Philadelphia, PA 19106.

Jhappan et al., "Expression of an Activated Notch-Related Int-3 Transgene Interferes with Cell Differentiation and Induces Neoplastic Transformation in Mammary and Salivary Glands," Genes & Development, 6:345-355 (1992), Cold Spring Harbor Laboratory Press, Box 100, 1 Bungtown Road, Cold Spring Harbor, New York 11724-2203.

Joutel and Tournier-Lasserve., "Notch Signalling Pathway and Human Diseases," Seminars in Cell & Departmental Biology, 9:619-625 (1998), Academic Press, Orlando, FL 32887.

Joutel et al., "Notch3 Mutations in Cadasil, A Herediraty Adult Onset Consition Causing Stroke and Dementia," Nature, 383:707-710 (1996), Macmillan Magazines Ltd., 4 Little Essex Street, London WC2R 3LF.

Karanu et al., "The Notch Ligand Jagged-L Represents a Novel Growth Factor of Human Hematopoietic Stem Cells," J. Exp. Med, 192: 1365-1372 (Nov. 6, 2000), The Rockefeller University Press, 1114 First Avenue, New York, 10021.

Kidd et al., "Sequence of the Notch Locus of *Drosophila* Melanogaster: Relationship of the Encoded Protein to Mammalian Clotting and Growth Factors," Molecular and Cellular Biology, 6:3094-3108 (1986), American Society for Microbiology, 1913 I St., NW, Washington, DC 20006.

Kopper and Hajdu "Tumor Stem Cells," Pathology Oncology Research, 10:69-73 (2004), Arányi Lajor Foundation, Budapest.

Krebs et al., "Notch Signaling is Essential for Vascular Morphogenesis in Mice," Genes & Development, 14:1343-1352 (2000), Cold Spring Harbor Laboratory Press, Box 100, 1 Bungtown Road, Cold Spring Harbor, New York 11724-2203.

Kuukasjärvi et al., "Genetic Heterogeneity and Clonal Evolution Underlying Development of Asynchronous Metastasis in Human Breast Cancer," Cancer Research, 57:1597-1604 (Apr. 15, 1997), American Association for Cancer Research, Inc., P.O. Box 3000, Denville, NJ 7834.

Lapidot et al., "A Cell Initiating Human Acute Myeloid Leukaemia after Transplantation into SCID Mice," Nature, 367:645-648 (1994), Macmillan Magazines Ltd., 4 Little Essex Street, London WC2R 3LF.

Lawrence et al., "Notch Signaling Targets the Wingless Responsiveness of a Ubx Visceral Mesoderm Enhancer in *Drosophila*," Current Biology, 11:375-385 (2001), Cell Press, 1100 Massachusetts Avenue, Cambridge, MA 02138.

Leethanakul et al., "Distinct Pattern of Expression of Differentiation and Growth-Related Genes in Squamous Cell Carcinomas of the Head and Neck Revealed by the Use of Laser Capture Microdissection and Cdna Arrays," Oncogene, 19:3220-3224 (2000), Nature Publishing Group, Houndmills, Basingstoke, Hampshire RG21 6XS, UK.

Leong and Karsan, "Recent insights into the role of Notch signaling in tumorigenesis," Blood, 107:2223-2233 (2006), American Society of Hematology.

Leong et al., "Activated Notch4 Inhibits Angiogenesis: Role of β1-Integrin Activartion," Mol. Cell. Biol., 22:2830-2841, (2002) American Society for Microbiology.

McCright et al., "Defects In Development of the Kidney, Heart and Eye Vasculature in Mice Homozygous for a Hypomorphic Notch2 Mutation," Development, 128:491-501 (2001), The Company of Biologists Limited, Bidder Building, 140 Cowley Road, Cambridge CB4 ODL, UK.

Mohr, "Character Caused By Mutation of an Entire Region of a Chromosome in *Drosophila*," Genetics, 4:275-292 (1919), The Genetics Society of America, GENETICS Mellon Institute, Box I 4400 Fifth Avenue Pittsburgh, Pennsylvania 15213-2683.

Parr et al., "The Possible Correlation of Notch-1 and Notch-2 with Clinical Outcome and Tumor Clinicpathological Parameters in Human Breast Cancer," International Journal of Molecular Medicine, 14:779-786 (2004), Springer Verlag, Tiergartenstasse 17, 69121 Heidelberg, Germany.

Pear and Aster, "T Cell Acute Lymphoblastic Leukemia/Lymphoma: A Human Cancer Commonly Associated with Aberrant Notch1 Signaling," Current Opinion in Hematology, 11:426-433 (2004), Lippincott Williams & Wilkins, Philadelphia, PA 19106.

Politi et al., "Notch in Mammary Gland Development and Breast Cancer," Seminars in Cancer Biology, 14:341-347 (2004), Academic Press, 6277 Sea Harbor Drive, Orlando, FL, 32887-4900.

Purow et al., "Expression of Notch-1 and Its Ligands, Delta-Like-1 and Jagged-1, is Critical for Glioma Cell Survival and Proliferation," Clinical Research, 65:2354-2363 (2005), American Association for Cancer Research, Philadelphia, PA 19106-4404.

Rae et al., "Novel Association of a Diverse Range of Genes with Renal Cell Carcinoma as Identified by Differential Display," Inter. J. Cancer, 88:726-732 (2000), John Wiley & Sons, Inc, 350 Main Street, Malden MA 02148, USA.

Rebay et al., "Specific Egf Repeats of Notch Mediate Interactions with Delta and Serrate: Implications for Notch as a Multifunctional Receptor," Cell, 67:687-699 (1991), Cell Press, 50 Church Street, Cambridge, Massachusetts 02138.

Reya et al., "Stem Cells, Cancer and Cancer Stem Cells ,"Nature, 414:105-111 (2001), Nature Publishing Group, New York, NY 10013-1917, USA.

Robey et al., "An Activated Form of Notch Influences the Choice Between Cd4 and Cd8 T Cell Lineages," Cell, 87:483-492 (1996), Cell Press, 50 Church Street, Cambridge, Massachusetts 02138.

Smith et al., "Constitutive Expression of a Truncated Int3 Gene in Mouse Mammary Epithelium Impairs Differentiation and Functional Development," Cell Growth & Differentiation, 6: 563-577 (1995), American Association for Cancer Research, Philadelphia, PA 19106-4404.

Soriano et al., "Expression of an Activated Notch4(Int-3) Oncoprotein Disrupts Morphogenesis and Induces an Invasive Phenotype in Mammary Epithelial Cells in Vitro," Intl. J. Cancer, 86: 652-659 (2000), John Wiley & Sons Inc, 350 Main Street, Malden MA 02148, USA.

Suzuki et al., "Imbalanced Expression of Tan-L and Human Notch4 in Endometrial Cancers," International Journal of Oncology, 17: 1131-1139 (2000), Spandidos—publications, Athens 116 10, Greece.

Swiatek et al., "Notch1 is essential for postimplantation development in mice," Genes & Development, 8:707-719, (1994) Cold Spring Harbor Laboratory.

Takeshita et al., "Crictical Role of Endothelial Notch1 Signaling in Postnatal Angiogenesis," Cir. Res. 100:70-78 (2007), American Heart Association, Inc.

Tavares et al., "Inhibition of Vascular Endothelium by the Notch-Ligand Delta-4 Unveils a Novel Therapeutic Target," Vascular Wall Biology, Poster Board #—Session: 115-II, Abstract# 1944, pp. 531a, (2003), American Society of Hematology, San Diego, California.

Uyttendaele et al., "Notch4 and Wnt-L Proteins Function to Regulate Branching Morphogenesis of Malnmary Epithelial Cells in an Opposing Fashion," Developmental Biology, 196:204-217 (1998), Academic Press, Orlando, FL 32887•4900.

Van Es and Clevers, "Notch and Wnt Inhibitors as Potential New Drugs for Intestinal Neoplastic Disease," Trends in Molecular Medicine, 11: 496-502 (2005), Elsevier, London, UK WC1X 8RR.

Van Limpt et al., "Sage Analysis of Neuroblastoma Reveals a High Expression of The Human Homologue of the *Drosophila* Delta Gene," Medical and Pediatric Oncology, 35:554-558 (2000), Wiley-Liss, Inc, 605 Third Avenue, New York, NY 10158-0012.

Varnum-Finney et al., "Pluripotent, Cytokine-dependent, Hematopoietic Stem Cells are Immortalized by Constitutive Notch1 Signaling," Nature Medicine, 6:1278-1281 (2000), Nature Publishing Group, New York, NY 10013-1917, USA.

Weijzen et al., "Activation of Notch-L Signaling Maintains the Neoplastic Phenotype in Human Ras-Transformed Cells," Nature Medicine, 8 :979-986 (2002), Nature Publishing Group, New York, NY 10013-1917, USA.

Wharton et al., "Nucleotide Sequence from the Neurogenic Locus Notch Implies a Gene Product that Shares Homology with Proteins Containing Egf-Like Repeats," Cell, 43:567-581 (1985) , Cell Press, 50 Church Street, Cambridge, Massachusetts 02138.

Xu et al., "Regions of *Drosophila* Notch that Contribute to Ligand Binding and the Modulatory Influence of Fringe," The Journal of Biological Chemistry, 280: 30158-30165 (2005), American Society for Biochemistry and Molecular Biology, Inc., 9650 Rockville Pike, Bethesda, MD 20814 U.S.A.

Xue et al., "Embryonic Lethality and Vascular Defects in Mice Lacking the Notch Ligand Jagged1," Human Molecular Genetics, 8: 723-730 (1999), Oxford University Press, McLean, VA 22101-0850, USA.

Zagouras et al., "Alterations in Notch Signaling in Neoplastic Lesions of the Human Cervix," PNAS, 92: 6414-6418 (1995), National Academy of Sciences, Washington, DC 20001.

The Extended European Search Report issued in European Application No. EP 07 777 332.3, on Aug. 11, 2009 (10 pages).

Sakamoto, K., et al., "Distinct roles of EGF repeats for the Notch signaling system," *Experimental Cell Research*, 2005, 281-291, 302(2), Elsevier, Orlando, FL, XP-004649921.

Shao, L., et al., "Fringe modifies O-fucose on mouse Notch1 at epidermal growth factor-like repeats within the ligand-binding site and the Abruptex region," *The Journal of Biological Chemistry*, 2003, 7775-7782, 278(10), American Society for Biochemistry and Molecular Biology, Bethesda, MD, XP-002538409.

Peters, N., et al., "CADASIL-associated Notch3 mutations have differential effects both on ligand binding and ligand-induced Notch3 receptor signaling through RBP-Jk," *Experimental Cell Research*, 2004, 454-464, 299 (2), Elsevier, Orlando, FL, XP-004537012.

Pei, Z. and Baker, N., "Competition between Delta and the Abruptex domain of Notch," *BMC Dev. Biol.* 8:4, BioMed Central, England (2008).

Luo, B., et al., "Isolation and functional analysis of a cDNA for human Jagged2, a gene encoding a ligand for the Notch1 receptor," *Mol. Cell. Biol.17*:6057-6067, American Society for Microbiology, United States (1997).

International Search Report for International Application No. PCT/US09/03994, ISA/US, Alexandria, Virgina, USA, mailed on Jul. 23, 2010.

Shimizu, K., et al., "Physical 1-15 interaction of Delta1, Jagged1, and Jagged2 with Notch1 and Notch3 receptors," *Biochem. Biophys. Res. Commun.* 276:385-389, Academic Press, United States (2000).

Rand, M., et al., "Calcium binding to tandem repeats of EGF-like modules. Expression and characterization of the EGF-like modules of human Notch-1 implicated in receptor-ligand interactions," *Protein Science* 6:2059-2071, Cambridge University Press, United Kingdom (1997).

Hambleton, S., et al., "Structural and Functional Properties of the Human Notch-1 Ligand Binding Region," *Structure* 12:2173-2183, Current Biology, Ltd., United States (2004).

Miele, L., Gamma-Secretase and Notch Signaling: Novel Therapeutic Targets In Breast Cancer, DTIC (Online), accessed at http://www.dtic.mil/cgi-bin/GetTRDoc?Location=U2&doc=GetTRDoc.pdf&AD=ADA446389 (retrieved on Jan. 12, 2010).

Dikic, I., et al., "Notch: Implications of endogenous inhibitors for therapy," *Bioessays* 32:481-487, John Wiley & Sons, United States (2010).

Lin, L., et al., "Targeting Specific Regions of the Notch3 Ligand-Binding Domain Induces Apoptosis and Inhibits Tumor Growth in Lung Cancer," *Can. Res.* 70:632-638, American Assoc. for Cancer Research, United States (2010).

Bheeshmachar, G., et al., "Evidence for a Role for Notch Signaling in the Cytokine-Dependent Survival of Activated T cells," *J. Immunol.* 177:5041-5050, The American Association of Immunologists Inc., United States (2006).

Extended European Search Report of European Appl. No. 08 72 4737.5, European Patent Office, Munich, Germany, dated Sep. 24, 2010.

Novus, "Biologicals Product: Mouse Monoclonal anti-Notch 1 (A6) antibody datasheet," XP008115324, accessed at http://www.novusbio.com/data_sheet/pdf_data_sheet/5985, 2006.

Allenspach, E.J., et al., "Notch Signaling in Cancer," *Cancer Biol.* 1:466-476, Landes Bioscience, United States (2002).

Armstrong, F., et al., "NOTCH is a key regulator of human T-cell acute leukemia initiating cell activity," *Blood 113*:1730-1740, The American Society of Hematology, United States (2009).

Bellavia, D., et al., "Constitutive activtion of NF-Kband T-cell leukemia/lymphoma in Notch3 transgenic mice," *EMBO J.* 19:3337-3348, Oxford University Press, United States (2000).

Callahan, R. & Raafat, A., "Notch Signaling in Mammary Gland Tumorigenesis," *Journal of Mammary Gland Biology and Neoplasia* 6:23-36, Plenum Publishing Corporation, United States (2001).

Campbell, A.M., "Monoclonal antibody technology," vol. 13, pp. v-29, Elsevier Science Publishers B.V, The Netherlands, 1984.

Cox, C.V., et al., "Characterization of acute lymphoblastic leukemia progenitor cells," *Blood 104*:2919-2925, The American Society of Hematology, United States (2004).

Deftos, M.L., et al., "Correlating notch signaling with thymocyte maturation," *Immunity* 9:777-786, Cell Press, United States (1998).

English language Abstract of WIPO Patent Publication No. WO 02/00576 A1, Jan. 3, 2002.

Fleming, R.J., et al., "The Notch receptor and its ligands," *Trends in Cell Biol.* 7:437-441, Elsevier Science Ltd., The Netherlands (1997).

Fre, S., et al, "Notch signals control the fate of immature progenitor cells in the intestine," *Nature* 435:964-968, Nature Publishing Group, England (2005).

Gallahan, D., and Callahan, R., "The mouse mammary tumor associated gene INT3 is a unique member of the *NOTCH* gene family (*NOTCH4*),"*Oncogene 14*:1838-1890, Stockton Press, United States (1997).

Grabher, C., et al., "Notch 1 activation in the molecular pathogensis of T-cell acute lymphoblastic leukaemia," *Nature Reviews Cancer* 6:347-359, Nature Publishing Group, England (2006).

Imatani, A. and Callahan, R., "Identification of a novel *NOTCH-4/INT-3* RNA species encoding an activated gene product in certain human tumor cell lines," *Oncogene 19*:223-231, Macmillan Publishers Ltd., England (2000).

International Search Report for International Application No. PCT/US08/00884, United States Patent and Trademark Office, U.S.A., mailed on Oct. 1, 2008.

International Search Report for International Application No. PCT/US09/03995, United States Patent and Trademark Office, U.S.A., mailed on Mar. 2, 2010.

International Search Report for International Application No. PCT/US2008/001948, USPTO, mailed on Oct. 15, 2008.

Jang, M.S., et al., "Notch signaling as a target in multimodality cancer therapy," *Curr. Opin. Mol. Ther.* 2(1):55-65, Thomson Reuters (Scientific) Ltd., England (Feb. 2000).

Jarriault, S., et al., "Signaling downstream of activated mammalian Notch," *Nature* 377:355-358, Nature Publishing Group, England (1995).

Jehn, B.M., et al., "Cutting edge: protective effects of notch-1 on TCR-induced apoptosis," *J. Immunol. 162*:635-638, The American Association of Immunologists, United States (1999).

Jundt, F., et al., "Activated Notch1 signaling promotes tumor cell proliferation and survival in Hodgkin and anaplastic large cell lymphoma," *Blood 99*:3398-3403. The American Society of Hematology, United States (2002).

Lee, J-S, et al., "Intracisternal Type A Particle-Mediated Activation of the *Notch4/int3* Gene in a Mouse Mammary Tumor: Generation of Truncated *Notch4/int3* mRNAs by Retroviral Splicing Events." *J. Virol.* 73:5166-5171, American Society for Microbiology, United States (1999).

Lee, S-H, et al., "Mutational analysis of *NOTCH1, 2, 3,* and *4* genes in common solid cancers and acute leukemias," *APMIS 115*:1357-1363, The Authors Journal Compilation, United States (2007).

Li, K., et al., "Modulation of Notch Signaling by Antibodies Specific for the Extracellular Negative Regulatory Region of NOTCH3," *J. Biol. Chem. 283*:8046-8054, The American Society for Biochemistry and Molecular Biology, Inc., United States (2008).

Li, L., et al., "The Human Homolog of Rat *Jagged1* Expressed by Marrow Stroma Inhibits Differentiation of 32D Cells through Interaction with Notch1," *Immunity* 8:43-55, Cell PRess, United States (1998).

Li, L., et al., "Cloning, Characterization, and the Complete 56.8-Kilobase DNA Sequence of the Human NOTCH4 Gene," *Genomics* 51:45-48, Academic Press, United States (1998).

Lindsell, C.E., et al., "Jagged: A Mammalian Ligand That Activates Notch1," *Cell* 80:909-917, Cell Press, United States (1995).

Liu, Z., et al., "Notch1 loss of heterozygosity causes vascular tumors and lethal hemorrhage in mice," *J. Clin. Invest. 121*(2):800-8, American Society for Clincal Investigation, United States (Feb. 2011; Epub Jan. 25, 2011).

Miele, L., & Osborne, B., "Arbiter of Differentiation and Death: Notch Signaling Meets Apoptosis," *J. Cell Physiol. 181*:393-409, Wiley-Liss, Inc., United States (1999).

Nam, Y., et al., "Notch signaling as a therapeutic target," *Curr. Opin. Chem. Biol. 6*:501-509, Elsevier Science Ltd., Holland (2002).

Pelegrin, A., et al., "[Immunotargeting of tumors: state of the art and prospects in 2000]," *Bull. Cancer 87*(11):777-91, John Libbey Eurotext, France (Nov. 2000) in the English language.

Pelegrin, A., et al., "[Immunotargeting of tumors: state of the art and prospects in 2000]," *Bull. Cancer 87*(11):777-91, John Libbey Eurotext, France (Nov. 2000) in the French language.

Sambandam, A., et al., "Notch signaling controls the generation and differentiation of early T lineage progenitors," *Nature Immunol. 6*:663-670, Nature Publishing Group, England (2005).

Soriano, J.V., et al., "Expression of an activated Notch(int-3) oncoprotein disrupts morphogenesis and induces and invasive phenotype in mammary epithelial cells in vitro," *Int. J. Cancer 86*: 652-659, Wiley-Liss, Inc., United States (2000).

Sugaya, K., et al., "Gene organization of human NOTCH4 and (CTG)n polymorphism in this human counterpart gene of mouse proto-oncogene Int3," *Gene 189*:235-244, Elsevier Science B.V., Holland (1997).

Summons to attend oral proceedings pursuant to Rule 115(1) EPC for European Patent Application 05722705.0-2402/1718767, European Patent Office, Germany, mailed on Feb. 9, 2011.

Thelu, J., et al., "Notch signaling is linked to epidermal cell differentiation level in basal cell carcinoma, psoriasis and wound healing," *BMC Dermatology 2*:7, BioMed Central, England (2002).

Van Es, J.H., et al., "Notch/γ-secretase inhibition turns proliferative cells in intestinal crypts and adenomas into goblet cells," *Nature 435*:959-963, Nature Publishing Group, England (2005).

Weng, A.P., and Aster, J.C., "Multiple niches for Notch in cancer: context is everything," *Curr. Opin. Genet. Dev. 14*(1):48-54, Elsevier, England (Feb. 2004).

Weng, A.P., et al., "Activating Mutations of *NOTCH1* in Human T Cell Acute Lymphoblastic Leukemia," *Science 306*:269-271, Nature Publishing Group, England (2004).

Weng, A.P., et al., "Growth Suppression of Pre-T Acute Lymphoblastic Leukemia Cells by Inhibition of Notch Signaling," *Mol. Cell Biol. 23*:655-644, American Society for Microbiology, United States (2003).

Axelson, H., "Notch signaling and cancer: emerging complexity," *Semin. Cancer Biol. 14*:317-319, Elsevier Ltd., England (2004).

Curry, C.L., et al., "Gamma secretase inhibitor blocks Notch activation and induces apoptosis in Kaposi's sarcoma tumor cells," *Oncogene 24*:6333-6344, Nature Publishing Group, England (2005).

Dontu, G., et al., "Role of Notch signaling in cell-fate determination of human mammary stem/progenitor cells," *Breast Cancer Res. 6*:R605-R615, BioMed Central Ltd., England (2004).

Duan, Z., et al., "A Novel Notch Protein, N2N, Targeted by Neutrophil Elastase and Implicated in Hereditary Neutropenia," *Mol. Cell. Biol. 24*(1):58-70, American Society for Microbiology, United States (2004).

Harper, J.A , et al., "Notch signaling in development and disease," *Clin. Genet. 64*:461-472, Blackwell Munksgaard, Denmark (2003).

Hopfer, O., et al., "The Notch pathway in ovarian carcinomas and adenomas," *Br. J. Cancer 93*:709-718, Cancer Research UK, England (2005).

Huang, E.Y., et al., "Surface Expression of Notch1 on Thymocytes: Correlation with the Double-Negative to Double-Positive Transition," *J. Immunol. 171*:2296-2304, The American Association of Immunologists, United States (2003).

Maillard, I., et al., "Mastermind critically regulates Notch-mediated lymphoid cell fate decisions," *Blood 104*:1696-1702, The American Society of Hematology, United States (2004).

Qin, J.-Z., et al., "p53-independent NOXA induction overcomes apoptotic resistance of malignant melanomas," *Mol. Cancer Ther. 3*(8):895-902, American Association for Cancer Research, Inc., United States (2004).

Santa Cruz Biotechnology, Inc., "Notch 2 (25-255): sc-5545 datasheet," downloaded on Dec. 2, 2009.

NCBI Entrez, GenBank Report, Accession No. P01724, Burstein, Y. and Schechter, I., Entry Date Jul. 21, 1986, last updated Nov. 4, 2008.

NCBI Entrez, GenBank Report, Accession No. Q8VDC9, Sembi, P., Entry Date Mar. 1, 2002, last updated Oct. 31, 2006.

International Search Report for International Application No. PCT/US11/21135, International Searching Authority, Alexandria, Virginia, United States, mailed Jul. 20, 2011.

Written Opinion of the International Searching Authority for International Application No. PCT/US11/21135, International Searching Authority, Alexandria, Virginia, United States, mailed Jul. 20, 2011.

Liu, H., et al., "Notch3 is Critical for Proper Angiogenesis and Mural Cell Investment," *Circ. Res. 107*:860-70, American Heart Association, United States (2010).

Bolos, V., et al., "Notch Signaling in Development and Cancer," *Endocrine Reviews 28*(3):339-363, The Endocrine Society, United States (2007).

Miele, L., et al., "NOTCH Signaling as a Novel Cancer Therapeutic Target," *Curr. Cancer Drug Targets 6*(4):313-323, Bentham Science Publishers, Ltd., Netherlands (2006).

Tanaka M., et al., "Asymmetric localization of Notch2 on the microvillous surface in choroid plexus epithelial cells," *Histochem. Cell Biol. 127*(4):449-56, Epub Jan. 12, 2007, Springer Verlag, Germany.

Jurynczyk M., et al., "Notch3 Inhibition in Myelin-Reactive T Cells Down-Regulates Protein Kinase Cθand Attenuates Experimental Autoimmune Encephalomyelitis," *J. Immunology 180*(4):2634-40, The American Association of Immunologists Inc., United States (2008).

Bendig, M., "Humanization of Rodent Monoclonal Antibodies by CDR Grafting," in *METHODS: A companion to methods in Enzymology*, vol. 8., pp. 83-93 (1995).

Greenspan, N.S. and Di Cera, E., "Defining epitopes: It's not as easy as it seems," *Nat. Biotechnol. 17*(10):936-7, Nature America Publishing, United States (1999).

Panka, D.J., et al., "Variable region framework differences result in decreased or increased affinity of variant anti-digoxin antibodies," *Proc Natl Acad Sci U S A. 85*(9):3080-4, National Academy of Sciences, United States (1988).

Sriuranpong, V., et al., "Notch Signaling Induces Cell Cycle Arrest In Small Cell Lung Cancer Cells," *Cancer Res. 61*(7):3200-5, American Association for Cancer Research, United States (2001).

Talora, C., et al., "Specific down-modulation of Notch1 signaling in cervical cancer cells is required for sustained HPV-E6/E7 expression and late steps of malignant transformation," *Genes Dev. 16*(17):2252-63, Cold Spring Harbor Laboratory Press, United States (2002).

Ahmad, I., et al., "Involvement of Notch-1 in mammalian retinal neurogenesis: association of Notch-1 activity with both immature and terminally differentiated cells," *Mech. Dev. 53*(1):73-85, Elsevier Scientific Publishers, Ireland (1995).

Houde, C., et al., "Overexpression of the NOTCH ligand JAG2 in malignant plasma cells from multiple myeloma patients and cell lines," *Blood 104*(12):3697-704, American Society of Hematology, United States (2004).

Shawber, C., et al., "Notch signaling inhibits muscle cell differentiation through a CBF1-independent pathway," *Development 122*(12):3765-73, Company of Biologists Limited, England (1996).

"4G1" Notch1 monoclonal antibody; Abnova technical datasheet, accessed at www.abnova.com/products/products_details. asp?Catalog_id=1-1-00004851-M10, accessed on Nov. 9, 2012; 8 total pages.

McDaniell, R., et al., "NOTCH2 Mutations Cause Alagille Syndrome, a Heterogenous Disorder of the Notch Signaling Pathway," *Am. J. Hum. Genet.79*(1):169-73, University of Chicago Press, United States (2006).

Nickoloff, B.J., et al., "Notch signaling as a therapeutic target in cancer: a new approach to the development of cell fate modifying agents," *Oncogene 22*(42):6598-608, Nature Publishing Group, England (2003).

Varnum-Finney, B., et al., "The Notch Ligand, Jagged-1, Influences the Development of Primitive Hematopoietic Precursor Cells," *Blood* 91(11):4084-91, The American Society of Hematology, United States (1998).

Jundt, F., et al., "Jagged1-induced Notch signaling drives proliferation of multiple myeloma cells," *Blood* 103:3511-3515, The American Society of Hematology, United States (2004).

Wu, Y., "Therapeutic antibody targeting of individual Notch receptors," *Nature* 464:1052-1057, Nature Publishing Group, England (2010).

Siebel, C.W. "PL07-04 Notch Antibody Antagonists for Cancer Therapy," Invited Abstracts (Plenary Session), Abstract nr PL07-04, American Association for Cancer Research, United States (2007).

Gordon, W.R., et al., "Structural basis for autoinhibition of Notch," *Nat. Struct. Mol. Biol.* 14(4):295-300, Nature Pub. Group, United States (2007).

Sanchez-Irizarry, C., "Notch Subunit Heterodimerization and Prevention of Ligand-independent Proteolytic Activation Depend, Respectively, on a Novel Domain and the LNR Repeats," *Mol. Cell Biol.* 24(21):9265-9273, American Society for Microbiology, United States (2004).

Roy, M., et al., "The multifaced role of Notch in cancer," *Curr. Opin. Genet. Dev.* 17(1):52-59, Elsevier, England (2007).

Supplemental Data for Li, K., et al., "Modulation of Notch Signaling by Antibodies Specific for the Extracellular Negative Regulatory Region of NOTCH3," *J. Biol. Chem.* 283:8046-8054, The American Society for Biochemistry and Molecular Biology, Inc., United States (2008); 9 total pages.

* cited by examiner

1A

1D

2A

2B

2C

2D

3A

M2 Melanoma Tumor

3B

Lu24 Lung Tumor

3C

3D

NOTCH1 RECEPTOR ANTIBODIES AND METHODS OF TREATMENT

BACKGROUND OF THE INVENTION

1. Field of the Invention

The present invention relates to compositions comprising an agent that binds a human Notch receptor and methods of using the compositions for characterizing, diagnosing, and treating cancer and other diseases. In particular, the present invention provides antibodies that specifically bind to a non-ligand binding membrane proximal region of the extracellular domain of a human Notch1 receptor and inhibit tumor growth. The present invention further provides methods of treating cancer, the methods comprising administering a therapeutically effective amount of an antibody that specifically binds to a non-ligand binding membrane proximal region of the extracellular domain of a human Notch1 receptor protein and inhibits tumor growth.

2. Background

Cancer is one of the leading causes of death in the developed world, resulting in over 500,000 deaths per year in the United States alone. Over one million people are diagnosed with cancer in the U.S. each year, and overall it is estimated that more than 1 in 3 people will develop some form of cancer during their lifetime. Though there are more than 200 different types of cancer, four of them—breast, lung, colorectal, and prostate—account for over half of all new cases (Jemal et al., 2003, *Cancer J. Clin.* 53:5-26).

Cancer arises from dysregulation of the mechanisms that control normal tissue development and maintenance, and increasingly stem cells are thought to play a central role (Beachy et al., 2004, *Nature* 432:324). During normal animal development, cells of most or all tissues are derived from normal precursors, called stem cells (Morrison et al., 1997, *Cell* 88:287-98; Morrison et al., 1997, *Curr. Opin. Immunol.* 9:216-21; Morrison et al., 1995, *Annu. Rev. Cell. Dev. Biol.* 11:35-71). Stem cells are cells that: (1) have extensive proliferative capacity; 2) are capable of asymmetric cell division to generate one or more kinds of progeny with reduced proliferative and/or developmental potential; and (3) are capable of symmetric cell divisions for self-renewal or self-maintenance. The best-known example of adult cell renewal by the differentiation of stem cells is the hematopoietic system where developmentally immature precursors (hematopoietic stem and progenitor cells) respond to molecular signals to form the varied blood and lymphoid cell types. Other cells, including cells of the gut, breast ductal system, and skin are constantly replenished from a small population of stem cells in each tissue, and recent studies suggest that most other adult tissues also harbor stem cells, including the brain.

Solid tumors are composed of heterogeneous cell populations. For example, breast cancers are a mixture of cancer cells and normal cells, including mesenchymal (stromal) cells, inflammatory cells, and endothelial cells. Classic models of cancer hold that phenotypically distinct cancer cell populations all have the capacity to proliferate and give rise to a new tumor. In the classical model, tumor cell heterogeneity results from environmental factors as well as ongoing mutations within cancer cells resulting in a diverse population of tumorigenic cells. This model rests on the idea that all populations of tumor cells would have some degree of tumorigenic potential. (Pandis et al., 1998, *Genes, Chromosomes & Cancer* 12:122-129; Kuukasjrvi et al., 1997, *Cancer Res.* 57:1597-1604; Bonsing et al., 1993, *Cancer* 71:382-391; Bonsing et al., 2000, *Genes Chromosomes & Cancer* 82: 173-183; Beerman H et al., 1991, *Cytometry* 12:147-54; Aubele M & Werner M, 1999, *Analyt. Cell. Path.* 19:53; Shen L et al., 2000, *Cancer Res.* 60:3884).

An alternative model for the observed solid tumor cell heterogeneity is that solid tumors result from a "solid tumor stem cell" (or "cancer stem cell" from a solid tumor) that subsequently undergoes chaotic development through both symmetric and asymmetric rounds of cell divisions. In this stem cell model, solid tumors contain a distinct and limited (possibly even rare) subset of cells that share the properties of normal "stem cells", in that they extensively proliferate and efficiently give rise both to additional solid tumor stem cells (self-renewal) and to the majority of tumor cells of a solid tumor that lack tumorigenic potential. Indeed, mutations within a long-lived stem cell population may initiate the formation of cancer stem cells that underlie the growth and maintenance of tumors and whose presence contributes to the failure of current therapeutic approaches.

The stem cell nature of cancer was first revealed in the blood cancer, acute myeloid leukemia (AML) (Lapidot et al., 1994, *Nature* 367:645-8). More recently it has been demonstrated that malignant human breast tumors similarly harbor a small, distinct population of cancer stem cells enriched for the ability to form tumors in immunodeficient mice. An ESA+, CD44+, CD24−/low, Lin-cell population was found to be 50-fold enriched for tumorigenic cells compared to unfractionated tumor cells (Al-Hajj et al., 2003, *PNAS* 100:3983-8). The ability to prospectively isolate the tumorigenic cancer cells has permitted investigation of critical biological pathways that underlie tumorigenicity in these cells, and thus promises the development of better diagnostic assays and therapeutics for cancer patients. It is toward this purpose that this invention is directed.

Normal stem cells and cancer stem cells share the ability to proliferate and self-renew, thus it is not surprising that a number of genes that regulate normal stem cell development contribute to tumorigenesis (reviewed in Reya et al., 2001, *Nature* 414:105-111 and Taipale & Beachy, 2001, *Nature* 411:349-354). The present invention identifies Notch receptor, for example, Notch1, as a marker of cancer stem cells, implicating the Notch signaling pathway in the maintenance of cancer stem cells and as a target for treating cancer via the elimination of these tumorigenic cells.

The Notch signaling pathway is one of several critical regulators of embryonic pattern formation, post-embryonic tissue maintenance, and stem cell biology. More specifically, Notch signaling is involved in the process of lateral inhibition between adjacent cell fates and plays an important role in cell fate determination during asymmetric cell divisions. Unregulated Notch signaling is associated with numerous human cancers where it can alter the developmental fate of tumor cells to maintain them in an undifferentiated and proliferative state (Brennan and Brown, 2003, *Breast Cancer Res.* 5:69). Thus carcinogenesis can proceed by usurping homeostatic mechanisms controlling normal development and tissue repair by stem cell populations (Beachy et al., 2004, *Nature* 432:324).

The Notch receptor was first identified in *Drosophila* mutants with haploinsufficiency resulting in notches at the wing margin, whereas loss-of-function produces an embryonic lethal "neurogenic" phenotype where cells of the epidermis switch fate to neural tissue (Moohr, 1919, *Genet.* 4:252; Poulson, 1937, *PNAS* 23:133; Poulson, 1940, *J. Exp. Zool.* 83:271). The Notch receptor is a single-pass transmembrane receptor containing numerous tandem epidermal growth factor (EGF)-like repeats and three cysteine-rich Notch/LIN-12 repeats (LNRs) within a large extracellular domain (Wharton et al., 1985, *Cell* 43:567; Kidd et al., 1986, *Mol. Cell Biol.*

6:3094; reviewed in Artavanis et al., 1999, Science 284:770). The LNRs and an additional C-terminal tail of approximately 103 amino acids of the extracellular domain are referred to herein as the "membrane proximal region". This region is also known as, and referred to as the Notch negative regulatory region (NRR).

Mammalian Notch receptors undergo cleavage to both form the mature receptor and following ligand binding to activate downstream signaling. A furin-like protease cleaves the Notch receptor precursors during maturation to generate juxtamembrane heterodimers that comprise a non-covalently associated extracellular subunit and a transmembrane subunit held together in an auto-inhibitory state. Ligand binding relieves this inhibition and induces cleavage of the Notch receptor by an ADAM-type metalloprotease and gamma-secretase, the latter of which releases the intracellular domain (ICD) into the cytoplasm, allowing it to translocate into the nucleus to activate gene transcription. Cleavage by ADAM occurs within the non-ligand binding cleavage domain within the juxtamembrane negative regulatory region (NRR) (See FIG. 1A). In the Notch1 receptor this region encompasses from about amino acid 1427 to about amino acid 1732.

Four mammalian Notch proteins have been identified (Notch1, Notch2, Notch3, and Notch4), and mutations in these receptors invariably result in developmental abnormalities and human pathologies including several cancers as described in detail below (Gridley, 1997, *Mol. Cell Neurosci.* 9:103; Joutel & Tournier-Lasserve, 1998, *Semin. Cell Dev. Biol.* 9:619-25).

The Notch receptor is activated by single-pass transmembrane ligands of the Delta, Serrated, Lag-2 (DSL) family. There are five known Notch ligands in mammals: Delta-like 1 (DLL1), Delta-like 3 (DLL3), Delta-like 4 (DLL4), Jagged 1 and Jagged 2 characterized by a DSL domain and tandem EGF-like repeats within the extracellular domain. The extracellular domain of the Notch receptor interacts with that of its ligands, typically on adjacent cells, resulting in two proteolytic cleavages of Notch; one extracellular cleavage mediated by an ADAM (A Disintegrin And Metallopeptidase) protease and one cleavage within the transmembrane domain mediated by gamma secretase. This latter cleavage generates the Notch intracellular domain (ICD), which then enters the nucleus where it activates the CBF1, Suppressor of Hairless [Su(H)], Lag-2 (CSL) family of transcription factors as the major downstream effectors to increase transcription of nuclear basic helix-loop-helix transcription factors of the Hairy and Enhancer of Split [E(spl)] family (Artavanis et al., 1999, *Science* 284:770; Brennan and Brown, 2003, *Breast Cancer Res.* 5:69; Iso et al., 2003, *Arterioscler. Thromb. Vasc. Biol.* 23:543). Alternative intracellular pathways involving the cytoplasmic protein Deltex identified in *Drosophila* may also exist in mammals (Martinez et al., 2002, *Curr. Opin. Genet. Dev.* 12:524-33), and this Deltex-dependent pathway may act to suppress expression of Wnt target genes (Brennan et al., 1999, *Curr. Biol.* 9:707-710; Lawrence et al., 2001, *Curr. Biol.* 11:375-85).

Hematopoietic stem cells (HSCs) are the best understood stem cells in the body, and Notch signaling is implicated both in their normal maintenance as well as in leukemic transformation (Kopper & Hajdu, 2004, *Pathol. Oncol. Res.* 10:69-73). HSCs are a rare population of cells that reside in a stromal niche within the adult bone marrow. These cells are characterized both by a unique gene expression profile as well as an ability to continuously give rise to more differentiated progenitor cells to reconstitute the entire hematopoietic system. Constitutive activation of Notch1 signaling in HSCs and progenitor cells establishes immortalized cell lines that generate both lymphoid and myeloid cells in vitro and in long-term reconstitution assays (Varnum-Finney et al., 2000, *Nat. Med.* 6:1278-81), and the presence of Jagged1 increases engraftment of human bone marrow cell populations enriched for HSCs (Karanu et al., 2000, *J. Exp. Med.* 192:1365-72). More recently, Notch signaling has been demonstrated in HSCs in vivo and shown to be involved in inhibiting HSC differentiation. Furthermore, Notch signaling appears to be required for Wnt-mediated HSC self-renewal (Duncan et al., 2005, *Nat. Immunol.* 6:314).

The Notch signaling pathway also plays a central role in the maintenance of neural stem cells and is implicated both in their normal maintenance as well as in brain cancers (Kopper & Hajdu, 2004, *Pathol. Oncol. Res.* 10:69-73; Purow et al., 2005, *Cancer Res.* 65:2353-63; Hallahan et al., 2004, *Cancer Res.* 64:7794-800). Neural stem cells give rise to all neuronal and glial cells in the mammalian nervous system during development, and more recently have been identified in the adult brain (Gage, 2000, *Science* 287:1433-8). Mice deficient for Notch1; the Notch target genes Hes1, 3, and 5; and a regulator of Notch signaling presenilin1 (PS1) show decreased numbers of embryonic neural stem cells. Furthermore, adult neural stem cells are reduced in the brains of PS1 heterozygote mice (Nakamura et al., 2000, *J. Neurosci.* 20:283-93; Hitoshi et al., 2002, *Genes Dev.* 16:846-58). The reduction in neural stem cells appears to result from their premature differentiation into neurons (Hatakeyama et al., 2004, *Dev.* 131:5539-50) suggesting that Notch signaling regulates neural stem cell differentiation and self-renewal.

Aberrant Notch signaling is implicated in a number of human cancers. The Notch1 gene in humans was first identified in a subset of T-cell acute lymphoblastic leukemias as a translocated locus resulting in activation of the Notch pathway (Ellisen et al., 1991, *Cell* 66:649-61). Constitutive activation of Notch1 signaling in T-cells in mouse models similarly generates T-cell lymphomas suggesting a causative role (Robey et al., 1996, *Cell* 87:483-92; Pear et al., 1996, *J. Exp. Med.* 183:2283-91; Yan et al., 2001, *Blood* 98:3793-9; Bellavia et al., 2000, *EMBO J.* 19:3337-48). Recently Notch1 point mutations, insertions, and deletions producing aberrant Notch1 signaling have been found to be frequently present in both childhood and adult T-cell acute lymphoblastic leukemia/lymphoma (Pear & Aster, 2004, *Curr. Opin. Hematol.* 11:416-33).

The frequent insertion of the mouse mammary tumor virus into both the Notch1 and Notch4 locus in mammary tumors and the resulting activated Notch protein fragments first implicated Notch signaling in breast cancer (Gallahan & Callahan, 1987, *J. Virol.* 61:66-74; Brennan & Brown, 2003, *Breast Cancer Res.* 5:69; Politi et al., 2004, *Semin. Cancer Biol.* 14:341-7). Further studies in transgenic mice have confirmed a role for Notch in ductal branching during normal mammary gland development, and a constitutively active form of Notch4 in mammary epithelial cells inhibits epithelial differentiation and results in tumorigenesis (Jhappan et al., 1992, *Genes & Dev.* 6:345-5; Gallahan et al., 1996, *Cancer Res.* 56:1775-85; Smith et al., 1995, *Cell Growth Differ.* 6:563-77; Soriano et al., 2000, *Int. J. Cancer* 86:652-9; Uyttendaele et al., 1998, *Dev. Biol.* 196:204-17; Politi et al., 2004, *Semin. Cancer Biol.* 14:341-7). Currently the evidence for a role for Notch in human breast cancer is limited to the expression of Notch receptors in breast carcinomas and their correlation with clinical outcome (Weijzen et al., 2002, *Nat. Med.* 8:979-86; Parr et al., 2004, *Int. J. Mol. Med.* 14:779-86). Furthermore, overexpression of the Notch pathway has been observed in cervical cancers (Zagouras et al., 1995, *PNAS* 92:6414-8), renal cell carcinomas (Rae et al., 2000, Int. J.

Cancer 88:726-32), head and neck squamous cell carcinomas (Leethanakul et al., 2000, *Oncogene* 19:3220-4), endometrial cancers (Suzuki et al., 2000, *Int. J. Oncol.* 17:1131-9), and neuroblastomas (van Limpt et al., 2000, *Med. Pediatr. Oncol.* 35:554-8) suggestive of a potential role for Notch in the development of a number of neoplasms. Interestingly, Notch signaling might play a role in the maintenance of the undifferentiated state of Apc-mutant neoplastic cells of the colon (van Es & Clevers, 2005, *Trends in Mol. Med.* 11:496-502).

The Notch pathway is also involved in multiple aspects of vascular development including proliferation, migration, smooth muscle differentiation, angiogenesis and arterial-venous differentiation (Iso et al., 2003, *Arterioscler. Thromb. Vasc. Biol.* 23:543). For example, homozygous null mutations in Notch1/4 and Jagged1 as well as heterozygous loss of DLL4 result in severe though variable defects in arterial development and yolk sac vascularization. Furthermore, DLL1-deficient and Notch-2-hypomorphic mice embryos show hemorrhage that likely results from poor development of vascular structures (Gale et al., 2004, *PNAS*, 101:15949-54; Krebs et al., 2000, *Genes Dev.* 14:1343-52; Xue et al., 1999, *Hum. Mel Genet.* 8:723-30; Hrabe de Angelis et al., 1997, *Nature* 386:717-21; McCright et al., 2001, *Dev.* 128: 491-502). In human, mutations in Jagged1 are associated with Alagille syndrome, a developmental disorder that includes vascular defects, and mutations in Notch3 are responsible for an inherited vascular dementia (Cadasil) in which vessel homeostasis is defective (Joutel et al., 1996, *Nature* 383:707-10).

The identification of Notch1, Notch4, DLL1 and DLL4 as genes expressed in cancer stem cells compared to normal breast epithelium suggests that targeting the Notch pathway can help eliminate not only the majority of nontumorigenic cancer cells, but the tumorigenic cells responsible for the formation and reoccurrence of solid tumors. Furthermore, because of the prominent role of angiogenesis in tumor formation and maintenance, targeting the Notch pathway can also effectively inhibit angiogenesis, starving a cancer of nutrients and contributing to its elimination.

Anti-Notch antibodies and their possible use as anti-cancer therapeutics have been reported. See, e.g., U.S. Patent Application Publication Nos. 2008/0131434 and 2009/0081238, each of which is incorporated by reference herein in its entirety. See also International Publication Nos. WO 2008/057144, WO 2008/076960, and WO 2008/50525.

BRIEF SUMMARY OF THE INVENTION

The present invention provides agents that bind to a non-ligand binding membrane proximal region of the extracellular domain of a Notch1 receptor and compositions, such as pharmaceutical compositions, comprising those agents. The invention further provides methods of targeting cancer stem cells with the agents. In some embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor. The invention also provides methods of using the agents in the treatment of cancer and/or in the inhibition of tumor growth.

In one aspect, the invention provides an antibody that specifically binds to a non-ligand binding membrane proximal region of the extracellular domain of a Notch1 receptor (e.g., human Notch1). In some embodiments, the non-ligand binding membrane proximal region of a Notch1 receptor comprises about amino acid 1427 to about amino acid 1732 of a human Notch1 receptor. In some embodiments, the membrane proximal region of a Notch1 receptor comprises SEQ ID NO:2. In certain embodiments, the antibody specifically binds to a non-ligand binding membrane proximal region of the extracellular domain of at least one additional Notch receptor family member.

In some embodiments the antibody is an antagonist of Notch1. In some embodiments, the antibody inhibits signaling by or activation of the Notch1 receptor. In some embodiments, the antibody inhibits Notch1 activity. In some embodiments, the antibody inhibits cleavage within the membrane proximal region. In certain embodiments, the antibody inhibits cleavage of the Notch1 receptor (e.g., cleavage at the S2 site by a metalloprotease) and/or inhibits activation of the Notch1 receptor by ligand binding. In some embodiments, the antibody inhibits release or formation of the intracellular domain (ICD) of Notch1. In certain embodiments, the antibody inhibits tumor growth.

In certain embodiments, the invention provides an antibody that binds a non-ligand binding membrane proximal region of the extracellular domain of a human Notch1 and comprises a heavy chain CDR1 comprising RGYWIE (SEQ ID NO:15), a heavy chain CDR2 comprising QILPGTGRTNYNEKFKG (SEQ ID NO:16), and/or a heavy chain CDR3 comprising FDGNYGYYAMDY (SEQ ID NO:17); and/or (b) a light chain CDR1 comprising RSSTGAVTTSNYAN (SEQ ID NO:18), a light chain CDR2 comprising GTNNRAP (SEQ ID NO:19), and/or a light chain CDR3 comprising ALWYSNHWVFGGGTKL (SEQ ID NO:20). In some embodiments, the antibody comprises a heavy chain variable region comprising: (a) a heavy chain CDR1 comprising RGYWIE (SEQ ID NO:15), or a variant thereof comprising 1, 2, 3, or 4 amino acid substitutions; (b) a heavy chain CDR2 comprising QILPGTGRTNYNEKFKG (SEQ ID NO:16), or a variant thereof comprising 1, 2, 3, or 4 amino acid substitutions; and/or (c) a heavy chain CDR3 comprising FDGNYGYYAMDY (SEQ ID NO:17), or a variant thereof comprising 1, 2, 3, or 4 amino acid substitutions. In certain other embodiments, the antibody comprises (or further comprises) a light chain variable region comprising: (a) a light chain CDR1 comprising RSSTGAVTTSNYAN (SEQ ID NO:18), or a variant thereof comprising 1, 2, 3, or 4 amino acid substitutions; (b) a light chain CDR2 comprising GTNNRAP(SEQ ID NO:19), or a variant thereof comprising 1, 2, 3, or 4 amino acid substitutions; and/or (c) a light chain CDR3 comprising ALWYSNHWVFGGGTKL (SEQ ID NO:20), or a variant thereof comprising 1, 2, 3, or 4 amino acid substitutions. In some embodiments, the amino acid substitutions are conservative amino acid substitutions.

In some embodiments, the invention provides an antibody, 52M51, produced by the hybridoma cell line deposited with the American Type Culture Collection (ATCC), 10801 University Boulevard, Manassas, Va., USA, under the conditions of the Budapest Treaty on Aug. 7, 2008, and assigned designation number PTA-9405. In some embodiments, the invention provides a humanized version of antibody 52M51, 52M51H4L3, as encoded by the DNA deposited with the ATCC, under the conditions of the Budapest Treaty on Oct. 15, 2008, and assigned designation number PTA-9549. In some embodiments, the invention provides an antibody that binds to the same epitope as the epitope to which antibody 52M51 binds.

In another aspect, the invention provides an antibody that binds a non-ligand binding membrane proximal region of the extracellular domain of a human Notch1 and the antibody comprises, consists, or consists essentially of an antibody "52R43" as encoded by the DNA deposited with the ATCC under the conditions of the Budapest Treaty on Oct. 15, 2008, and assigned designation number PTA-9548. In some embodiments, the invention provides an antibody that competes with 52R43 for specific binding to a non-ligand binding membrane proximal region of the extracellular domain of a human Notch1. Pharmaceutical compositions comprising 52R43 and methods of treating cancer comprising administering therapeutically effective amounts of the 52R43 antibody are also provided.

In certain embodiments, the invention provides an antibody that competes with any of the antibodies as described in the aforementioned embodiments and/or aspects, as well as other aspects/embodiments described elsewhere herein, for specific binding to a non-ligand binding membrane proximal region of the extracellular domain of a human Notch1 (e.g., in a competitive binding assay). Pharmaceutical compositions comprising the antibodies described herein and methods of treating cancer comprising administering therapeutically effective amounts of the antibodies are also provided.

In certain embodiments of each of the aforementioned aspects or embodiments, as well as other aspects and/or embodiments described elsewhere herein, the antibody is a recombinant antibody. In some embodiments, the antibody is a monoclonal antibody, achimeric antibody, a humanized antibody, or a human antibody. In certain embodiments, the antibody is an antibody fragment. In certain embodiments, the antibody or antibody fragment is monovalent, monospecific, bivalent, bispecific, or multispecific. In certain embodiments, the antibody is conjugated to a cytotoxic moiety. In certain embodiments, the antibody is isolated. In still further embodiments, the antibody is substantially pure.

Pharmaceutical compositions comprising the antibodies described herein and methods of treating cancer comprising administering therapeutically effective amounts of the antibodies described herein are also provided. In certain embodiments, the pharmaceutical compositions further comprise a pharmaceutically acceptable carrier.

In another aspect, the invention provides a polypeptide. In some embodiments, the polypeptide is an antibody (e.g., an antibody that specifically binds Notch1), a heavy chain or light chain of an antibody, and/or a fragment of an antibody. In some embodiments, the polypeptide is isolated. In certain embodiments, the polypeptide is substantially pure. In some embodiments, the polypeptide comprises an amino acid sequence of SEQ ID NO:8, SEQ ID NO:14, SEQ ID NO:24, SEQ ID NO:28, or SEQ ID NO:32. In some embodiments, the polypeptide comprises an amino acid sequence of SEQ ID NO:14 or SEQ ID NO:24 and/or an amino acid sequence of SEQ ID NO:8, SEQ ID NO:28, or SEQ ID NO:32. In some embodiments, the polypeptide comprises at least a portion of the amino acid sequence of SEQ ID NO:14 or SEQ ID NO:24, and/or at least a portion of the amino acid sequence of SEQ ID NO:8, SEQ ID NO:28, or SEQ ID NO:32. Pharmaceutical compositions comprising both the polypeptide and a pharmaceutically acceptable vehicle are further provided, as are cell lines that produce the polypeptide.

In some embodiments, the polypeptide comprises: (a) a polypeptide having at least about 80% sequence identity to SEQ ID NO:14 or SEQ ID NO:24; and/or (b) a polypeptide having at least about 80% sequence identity to SEQ ID NO:8, SEQ ID NO:28 or SEQ ID NO:32. In certain embodiments, the polypeptide is an antibody (e.g., an antibody that specifically binds to the non-ligand binding membrane proximal region of an extracellular domain of human Notch1). In certain embodiments, the polypeptide comprises a polypeptide having at least about 85%, at least about 90%, at least about 95%, at least about 98%, or about 100% sequence identity to SEQ ID NO:14, SEQ ID NO:24, SEQ ID NO:8, SEQ ID NO:28 or SEQ ID NO:32. In certain embodiments, the polypeptide comprises a heavy chain variable region and/or a light chain variable region of the 52M51 antibody. In some embodiments, the polypeptide comprises a heavy chain variable region and/or a light chain variable region of a humanized 52M51 antibody. In some embodiment, the polypeptide comprises a heavy chain variable region and/or a light chain variable region of antibody 52R43.

In another aspect, the invention provides a polynucleotide molecule encoding any of the antibodies and/or polypeptides of the aforementioned aspects, as well as other aspects/embodiments as described herein. In some embodiments, an expression vector comprises the polynucleotide molecule. In other embodiments, a host cell comprises the expression vector. In some embodiments, a host cell comprises the polynucleotide molecule. In some embodiments, the host cell is cell line or a hybridoma cell line. In certain embodiments, the hybridoma cell line produces the 52M51 antibody or a humanized 52M51 antibody.

In a further aspect, the invention provides a method of inhibiting activity of Notch1 in a cell, comprising contacting the cell with an effective amount of any of the antibodies or polypeptides described in the aforementioned aspects and embodiments, as well as other aspects/embodiments described elsewhere herein. In certain embodiments, the cell is a tumor cell.

In another aspect, the invention provides a method of inhibiting the growth of a tumor in a subject, the method comprising administering to the subject a therapeutically effective amount of any of the antibodies or polypeptides described in the aforementioned aspects and embodiments, as well as other aspects/embodiments described elsewhere herein. In some embodiments, the tumor comprises cancer stem cells. In some embodiments, the methods comprise targeting the cancer stem cells with the antibodies. In certain embodiments, the methods comprise reducing the frequency of cancer stem cells in a tumor, reducing the number of cancer stem cells in a tumor, reducing the tumorigenicity of a tumor, and/or reducing the tumorigenicity of a tumor by reducing the number or frequency of cancer stem cells in the tumor. In some embodiments, the methods comprise inhibiting the activity of a Notch1 receptor and/or inhibiting growth of a tumor. In certain embodiments, the tumor is selected from the group consisting of a breast tumor, colorectal tumor, hepatic tumor, renal tumor, lung tumor, pancreatic tumor, ovarian tumor, prostate tumor and head and neck tumor.

In another aspect, the present invention provides methods of treating cancer in a subject. In some embodiments, the method comprises administering to a subject a therapeutically effective amount of any of the antibodies or polypeptides described in the aforementioned aspects and/or embodiments, as well as other aspects/embodiments described elsewhere herein. In some embodiments, the cancer to be treated is breast cancer, colorectal cancer, hepatic cancer, kidney cancer, liver cancer, lung cancer, pancreatic cancer, gastrointestinal cancer, melanoma, ovarian cancer, prostate cancer, cervical cancer, bladder cancer, glioblastoma, and head and neck cancer. In certain embodiments of each of the aforementioned aspects or embodiments, as well as other aspects and/or embodiments described elsewhere herein, the method of treating cancer comprises inhibiting tumor growth.

In an additional aspect, the invention provides a method of inhibiting growth of a tumor in a subject, the method comprising administering to the subject a therapeutically effective amount of an antibody that specifically binds to a non-ligand binding membrane proximal region of an extracellular domain of human Notch1, wherein binding inhibits activity of Notch1.

In a further aspect, the invention provides a method of reducing the tumorigenicity of a tumor that comprises cancer stem cells by reducing the frequency or number of cancer stem cells in the tumor, the method comprising contacting the tumor with an effective amount of an antibody that inhibits the activity of Notch1.

In certain embodiments of each of the aforementioned aspects and/or embodiments, as well as other aspects or embodiments described herein, the methods further comprise administering to the subject at least one additional anti-cancer and/or therapeutic agent. In certain embodiments of each of the aforementioned aspects or embodiments, as well as other aspects and/or embodiments described elsewhere herein, the antibody or polypeptide is administered to a subject in combination with an additional treatment for cancer. In certain embodiments, the additional treatment for cancer comprises radiation therapy, chemotherapy, and/or an additional antibody therapeutic. In certain embodiments, the chemotherapy comprises taxol, irinotecan, gemcitabine and/or oxaliplatin. In certain embodiments, the additional antibody therapeutic is an antibody that specifically binds a second human Notch receptor (e.g., Notch2) or a human Notch receptor ligand (e.g., DLL4 or JAG1). In certain embodiments, the additional antibody therapeutic is an antibody that specifically binds VEGF. In certain embodiments, the subject treated is a human.

The invention further provides a method of treating cancer in a human, wherein the cancer comprising cancer stem cells is not characterized by overexpression by the cancer stem cell of one or more Notch receptors, comprising administering to the human a therapeutically effective amount of an antibody which binds to a membrane proximal region of the extracellular domain of a Notch1 receptor and blocks ligand activation of a Notch1 receptor.

The invention further provides a method of treating cancer in a human comprising administering to the human therapeutically effective amounts of (a) a first antibody which binds a Notch1 receptor and inhibits growth of cancer stem cells which overexpress Notch receptors; and (b) a second antibody which binds a Notch receptor and blocks ligand activation of a Notch receptor.

The invention also provides another method of treating cancer, wherein the cancer is selected from the group consisting of breast, colon, pancreatic, prostate, lung, rectal and colorectal cancer, comprising administering a therapeutically effective amount of an antibody that blocks ligand activation of a Notch1 receptor.

The invention additionally provides: a humanized antibody which binds Notch1 and blocks ligand activation of a Notch1 receptor; a composition comprising the humanized antibody and a pharmaceutically acceptable carrier; and an immunoconjugate comprising the humanized antibody conjugated with a cytotoxic agent.

Moreover, the invention provides an isolated polynucleotide encoding the humanized antibody; a vector comprising the nucleic acid; a host cell comprising the nucleic acid or the vector; as well as a process of producing the humanized antibody comprising culturing a host cell comprising the nucleic acid so that the nucleic acid is expressed and, optionally, further comprising recovering the humanized antibody from the host cell culture (e.g., from the host cell culture medium).

The invention further pertains to an immunoconjugate comprising an antibody that binds Notch conjugated to one or more calicheamicin molecules, and the use of such conjugates for treating Notch expressing cancer, e.g., a cancer in which cancer stem cells overexpress Notch.

Examples of solid tumors that can be treated using a therapeutic composition of the instant invention, for example, an antibody that binds a membrane promixal region of the extracellular domain of a Notch1 receptor include, but are not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma.

Where aspects or embodiments of the invention are described in terms of a Markush group or other grouping of alternatives, the present invention encompasses not only the entire group listed as a whole, but also each member of the group individually and all possible subgroups of the main group, and also the main group absent one or more of the group members. The present invention also envisions the explicit exclusion of one or more of any of the group members in the claimed invention.

(A) Schematic of the Notch receptor and 52M antigen region. The 52M antigen includes the area of the Notch1 receptor subject to cleavage by furin during maturation of the receptor and cleavage by ADAM (A Disintegrin and Metalloprotease) proteases following ligand binding. Subsequent processing by gamma-secretase causes the release of the intracellular domain (ICD) of Notch that activates gene transcription in the nucleus. (B) Luciferase levels (y-axis) derived from Notch1-Hela cells cultured in the presence of a soluble Notch ligand (hDLL4-fc) and Notch1 receptor antibodies. Results from non-transfected (NT) cells with and without hDLL4-Fc are shown on the far left of the x-axis. 52M Notch1 receptor antibodies are shown along the x-axis and compared to DBZ, a Notch gamma-secretase inhibitor (GSI), and 21M18, an anti-DLL4 antibody. Notch1 receptor antibodies 52M51, 52M63, 52M74 and 52M80 all significantly inhibited Notch signaling as indicated by a decrease in luciferase activity. (C) Luciferase levels (y-axis) derived from Notch1-Hela cells cultured in the presence of a soluble Notch ligand (hDLL4-fc) and Notch1 receptor antibodies. Results from non-transfected (NT) cells with and without hDLL4-Fc are shown on the far left of the x-axis. 52M51 murine hybridoma derived antibody and humanized variant 52M51-H4/L3 are shown along the x-axis in various concentrations as indicated. Both the parental murine antibody 52M51 and the humanized variant significantly inhibited Notch signaling as indicated by a decrease in luciferase activity. (D) Western blot analysis of ICD formation after ligand-mediated stimulation of Notch1 expressing Hela cells. Minimal ICD is produced in the absence of DLL4 ligand (-DLL4), but formation is stimulated by the presence of DLL4. Antibodies 52M51, 52M63, 52M74, and 52M80 reduce ICD formation to background levels despite the presence of DLL4.

Figure 2:
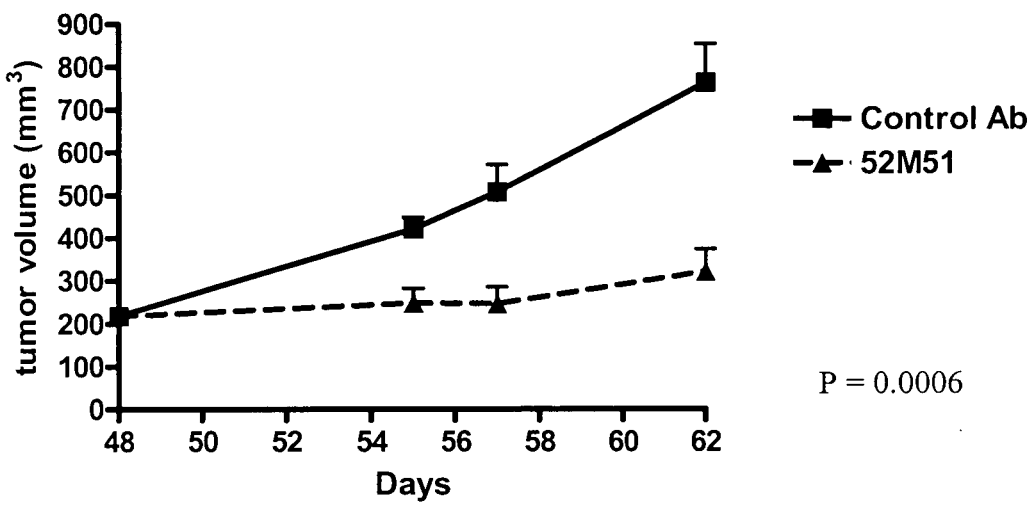
Figure 2:
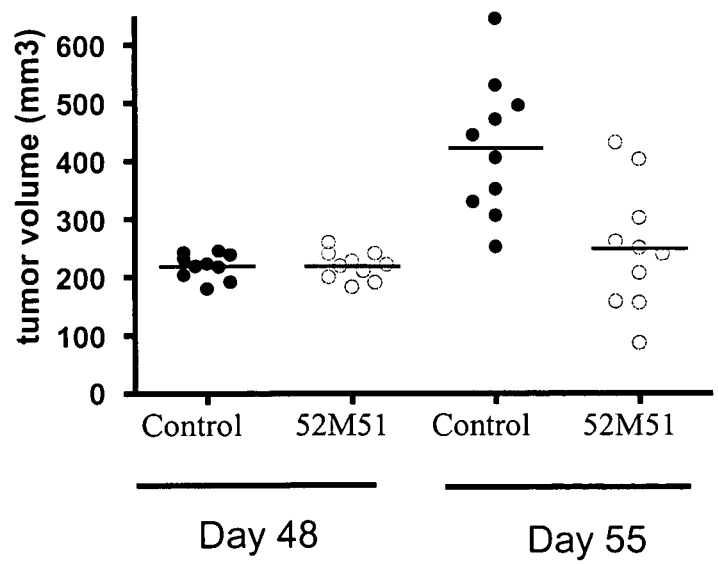
Figure 2:
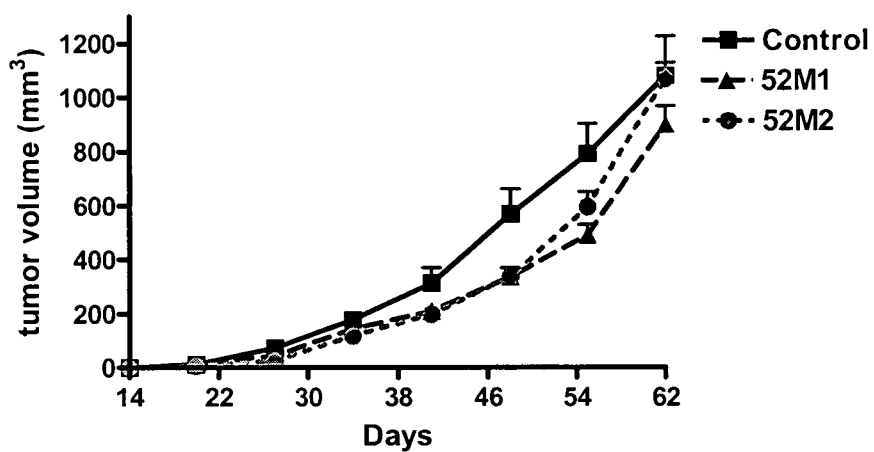
Figure 2:
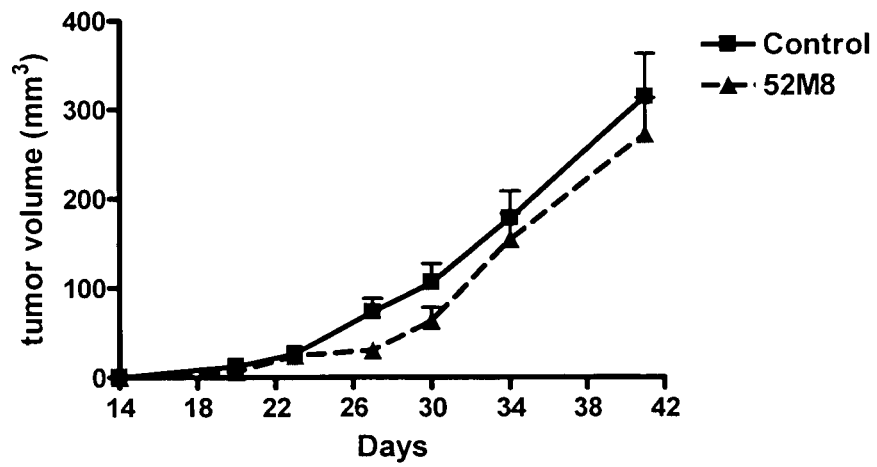

FIG. 2: Notch1 Receptor Antibody 52M51 Inhibits Tumor Formation In vivo.

Figure 1:
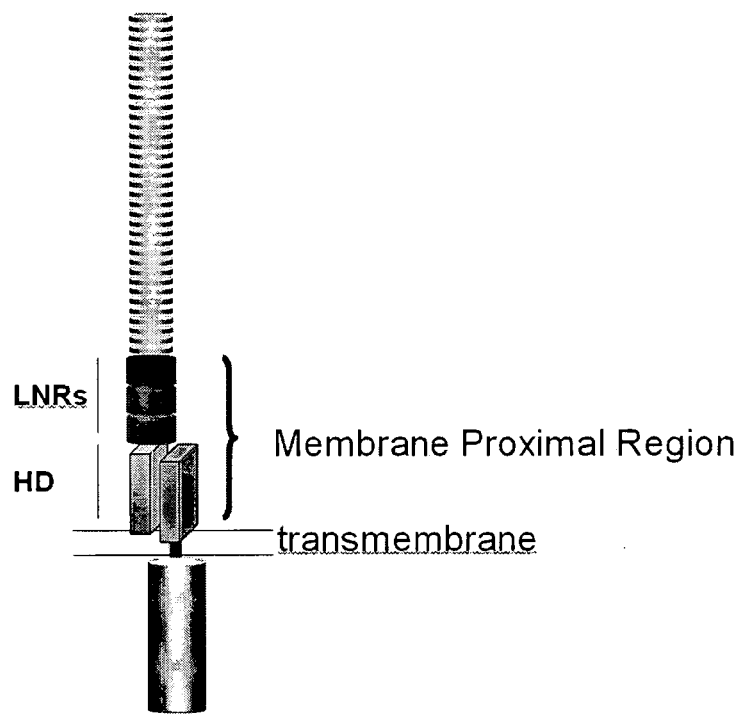
FIG. 1: Identification of Antibodies Targeting the Membrane Proximal Region of Notch that Inhibit Notch Signaling.
Figure 1:
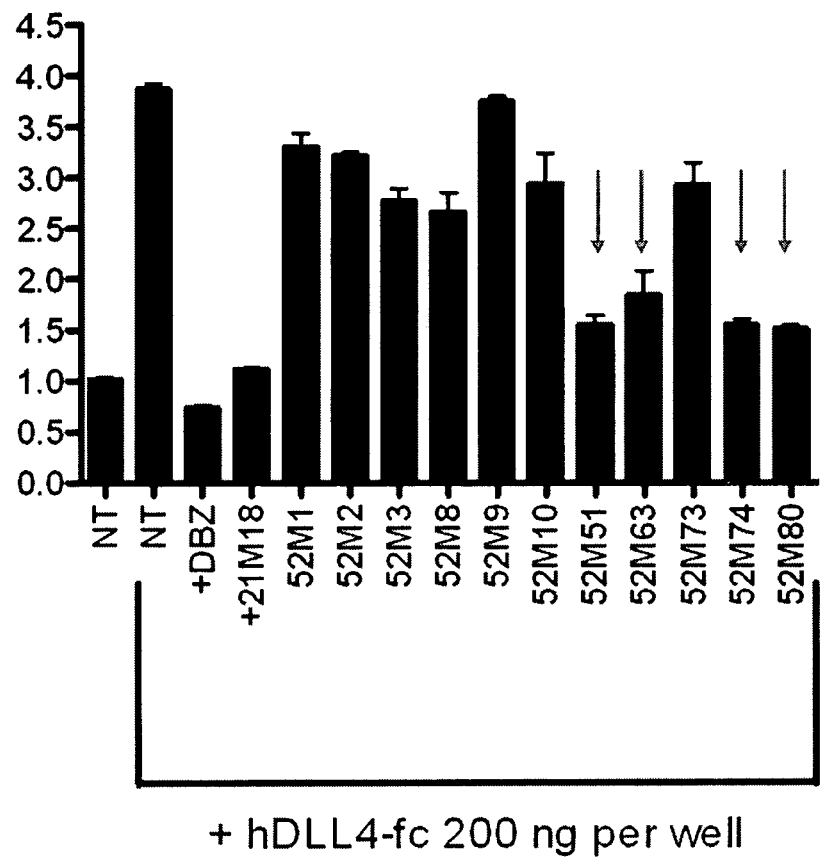
Figure 1:
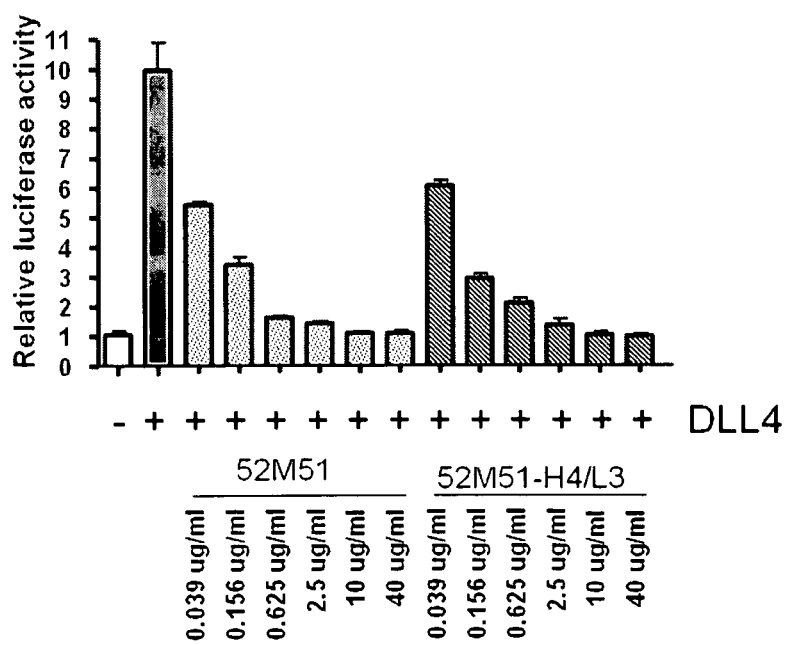
Figure 1:
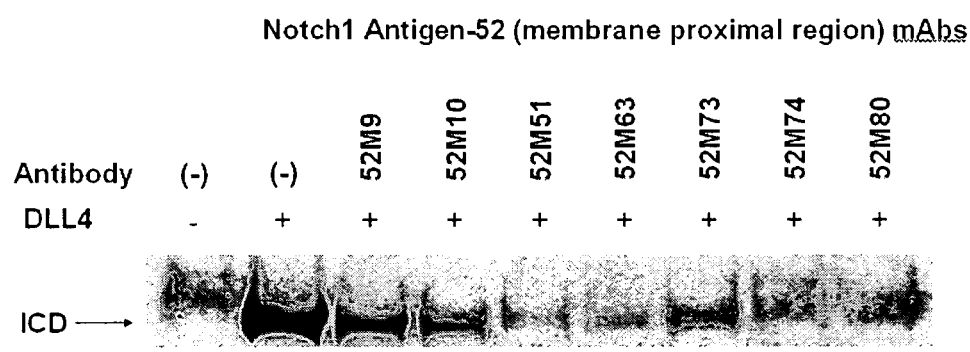

(A) NOD/SCID mice injected with C8 colon tumor cells were treated with control antibody (squares) or anti-Notch1 antibody 52M51 (triangles), and tumor volume (y-axis, mm$^3$) was measured across time (x-axis, days). Treatment with 52M51 antibodies significantly (p=0.0006) inhibited tumor growth compared to control. (B) Individual tumor volume measurements from animals in (A) measured on days 48 and 55 for control (left) versus 52M51 (right) treated mice. A line demarcates the average of each experimental group. (C) NOD/SCID mice injected with PE13 breast tumor cells were treated with control antibody (black squares) or anti-Notch1 antibodies that do not inhibit Notch signaling as shown in FIG. 1B: 52M1 (black triangles) and 52M2 (grey circles). Tumor volume (y-axis, mm$^3$) was measured across time (x-axis, days). Treatment with 52M1 and 52M2 failed to effect tumor growth when compared to control treated animals. (D) NOD/SCID mice injected with PE13 breast tumor cells were treated with control antibody (squares) or anti-Notch1 antibody 52M8 (triangles) that does not inhibit Notch signaling as shown in FIG. 1B. Tumor volume (y-axis, mm$^3$) was measured across time (x-axis, days). Treatment with 52M8 failed to effect tumor growth when compared to control treated animals.

Figure 3:
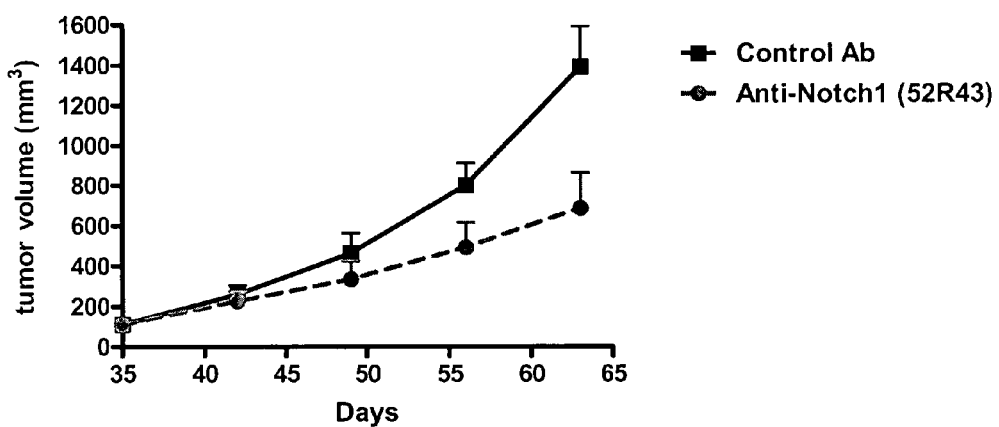
Figure 3:
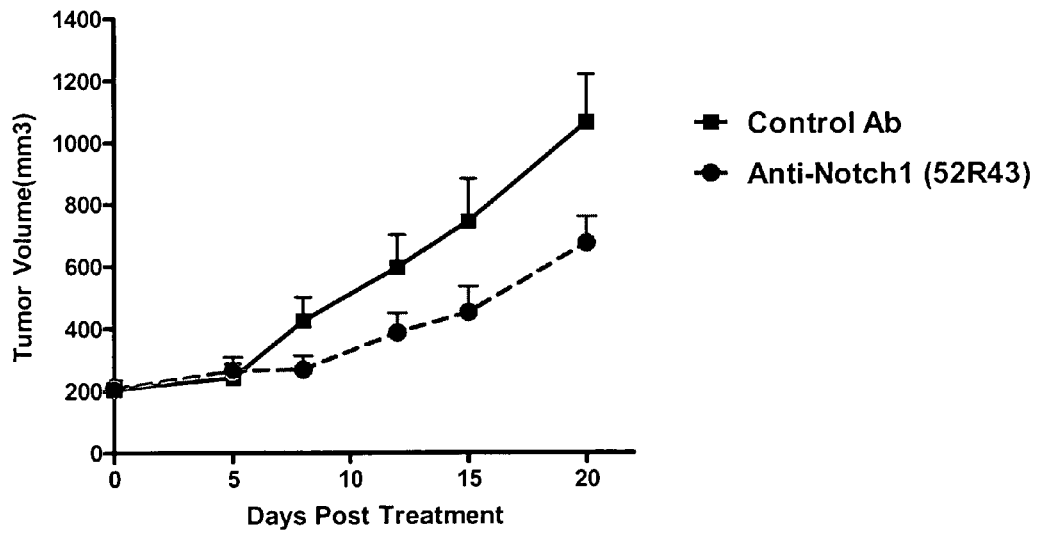
Figure 3:
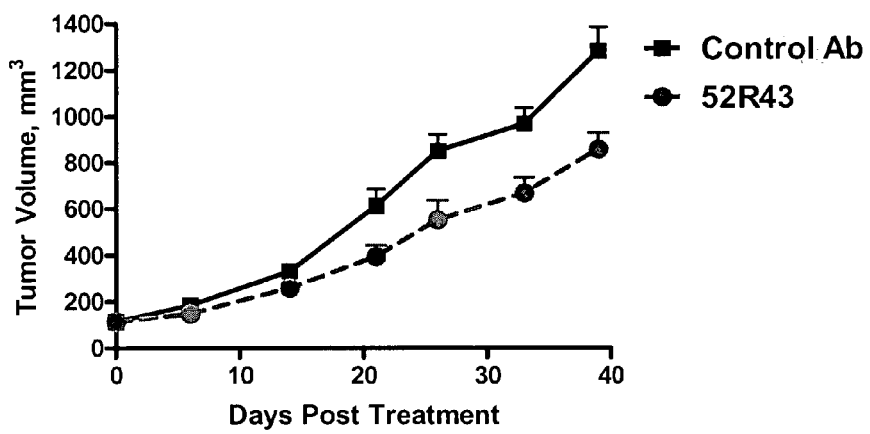
Figure 3:
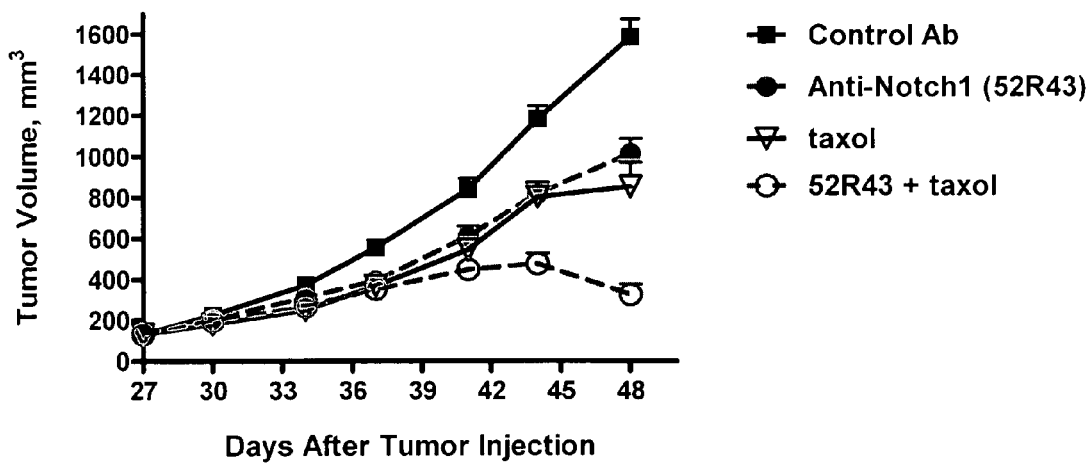

FIG. 3: Anti-Notch1 Receptor Antibody 52R43 Inhibits Tumor Growth In vivo (A) NOD/SCID mice injected with M2 melanoma tumor cells were treated with control antibody (squares) or anti-Notch1 antibody 52R43 (circles), and tumor volume (y-axis, mm$^3$) was measured across time (x-axis, days). (B) NOD/SCID mice injected with Lu24 lung tumor cells were treated with control antibody (squares) or anti-Notch1 antibody 52R43 (circles), and tumor volume (y-axis, mm$^3$) was measured across time (x-axis, days). (C) NOD/SCID mice injected with PN8 pancreatic tumor cells were treated with control antibody (squares) or anti-Notch1 antibody 52R43 (circles), and tumor volume (y-axis, mm$^3$) was measured across time (x-axis, days). (D) NOD/SCID mice injected with T1 breast tumor cells were treated with control antibody (squares), anti-Notch1 antibody 52R43 (closed circles), taxol (triangles) or 52R43 and taxol (open circles) and tumor volume (y-axis, mm$^3$) was measured across time (x-axis, days).

DETAILED DESCRIPTION OF THE INVENTION

The present invention provides novel agents, including, but not limited to polypeptides such as antibodies, that bind one or more human Notch receptors. The Notch-binding agents include antagonists of the human Notch receptor(s). Related polypeptides and polynucleotides, compositions comprising the Notch-binding agents, and methods of making the Notch-binding agents are also provided. Methods of using the novel Notch-binding agents, such as methods of inhibiting tumor growth and/or treating cancer, are further provided.

The present invention further identifies molecules (e.g., antibodies) that specifically bind to a non-ligand binding membrane proximal region of the extracellular domain of a human Notch1 receptor and inhibit tumor growth in vivo. The ligand binding region of Notch, which is necessary and sufficient for ligand binding, has been identified as EGF repeats 11 and 12, suggesting this region of the Notch receptor is important in Notch signaling and tumorigenesis (Rebay et al., 1991, Cell 67:687; Lei et al., 2003, Dev. 130:6411; Hambleton et al., 2004, Structure 12:2173). Unexpectedly, antibodies that bind outside the ligand binding domain of the extracellular domain of human Notch receptor have been found to inhibit tumor cell growth in vivo (see U.S. Patent Publication No. 2008/0131434, incorporated by reference herein in its entirety). Thus, antibodies that bind outside the ligand binding domain of the extracellular domain of one or more of the human Notch receptors—Notch1, Notch2, Notch3, and Notch4—have value as potential cancer therapeutics.

Monoclonal antibodies that specifically bind to the membrane proximal region of the extracellular domain of a Notch1, including the monoclonal antibody 52M51, have now been identified (Example 1). Humanized 52M51 antibodies have also been generated (Example 2). Several of the antibodies, including 52M51 and a humanized variant of 52M51, inhibit ligand-induced Notch1 signaling (Example 3 and FIGS. 1B and C), despite binding to Notch1 in a region outside of the ligand-binding region. The ability of several of the antibodies to inhibit formation of the Notch intracellular domain (ICD) has also now been demonstrated (Example 3 and FIG. 1D). 52M51 has been found to inhibit tumor cell growth in vivo in a xenograft model (Example 5 and FIGS. 2A and B). In addition, another antibody 52R43 has been found to inhibit tumor cell growth in vivo in multiple xenograft models (Example 7 and FIG. 3A-D).

Definitions

An "antagonist" of a Notch receptor as used herein is a term that includes any molecule that partially or fully blocks, inhibits, or neutralizes a biological activity of the Notch pathway. Suitable antagonist molecules specifically include antagonist antibodies or antibody fragments. The term "antagonist" is used herein to include any molecule that partially or fully blocks, inhibits, or neutralizes the expression of a Notch receptor.

The term "antibody" is used to mean an immunoglobulin molecule that recognizes and specifically binds to a target, such as a protein, polypeptide, peptide, carbohydrate, polynucleotide, lipid, or combinations of the foregoing etc., through at least one antigen recognition site within the variable region of the immunoglobulin molecule. As used herein, the term encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, monovalent or monospecific antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

As used herein, the term "antibody fragment" refers to a portion of an intact antibody and refers to the antigenic determining variable regions of an intact antibody. Examples of antibody fragments include, but are not limited to Fab, Fab', F(ab')2, and Fv fragments, linear antibodies, single chain antibodies, and multispecific antibodies formed from antibody fragments.

An "Fv antibody" refers to the minimal antibody fragment that contains a complete antigen-recognition and -binding site either as two-chains, in which one heavy and one light chain variable domain form a non-covalent dimer, or as a single-chain (scFv), in which one heavy and one light chain variable domain are covalently linked by a flexible peptide linker so that the two chains associate in a similar dimeric structure. In this configuration the complementary determining regions (CDRs) of each variable domain interact to define the antigen-binding specificity of the Fv dimer. Alternatively a single variable domain (or half of an Fv) can be used to recognize and bind antigen, although generally with lower affinity.

A "monoclonal antibody" as used herein refers to homogenous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (e.g., Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

As used herein, the term "humanized antibody" refers to forms of non-human (e.g., murine) antibodies that are specific immunoglobulin chains, chimeric immunoglobulins, or fragments thereof that contain minimal non-human sequences. Typically, humanized antibodies are human immunoglobulins in which residues from the complementary determining regions (CDRs) are replaced by residues from a CDR of a non-human species (e.g., mouse., rat, rabbit, hamster, etc.) that have the desired specificity, affinity, and/or capability. In some instances, the Fv framework region (FR) residues of a human immunoglobulin are replaced with the corresponding residues in an antibody from a non-human species that has the desired specificity, affinity, and/or capability. The humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all, or substantially all, of the CDR regions that correspond to the non-human immunoglobulin whereas all, or substantially all, of the FR regions are those of a human immunoglobulin consensus sequence. The humanized antibody can also comprise at least a portion of an immunoglobulin constant region or domain (Fc), typically that of a human immunoglobulin. Examples of methods used to generate humanized antibodies are described in U.S. Pat. No. 5,225,539, herein incorporated by reference.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. Sequences of Proteins of Immunological Interest, 5th ed., 1991, National Institutes of Health, Bethesda, Md.); and (2) an approach based on crystallographic studies of antigen-antibody complexes (Al-lazikani et al., 1997, $J.$ $Molec.$ $Biol.$ 273:927-948). In addition, combinations of these two approaches are sometimes used in the art to determine CDRs.

The term "human antibody" as used herein means an antibody produced by a human or an antibody having an amino acid sequence corresponding to an antibody produced by a human made using any of the techniques known in the art. This definition of a human antibody includes intact or full-length antibodies, fragments thereof, and/or antibodies comprising at least one human heavy and/or light chain polypeptide such as, for example, an antibody comprising murine light chain and human heavy chain polypeptides.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and/or capability, while the constant regions are homologous to the sequences in antibodies derived from another species (usually human) to avoid eliciting an immune response in that species. The term chimeric antibody includes monovalent, divalent and polyvalent antibodies.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids (also referred to as linear epitopes) are typically retained upon protein denaturing, whereas epitopes formed by tertiary folding (also referred to as conformational epitopes) are typically lost upon protein denaturing. An epitope typically includes at least 3, and more usually, at least 5 or 8-10 amino acids in a unique spatial conformation.

That an antibody "selectively binds" or "specifically binds" to an epitope or receptor means that the antibody reacts or associates more frequently, more rapidly, with greater duration, with greater affinity, or with some combination of the above to the epitope or receptor than with alternative substances, including unrelated proteins. "Selectively binds" or "specifically binds" means, for instance, that an antibody binds to a protein with a $K_D$ of about 0.1 mM or less, at times about 1 µM or less, at times about 0.1 µM or less and at times about 0.01 µM or less. Because of the sequence identity between homologous proteins in different species, specific binding can include an antibody that recognizes a Notch receptor in more than one species. It is understood that, in certain embodiments, an antibody or binding moiety that specifically binds to a first target may or may not specifically bind to a second target. As such, "specific binding" does not necessarily require (although it can include) exclusive binding, i.e. binding to a single target. Generally, but not necessarily, reference to binding means specific binding.

Competition between antibodies is determined by an assay in which the immunoglobulin under study inhibits specific binding of a reference antibody to a common antigen. Numerous types of competitive binding assays are known, for example: solid phase direct or indirect radioimmunoassay (RIA), solid phase direct or indirect enzyme immunoassay (EIA), sandwich competition assay (see Stahli et al., *Methods in Enzymology* 9:242-253 (1983)); solid phase direct biotin-avidin EIA (see Kirkland et al., *J. Immmunol.* 137:3614-3619 (1986)); solid phase direct labeled assay, solid phase direct labeled sandwich assay (see Harlow and Lane, "Antibodies, A Laboratory Manual," Cold Spring Harbor Press (1988)); solid phase direct label RIA using $^{125}$I label (see Morel et al., *Molec. Immunol.* 25(1):7-15 (1988)); solid phase direct biotin-avidin EIA (Cheung et al., *Virology* 176:546-552 (1990)); and direct labeled RIA (Moldenhauer et al., *Scand. J. Immunol.* 32:77-82 (1990)). Typically, such an assay involves the use of purified antigen bound to a solid surface or cells bearing either of these, an unlabeled test immunoglobulin and a labeled reference immunoglobulin. Competitive inhibition is measured by determining the amount of label bound to the solid surface or cells in the presence of the test immunoglobulin. Usually the test immunoglobulin is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur. Usually, when a competing antibody is present in excess, it will inhibit specific binding of a reference antibody to a common antigen by at least 50 or 75%.

The terms "isolated" or "purified" refer to material that is substantially or essentially free from components that normally accompany it in its native state. Purity and homogeneity are typically determined using analytical chemistry techniques such as polyacrylamide gel electrophoresis or high performance liquid chromatography. A protein (e.g., an antibody) or nucleic acid that is the predominant species present in a preparation is substantially purified. In particular, in some embodiments, an isolated nucleic acid comprising a gene is separated from open reading frames that naturally flank the gene and encode proteins other than the protein encoded by the gene. An isolated antibody is separated from other non-immunoglobulin proteins and from other immunoglobulin proteins with different antigen binding specificities. It can also mean that the nucleic acid or protein is at least 85% pure, at least 95% pure, and in some embodiments, at least 99% pure.

As used herein, the terms "cancer" and "cancerous" refer to or describe the physiological condition in mammals in which a population of cells are characterized by unregulated cell growth. Examples of cancer include, but are not limited to, carcinoma, lymphoma, blastoma, sarcoma, and leukemia. More particular examples of such cancers include, but are not limited to, squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Tumor" and "neoplasm" as used herein refer to any mass of tissue that result from excessive cell growth or proliferation, either benign (noncancerous) or malignant (cancerous) including pre-cancerous lesions.

The terms "proliferative disorder" and "proliferative disease" refer to disorders associated with abnormal cell proliferation such as cancer.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

The terms "cancer stem cell" or "tumor stem cell" or "solid tumor stem cell" are used interchangeably herein and refer to a population of cells from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. These properties of "cancer stem cells" or "tumor stem cells" or "solid tumor stem cells" confer on those cancer stem cells the ability to form palpable tumors upon serial transplantation into an immunocompromised mouse compared to the majority of tumor cells that fail to form tumors. Cancer stem cells undergo self-renewal versus differentiation in a chaotic manner to form tumors with abnormal cell types that can change over time as mutations occur.

The terms "cancer cell" or "tumor cell" refer to the total population of cells derived from a tumor including both non-tumorigenic cells, which comprise the bulk of the tumor cell population, and tumorigenic stem cells (cancer stem cells).

As used herein "tumorigenic" refers to the functional features of a solid tumor stem cell including the properties of self-renewal (giving rise to additional tumorigenic cancer stem cells) and proliferation to generate all other tumor cells (giving rise to differentiated and thus non-tumorigenic tumor cells) that allow solid tumor stem cells to form a tumor.

As used herein, the "tumorigenicity" of a tumor refers to the ability of a random sample of cells from the tumor to form palpable tumors upon serial transplantation into immuno-compromised mice.

As used herein, the terms "stem cell cancer marker" or "cancer stem cell marker" or "tumor stem cell marker" or "solid tumor stem cell marker" refer to a gene or genes or a protein, polypeptide, or peptide expressed by the gene or genes whose expression level, alone or in combination with other genes, is correlated with the presence of tumorigenic cancer cells compared to non-tumorigenic cells. The correlation can relate to either an increased or decreased expression of the gene (e.g., increased or decreased levels of mRNA or the peptide encoded by the gene).

The terms "cancer stem cell gene signature" or "tumor stem cell gene signature" or "cancer stem cell signature" are used interchangeably herein to refer to gene signatures comprising genes differentially expressed in cancer stem cells compared to other cells or population of cells, for example normal breast epithelial tissue. In some embodiments the cancer stem cell gene signatures comprise genes differentially expressed in cancer stem cells versus normal breast epithelium by a fold change, for example by 2 fold reduced and/or elevated expression, and further limited by using a statistical analysis such as, for example, by the P value of a t-test across multiple samples. In another embodiment, the genes differentially expressed in cancer stem cells are divided into cancer stem cell gene signatures based on the correlation of their expression with a chosen gene in combination with their fold or percentage expression change. Cancer stem cell signatures are predictive both retrospectively and prospectively of an aspect of clinical variability, including but not limited to, metastasis and death.

The term "genetic test" as used herein refers to procedures whereby the genetic make-up of a patient or a patient tumor sample is analyzed. The analysis can include detection of DNA, RNA, chromosomes, proteins or metabolites to detect heritable or somatic disease-related genotypes or karyotypes for clinical purposes.

As used herein, the terms "biopsy" or "biopsy tissue" refer to a sample of tissue or fluid that is removed from a subject for the purpose of determining if the sample contains cancerous tissue. In some embodiments, biopsy tissue or fluid is obtained because a subject is suspected of having cancer. The biopsy tissue or fluid is then examined for the presence or absence of cancer.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

"Pharmaceutically acceptable" refers to approved or approvable by a regulatory agency of the Federal or a state government or listed in the U.S. Pharmacopeia or other generally recognized pharmacopeia for use in animals, including humans.

"Pharmaceutically acceptable excipient, carrier or adjuvant" or "acceptable pharmaceutical carrier" refers to an excipient, carrier or adjuvant that can be administered to a subject, together with at least one antibody of the present disclosure, and which does not destroy the pharmacological activity thereof and is nontoxic when administered in doses sufficient to deliver a therapeutic amount of the antibody. In addition, a "pharmaceutically acceptable carrier" does not trigger an immune response in a recipient subject. Examples include, but are not limited to, any of the standard pharmaceutical carriers such as a phosphate buffered saline solution, water, and various oil/water emulsions. Some diluents for aerosol or parenteral administration are phosphate buffered saline or normal (0.9%) saline.

"Pharmaceutically acceptable vehicle" refers to a diluents, adjuvant, excipient, or carrier with which at least one antibody of the present disclosure is administered.

The term "effective amount" or "therapeutically effective amount" or "therapeutic effect" refers to an amount of an antibody, polypeptide, polynucleotide, small organic molecule, or other drug effective to "treat" a disease or disorder in a subject or mammal. In the case of cancer, the therapeutically effective amount of the drug has a therapeutic effect and as such can reduce the number of cancer cells; decrease tumorigenicity, tumorigenic frequency or tumorigenic capacity; reduce the number or frequency of cancer stem cells; reduce the tumor size; inhibit or stop cancer cell infiltration into peripheral organs including, for example, the spread of cancer into soft tissue and bone; inhibit and stop tumor metastasis; inhibit and stop tumor growth; relieve to some extent one or more of the symptoms associated with the cancer; reduce morbidity and mortality; improve quality of life; or a combination of such effects. To the extent the agent, for example an antibody, prevents growth and/or kills existing cancer cells, it can be referred to as cytostatic and/or cytotoxic.

Terms such as "treating" or "treatment" or "to treat" or "alleviating" or "to alleviate" refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; improvement in quality of life; reduction in tumorigenicity; reduction in the number or frequency of cancer stem cells; or some combination of effects.

As used herein, the terms "polynucleotide" or "nucleic acid" refer to a polymer composed of a multiplicity of nucleotide units (ribonucleotide or deoxyribonucleotide or related structural variants) linked via phosphodiester bonds, including but not limited to, DNA or RNA. The term encompasses sequences that include any of the known base analogs of DNA and RNA.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activities or functional properties (e.g., enzymatic activity, ligand binding, signal transduction, immunogenicity, etc.) of the full-length polypeptide or fragment are retained. The term also encompasses the coding region of a structural gene and the sequences located adjacent to the coding region on both the 5' and 3' ends for a distance of about 1 kb or more on either end such that the gene corresponds to the length of the full-length mRNA. The term "gene" encompasses both cDNA and genomic forms of a gene.

The term "recombinant" when used with reference to a cell, nucleic acid, protein or vector indicates that the cell, nucleic acid, protein or vector has been modified by the introduction of a heterologous nucleic acid or protein, the alteration of a native nucleic acid or protein, or that the cell is derived from a cell so modified. Thus, e.g., recombinant cells express genes that are not found within the native (non-recombinant) form of the cell or express native genes that are overexpressed or otherwise abnormally expressed such as, for example, expressed as non-naturally occurring fragments or splice variants. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus an isolated nucleic acid, in a linear form, or an expression vector formed in vitro by ligating DNA molecules that are not normally joined, are both considered recombinant for the purposes of this invention. It is understood that once a recombinant nucleic acid is made and introduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

As used herein, the term "vector" is used in reference to nucleic acid molecules that transfer DNA segment(s) from one cell to another. Vectors are often derived from plasmids, bacteriophages, or plant or animal viruses.

As used herein, the term "gene expression" refers to the process of converting genetic information encoded in a gene into RNA (e.g., mRNA, rRNA, tRNA, or snRNA) through "transcription" of the gene (e.g., via the enzymatic action of an RNA polymerase), and for protein encoding genes, into protein through "translation" of mRNA. Gene expression can be regulated at many stages in the process. "Up-regulation" or "activation" refers to regulation that increases the production of gene expression products (e.g., RNA or protein), while "down-regulation" or "repression" refers to regulation that decrease production. Molecules (e.g., transcription factors) that are involved in up-regulation or down-regulation are often called "activators" and "repressors," respectively.

The terms "polypeptide" or "peptide" or "protein" or "protein fragment" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymers.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, gamma-carboxyglutamate, and O-phosphoserine. "Amino acid analogs" refers to compounds that have the same basic chemical structure as a naturally occurring amino acid, e.g., an alpha carbon that is bound to a hydrogen, a carboxyl group, an amino group, and an R group, e.g., homoserine, norleucine, methionine sulfoxide, methionine methyl sulfonium. Such analogs can have modified R groups (e.g., norleucine) or modified peptide backbones, but retain the same basic chemical structure as a naturally occurring amino acid. "Amino acid mimetics" refers to chemical compounds that have a structure that is different from the general chemical structure of an amino acid, but that functions similarly to a naturally occurring amino acid.

"Conservatively modified variants" applies to both amino acid and nucleic acid sequences. "Amino acid variants" refers to amino acid sequences. With respect to particular nucleic acid sequences, conservatively modified variants refers to those nucleic acids which encode identical or essentially identical amino acid sequences, or where the nucleic acid does not encode an amino acid sequence, to essentially identical or associated (e.g., naturally contiguous) sequences. Because of the degeneracy of the genetic code, a large number of functionally identical nucleic acids encode most proteins. For instance, the codons GCA, GCC, GCG and GCU all encode the amino acid alanine. Thus, at every position where an alanine is specified by a codon, the codon can be altered to another of the corresponding codons described without altering the encoded polypeptide. Such nucleic acid variations are "silent variations," which are one species of conservatively modified variations. Every nucleic acid sequence herein which encodes a polypeptide also describes silent variations of the nucleic acid. It is recognized that in certain contexts each codon in a nucleic acid (except AUG, which is ordinarily the only codon for methionine, and TGG, which is ordinarily the only codon for tryptophan) can be modified to yield a functionally identical molecule. Accordingly, silent variations of a nucleic acid which encodes a polypeptide is implicit in a described sequence with respect to the expression product, but not with respect to actual probe sequences.

As to amino acid sequences, it will be recognized that individual substitutions, deletions or additions to a nucleic acid, peptide, polypeptide, or protein sequence which alters, adds or deletes a single amino acid or a small percentage of amino acids in the encoded sequence is a "conservatively modified variant" including where the alteration results in the substitution of an amino acid with a chemically similar amino acid. Conservative substitution tables providing functionally similar amino acids are well known in the art. (See, for example, Table 1). Guidance concerning which amino acid changes are likely to be phenotypically silent can also be found in Bowie et al., 1990, Science 247:1306 1310. Such conservatively modified variants are in addition to and do not exclude polymorphic variants, interspecies homologs, and alleles of the invention. Typically conservative substitutions include: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, Proteins (1984)). As indicated, changes are typically of a minor nature, such as conservative amino acid substitutions that do not significantly affect the folding or activity of the protein.

TABLE 1

Conservative Amino Acid Substitutions

| Original Amino Acid | Exemplary Conservative Substitutions |
|---|---|
| Alanine | Valine, Isoleucine, Leucine, Glycine, Serine |
| Arginine | Lysine, Histidine, Glutamine, Asparagine |
| Asparagine | Glutamine, Histidine, Lysine, Arginine |
| Aspartic Acid | Glutamic Acid, Asparagine |
| Cysteine | Serine, Alanine, Methionine |
| Glutamine | Asparagine |
| Glutamic Acid | Aspartic Acid, Glutamine |
| Glycine | Proline, Alanine |
| Histidine | Asparagine, Glutamine, Lysine, Arginine |
| Isoleucine | Leucine, Valine, Methionine, Alanine, Phenylalanine, Norleucine |
| Leucine | Norleucine, Isoleucine, Valine, Methionine, Alanine, Phenylalanine |
| Lysine | Arginine, Glutamine, Asparagine, Histidine |
| Methionine | Leucine, Phenylalanine, Isoleucine, Valine, Cysteine |
| Phenylalanine | Leucine, Valine, Isoleucine, Alanine, Tyrosine |
| Proline | Alanine, Glycine |
| Serine | Threonine |
| Threonine | Serine |
| Trytophan | Tyrosine, Phenylalanine |
| Tyrosine | Tryptophan, Phenylalanine, Threonine, Serine |
| Valine | Isoleucine, Methionine, Leucine, Phenylalanine, Alanine, Norleucine |

As used in the present disclosure and claims, the singular forms "a", "an", and "the" include plural forms unless the context clearly dictates otherwise.

It is understood that whenever embodiments are described herein with the language "comprising" otherwise analogous embodiments described in terms of "consisting" and/or "consisting essentially of" are also provided.

Certain Embodiments of the Present Invention

The present invention provides compositions and methods for studying, diagnosing, characterizing, and treating cancer.

In particular, in certain embodiments, the present invention provides agents, including antagonists, that bind Notch receptors and methods of using the agents or antagonists to inhibit tumor growth and treat cancer or other diseases in human patients. In certain embodiments, the antagonists are antibodies that specifically bind to a non-ligand binding region of the extracellular domain of a human Notch receptor.

In one aspect, the present invention provides an antibody that specifically binds to a non-ligand binding membrane proximal region of the extracellular domain of a human Notch1 receptor. In some embodiments, the antibody binds a region of human Notch1 comprising about amino acid 1427 to about amino acid 1732. In some embodiments, the antibody binds to a region comprising SEQ ID NO:2. In certain embodiments, the antibody that specifically binds to a non-ligand binding membrane proximal region of the extracellular domain of at least one additional Notch receptor.

In some embodiments, the antibody is an antagonist of human Notch1. In certain embodiments, the antibody inhibits ligand-induced signaling of a Notch1 pathway. In some embodiments, the antibody inhibits the activity of Notch1. In other embodiments the antibody inhibits cleavage of a Notch1 receptor. In some embodiments, the antibody inhibits cleavage of Notch1 at a site within the membrane proximal region of the extracellular domain. In certain embodiments, the antibody inhibits release or formation of the intracellular domain (ICD) of Notch1. In other embodiments, the antibody reduces the tumorigenicity of a tumor that comprises cancer stem cells. In certain embodiments, the antibody inhibits the growth of a tumor comprising cancer stem cells. In certain embodiments, the antibody inhibits the growth of a tumor.

In certain embodiments, the antibody that specifically binds to a membrane proximal region of the extracellular domain of a human Notch1 receptor and inhibits tumor growth is a monoclonal antibody. In certain embodiments, the antibody that specifically binds to a membrane proximal region of the extracellular domain of a human Notch1 receptor is a chimeric antibody, is a humanized antibody, is a human antibody, is an antibody fragment, or is a bispecific antibody. In certain embodiments, the present invention provides a hybridoma producing an antibody that specifically binds to a non-ligand binding membrane proximal region of the extracellular domain of a human Notch1 receptor and inhibits tumor growth.

In another aspect, the invention provides a method of inhibiting the growth of a tumor in a subject, the method comprising administering to the subject a therapeutically effective amount of an antibody that specifically binds to a non-ligand binding membrane proximal region of the extracellular domain of a human Notch1 receptor protein. In some embodiments, the tumor comprises cancer stem cells. In some embodiments, the methods comprise targeting the cancer stem cells with the antibodies. In certain embodiments, the method of inhibiting growth of a tumor comprises administering a therapeutically effective amount of a monoclonal antibody. In certain embodiments, the method of inhibiting growth of a tumor comprises administering a therapeutically effective amount of a chimeric antibody. In certain embodiments, the method of inhibiting growth of a tumor comprises administering a therapeutically effective amount of a humanized antibody. In certain embodiments, the method of inhibiting growth of a tumor comprises administering a therapeutically effective amount of a human antibody.

In certain embodiments, the method of inhibiting growth of a tumor comprises reducing the frequency of cancer stem cells in the tumor, reducing the number of cancer stem cells in the tumor, reducing the tumorigenicity of the tumor, and/or reducing the tumorigenicity of the tumor by reducing the number or frequency of cancer stem cells in the tumor. In some embodiments, the method of inhibiting growth of a tumor comprises inhibiting the activity of a Notch1 receptor. In certain embodiments, the tumor includes, but is not limited to, a breast tumor, colorectal tumor, hepatic tumor, renal tumor, lung tumor, pancreatic tumor, ovarian tumor, prostate tumor and head and neck tumor.

In another aspect, the present invention provides a method of treating cancer in a subject in need thereof comprising administering to a subject a therapeutically effective amount of an antibody that specifically binds to a non-ligand binding membrane proximal region of the extracellular domain of a human Notch1 receptor protein and inhibits tumor growth in the subject. In certain embodiments, the method of treating cancer comprises administering a therapeutically effective amount of a monoclonal antibody. In certain embodiments, the method of treating cancer comprises administering a therapeutically effective amount of a chimeric antibody. In certain embodiments, the method of treating cancer comprises administering a therapeutically effective amount of a humanized antibody. In certain embodiments, the method of treating cancer comprises administering a therapeutically effective amount of a human antibody.

In certain embodiments, the method of treating cancer comprises administering a therapeutically effective amount of an antibody conjugated to a cytotoxic moiety that specifically binds to a non-ligand binding membrane proximal region of the extracellular domain of a human Notch1 receptor and inhibits tumor growth. In certain embodiments, the method of treating cancer comprises administering a therapeutically effective amount of an antibody of any of the aspects and/or embodiments, as well as other aspects and/or embodiments described herein, in combination with radiation therapy. In certain embodiments, the method of treating cancer comprises administering a therapeutically effective amount of an antibody of any of the aspects and/or embodiments, as well as other aspects and/or embodiments described herein, in combination with chemotherapy. In certain embodiments, the method of treating cancer comprises administering a therapeutically effective amount of an antibody that specifically binds to a non-ligand binding membrane proximal region of the extracellular domain of a human Notch1 receptor and inhibits tumor growth that are from tumors including, but not limited to, a breast tumor, colorectal tumor, lung tumor, pancreatic tumor, prostate tumor, or a head and neck tumor.

In certain embodiments, the method of treating cancer comprises identifying patients in need of treatment using a genetic test comprising an antibody that specifically binds to a non-ligand binding membrane proximal region of the extracellular domain of a human Notch1 receptor; and administering a therapeutically effective amount of the antibody to the patients. In certain embodiments, the method of treating cancer comprises identifying patients in need of treatment with an antibody that specifically binds to a non-ligand binding membrane proximal region of the extracellular domain of a human Notch1 receptor using a genetic test that detects a cancer stem cell signature, and administering a therapeutically effective amount of the antibody that specifically binds to a non-ligand binding membrane proximal region of the extracellular domain of a human Notch1 receptor and inhibits tumor growth.

In another aspect, the present invention provides a method of identifying a molecule that binds to a non-ligand binding membrane proximal region of the extracellular domain of a human Notch1 receptor and inhibits tumor growth, the method comprising: i) incubating the molecule with a non-ligand binding membrane proximal region of the extracellular domain of a human Notch1 receptor; ii) determining if the molecule binds to the non-ligand binding membrane proximal region of the extracellular domain of the human Notch1 receptor; and iii) determining if the molecule inhibits tumor growth. In certain embodiments, the invention provides a method of identifying a molecule that binds to a non-ligand binding membrane proximal region of an extracellular domain of a human Notch1 receptor and inhibits tumor growth, the method comprising: i) incubating the molecule with the non-ligand binding membrane proximal region of the extracellular domain of a human Notch1 receptor comprising SEQ ID NO:2; ii) determining if the molecule binds to the non-ligand binding membrane proximal region of the extracellular domain of the human Notch1 receptor comprising SEQ ID NO:2; and iii) determining if the molecule inhibits tumor growth.

In certain embodiments, the present invention provides a pharmaceutical composition comprising an antibody that specifically binds to a non-ligand binding membrane proximal region of the extracellular domain of a human Notch1 receptor and inhibits tumor growth.

In certain embodiments, the present invention provides a method of making an antibody that specifically binds to a non-ligand binding membrane proximal region of the extracellular domain of a human Notch1 receptor and inhibits tumor growth.

In certain embodiments, the present invention provides an isolated nucleic acid that encodes an antibody that specifically binds to a non-ligand membrane proximal binding region of the extracellular domain of a human Notch1 receptor and inhibits tumor growth.

In certain embodiments, antagonists against a Notch receptor, such as Notch1, act extracellularly to act upon or inhibit the function of the Notch receptor. In certain embodiments, an antagonist of a Notch receptor is proteinaceous. In some embodiments, proteinaceous antagonists of a Notch1 receptor are antibodies that specifically bind to an extracellular epitope of a Notch1 receptor. Extracellular binding of an antagonist against a Notch1 receptor can inhibit the signaling of a Notch receptor by inhibiting intrinsic activation (e.g. kinase activity) of a Notch1 receptor and/or by sterically inhibiting the interaction, for example, of a Notch receptor with one of its ligands. Furthermore, extracellular binding of an antagonist to a Notch receptor can downregulate cell-surface expression of a Notch receptor such as, for example, by internalization of a Notch receptor and/or decreasing cell surface trafficking of a Notch receptor. Extracellular binding of an antagonist to a Notch receptor can inhibit cleavage of the Notch receptor and reduce release of the LCD of Notch.

In some embodiments, antagonists against a Notch receptor bind to a Notch receptor and have one or more of the following effects: inhibit proliferation of tumor cells, trigger cell death directly in tumor cells, or prevent metastasis of tumor cells. In certain embodiments, antagonists of a Notch receptor trigger cell death via a conjugated toxin, chemotherapeutic agent, radioisotope, or other such agent. For example, an antibody against a Notch receptor is conjugated to a toxin that is activated in tumor cells expressing the Notch receptor by protein internalization. In other embodiments, antagonists of a Notch receptor mediate cell death of a cell expressing the Notch receptor via antibody-dependent cellular cytotoxicity (ADCC). ADCC involves cell lysis by effector cells that recognize the Fc portion of an antibody. Many lymphocytes, monocytes, tissue macrophages, granulocytes and eosinophils, for example, have Fc receptors and can mediate cytolysis (Dillman, 1994, *J. Clin. Oncol.* 12:1497).

In some embodiments, an antagonist of a Notch receptor is an antibody that triggers cell death of cell expressing a Notch receptor by activating complement-dependent cytotoxicity (CDC). CDC involves binding of serum complement to the Fc portion of an antibody and subsequent activation of the complement protein cascade, resulting in cell membrane damage and eventual cell death. Biological activity of antibodies is known to be determined, to a large extent, by the constant domains or Fc region of the antibody molecule (Uananue and Benacerraf, Textbook of Immunology, 2nd Edition, Williams & Wilkins, p. 218 (1984)). Antibodies of different classes and subclasses differ in this respect, as do antibodies of the same subclass but from different species. Of human antibodies, IgM is the most efficient class of antibodies to bind complement, followed by IgG1, IgG3, and IgG2 whereas IgG4 appears quite deficient in activating the complement cascade (Dillman, 1994, *J. Clin. Oncol.* 12:1497; Jefferis et al., 1998, *Immunol. Rev.* 163:59-76). According to the present invention, antibodies of those classes having the desired biological activity are prepared.

The ability of any particular antibody against a Notch receptor to mediate lysis of the target cell by complement activation and/or ADCC can be assayed. The cells of interest are grown and labeled in vitro; the antibody is added to the cell culture in combination with either serum complement or immune cells which can be activated by the antigen antibody complexes. Cytolysis of the target cells is detected, for example, by the release of label from the lysed cells. In fact, antibodies can be screened using the patient's own serum as a source of complement and/or immune cells. The antibody that is capable of activating complement or mediating ADCC in the in vitro test can then be used therapeutically in that particular patient.

In certain embodiments, the Notch-binding agent or antagonist is an antibody that does not have one or more effector functions. For instance, in some embodiments, the antibody has no antibody-dependent cellular cytotoxicity (ADCC) activity, and/or no complement-dependent cytoxicity (CDC) activity. In certain embodiments, the antibody does not bind to the Fc receptor and/or complement factors. In certain embodiments, the antibody has no effector function.

In other embodiments, antagonists of a Notch receptor can trigger cell death indirectly by inhibiting angiogenesis. Angiogenesis is the process by which new blood vessels form from pre-existing vessels and is a fundamental process required for normal growth, for example, during embryonic development, wound healing and in response to ovulation. Solid tumor growth larger than 1-2 $mm^2$ also requires angiogenesis to supply nutrients and oxygen without which tumor cells die. Thus in certain embodiments, an antagonist of a Notch receptor targets vascular cells that express the Notch receptor including, for example, endothelial cells, smooth muscle cells or components of the extracellular matrix required for vascular assembly. In other embodiments, an antagonist of a Notch receptor inhibits growth factor signaling required by vascular cell recruitment, assembly, maintenance or survival.

The present invention provides a variety of polypeptides, including but not limited to antibodies and fragments of antibodies. In certain embodiments, the polypeptide is isolated. In certain alternative embodiments, the polypeptide is substantially pure.

In certain embodiments, the polypeptides of the present invention can be recombinant polypeptides, natural polypeptides, or synthetic polypeptides comprising the sequence of SEQ ID NO:8, SEQ ID NO:14, SEQ ID NO:24, SEQ ID NO:28, or SEQ ID NO:32 (with or without the indicated signal sequences).

The invention provides a polypeptide comprising the heavy chain and/or the light chain provided in SEQ ID NO:10 and/or SEQ ID NO:4, respectively (with or without the indicated putative signal sequences). In certain embodiments, the polypeptide is an antibody. In certain embodiments, the polypeptide specifically binds a non-ligand binding membrane proximal region of the extracellular domain of a human Notch1 receptor.

The invention further provides a polypeptide comprising SEQ ID NO:8, SEQ ID NO:28 or SEQ ID NO:32, and/or SEQ ID NO:14 or SEQ ID NO:24. In certain embodiments, the polypeptide comprises a variable light chain sequence comprising SEQ ID NO:8 and a variable heavy chain sequence comprising SEQ ID NO:14. In certain embodiments, the polypeptide comprises a variable light chain sequence comprising SEQ ID NO:28 and a variable heavy chain sequence comprising SEQ ID NO:24. In certain embodiments, the polypeptide comprises a variable light chain sequence comprising SEQ ID NO:32 and a variable heavy chain sequence comprising SEQ ID NO:24. In certain embodiments, the polypeptide is an antibody. In certain embodiments, the polypeptide specifically binds a non-ligand binding membrane proximal region of the extracellular domain of a human Notch1 receptor.

It will be recognized in the art that some amino acid sequences of the invention can be varied without significant effect of the structure or function of the protein. If such differences in sequence are contemplated, it should be remembered that there will be critical areas on the protein which determine activity. Thus, the invention further includes variations of the polypeptides which show substantial activity. Such mutants include deletions, insertions, inversions, repeats, and type substitutions. Guidance concerning which amino acid changes are likely to be phenotypically silent can be found in Bowie, J. U., et al., "Deciphering the Message in Protein Sequences: Tolerance to Amino Acid Substitutions," *Science* 1990, 247:1306-1310.

Thus, the fragments, derivatives, or analogs of the polypeptides of the invention can be: (i) one in which one or more of the amino acid residues are substituted with a conserved or non-conserved amino acid residue (often a conserved amino acid residue) and such substituted amino acid residue can or cannot be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives, and analogs are deemed to be within the scope of the teachings herein.

Of particular interest are substitutions of charged amino acids with another charged amino acid and with neutral or negatively charged amino acids. The latter results in proteins with reduced positive charge. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol.* 1967, 2:331-340; Robbins et al., *Diabetes* 1987, 36:838-845; Cleland et al. *Crit. Rev. Therapeutic Drug Carrier Systems* 1993, 10:307-377).

Of course, the number of amino acid substitutions made depends on many factors, including those described herein. In certain embodiments, the number of substitutions for any given polypeptide will not be more than 50, 40, 30, 25, 20, 15, 10 or 3.

The polypeptides of the present invention include the polypeptides of SEQ ID NO:14 as well as polypeptides which have at least 90% similarity (at certain times at least 90% sequence identity) to the polypeptides of SEQ ID NO:14 and at least 95% similarity (at certain times at least 95% sequence identity) to the polypeptides of SEQ ID NOs:14, and in still other embodiments, polypeptide which have at least 96%, 97%, 98%, or 99% similarity (at certain times 96%, 97%, 98%, or 99% sequence identity) to the polypeptides of SEQ ID NOs:14. The polypeptides of the present invention include the polypeptides of SEQ ID NO:8 as well as polypeptides which have at least 90% similarity (at certain times at least 90% sequence identity) to the polypeptides of SEQ ID NO:8 and at least 95% similarity (at certain times at least 95% sequence identity) to the polypeptides of SEQ ID NOs:8, and in still other embodiments, polypeptide which have at least 96%, 97%, 98%, or 99% similarity (at certain times 96%, 97%, 98%, or 99% sequence identity) to the polypeptides of SEQ ID NOs:8. As known in the art "similarity" between two polypeptides is determined by comparing the amino acid sequence and its conserved amino acid substitutes of one polypeptide to the sequence of a second polypeptide.

Fragments or portions of the polypeptides of the present invention can be employed for producing the corresponding full-length polypeptide by peptide synthesis; therefore, the fragments can be employed as intermediates for producing the full-length polypeptides. Fragments or portions of the polynucleotides of the present invention can be used to synthesize full-length polynucleotides of the present invention.

In certain embodiments, a fragment of the proteins of this invention is a portion or all of a protein which is capable of binding to a Notch1 receptor protein. This fragment has a high affinity for a Notch receptor or a ligand of a Notch1 receptor. Certain fragments of fusion proteins are protein fragments comprising at least part of the Notch binding domain of the polypeptide agent or antagonist fused to at least part of a constant region of an immunoglobulin. The affinity is typically in the range of about $10^{-11}$ to $10^{-12}$ M, although the affinity can vary considerably with fragments of different sizes, ranging from $10^{-7}$ to $10^{-13}$ M. In some embodiments, the fragment is about 10-110 amino acids in length and comprises the Notch binding domain of the polypeptide agent or antagonist linked to at least part of a constant region of an immunoglobulin.

The polypeptides and analogs can be further modified to contain additional chemical moieties not normally part of the protein. The derivatized moieties can improve the solubility, the biological half life and/or absorption of the protein. The moieties can also reduce or eliminate any undesirable side effects of the protein and the like. An overview for chemical moieties can be found in Remington's Pharmaceutical Sciences, 20th ed., Mack Publishing Co., Easton, Pa. (2000).

The isolated polypeptides described herein can be produced by any suitable method known in the art. Such methods range from direct protein synthesis methods to constructing a DNA sequence encoding isolated polypeptide sequences and expressing those sequences in a suitable transformed host.

In some embodiments of a recombinant method, a DNA sequence is constructed by isolating or synthesizing a DNA sequence encoding a wild-type protein of interest. Optionally, the sequence can be mutagenized by site-specific mutagenesis to provide functional analogs thereof. See, e.g. Zoeller et al., *Proc.-Nat Acad. Sci. USA* 1984, 81:5662-5066 and U.S. Pat. No. 4,588,585. Another method of constructing a DNA sequence encoding a polypeptide of interest would be by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced.

Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis, or another method), the mutant DNA sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene is operatively linked to transcriptional and translational expression control sequences that are functional in the chosen expression host.

The present invention provides isolated antibodies against a non-ligand binding membrane proximal region of the extracellular domain of a Notch1 receptor. The antibody, or antibody fragment, can be any monoclonal or polyclonal antibody that specifically recognizes a membrane proximal region of the extracellular domain of Notch1. In some embodiments, the present invention provides monoclonal antibodies, or fragments thereof, that specifically bind to a membrane proximal region of the extracellular domain of a human Notch1 as described herein. In some embodiments, the monoclonal antibodies, or fragments thereof, are chimeric or humanized antibodies that specifically bind to a membrane proximal region of the extracellular domain of a human Notch1 receptor as described herein. In other embodiments, the monoclonal antibodies, or fragments thereof, are human antibodies that specifically bind to a membrane proximal region of the extracellular domain of a human Notch1 receptor as described herein.

The antibodies against a membrane proximal region of the extracellular domain of a Notch1 receptor find use in the experimental, diagnostic and therapeutic methods described herein. In certain embodiments, the antibodies of the present invention are used to detect the expression of a Notch1 receptor in biological samples such as, for example, a patient tissue biopsy, pleural effusion, or blood sample. Tissue biopsies can be sectioned and protein detected using, for example, immunofluorescence or immunohistochemistry. Alternatively, individual cells from a sample are isolated, and protein expression detected on fixed or live cells by FACS analysis. Furthermore, the antibodies can be used on protein arrays to detect expression of a Notch1 receptor, for example, on tumor cells, in cell lysates, or in other protein samples. In other embodiments, the antibodies of the present invention are used to inhibit the growth of tumor cells by contacting the antibodies with tumor cells either in in vitro cell based assays or in vivo animal models. In still other embodiments, the antibodies are used to treat cancer in a human patient by administering a therapeutically effective amount of an antibody against a membrane proximal region of the extracellular domain of a Notch1 receptor.

Polyclonal antibodies can be prepared by any known method. Polyclonal antibodies are raised by immunizing an animal (e.g. a rabbit, rat, mouse, goat, donkey, etc.) by multiple subcutaneous or intraperitoneal injections of the relevant antigen (a purified peptide fragment, full-length recombinant protein, fusion protein, etc.) optionally conjugated to keyhole limpet hemocyanin (KLH), serum albumin, etc. diluted in sterile saline and combined with an adjuvant (e.g., Complete or Incomplete Freund's Adjuvant) to form a stable emulsion. The polyclonal antibody is then recovered from blood, ascites and the like, of an animal so immunized. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc.

Monoclonal antibodies can be prepared using hybridoma methods, such as those described by Kohler and Milstein, 1975, *Nature* 256:495-497. Using the hybridoma method, a mouse, hamster, or other appropriate host animal, is immunized as described above to elicit the production of antibodies by lymphocytes that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay such as radioimmunoassay (RIA) or enzyme-linked immunosorbent assay (ELISA) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid as described for polyclonal antibodies above.

In some embodiments of the present invention, the antibody is an antibody that specifically binds to a non-ligand binding membrane proximal region of the extracellular domain of a human Notch1 receptor. In some embodiments, the antibody comprises a heavy chain variable region having at least 90% sequence identity to SEQ ID NO:14; and/or a light chain variable region having at least 90% sequence identity to SEQ ID NO:8. In some embodiments, the antibody comprises a heavy chain variable region having at least 95% sequence identity to SEQ ID NO:14, and/or a light chain variable region having at least 95% sequence identity to SEQ ID NO:8. In some embodiments, the antibody is a monoclonal antibody or antibody fragment.

In certain embodiments, the invention provides an antibody that binds a non-ligand binding membrane proximal region of the extracellular domain of a human Notch1 and comprises a heavy chain CDR1 comprising RGYWIE (SEQ ID NO:15), a heavy chain CDR2 comprising QILPGTGRTNYNEKFKG (SEQ ID NO:16), and/or a heavy chain CDR3 comprising FDGNYGYYAMDY (SEQ ID NO:17). In some embodiments, the antibody further comprises a light chain CDR1 comprising RSSTGAVTTSNYAN (SEQ ID NO:18), a light chain CDR2 comprising GTNNRAP (SEQ ID NO:19), and/or a light chain CDR3 comprising ALWYSNHWVFGGGTKL (SEQ ID NO:20). In some embodiments, the antibody comprises a heavy chain CDR1 comprising RGYWIE (SEQ ID NO:15), a heavy chain CDR2 comprising QILPGTGRTNYNEKFKG (SEQ ID NO:16), and/or a heavy chain CDR3 comprising FDGNYGYYAMDY (SEQ ID NO:17); and a light chain CDR1 comprising RSST-GAVTTSNYAN (SEQ ID NO:18), a light chain CDR2 comprising GTNNRAP (SEQ ID NO:19), and/or a light chain CDR3 comprising ALWYSNHWVFGGGTKL (SEQ ID NO:20). In some embodiments, the antibody comprises a heavy chain variable region comprising: (a) a heavy chain CDR1 comprising RGYWIE (SEQ ID NO:15), or a variant thereof comprising 1, 2, 3, or 4 amino acid substitutions; (b) a heavy chain CDR2 comprising QILPGTGRTNYNEKFKG (SEQ ID NO:16), or a variant thereof comprising 1, 2, 3, or 4 amino acid substitutions; and/or (c) a heavy chain CDR3 comprising FDGNYGYYAMDY (SEQ ID NO:17), or a variant thereof comprising 1, 2, 3, or 4 amino acid substitutions. In other embodiments, the antibody comprises a light chain variable region comprising: (a) a light chain CDR1 comprising RSSTGAVTTSNYAN (SEQ ID NO:18), or a variant thereof comprising 1, 2, 3, or 4 amino acid substitutions; (b) a light chain CDR2 comprising GTNNRAP(SEQ ID NO:19), or a variant thereof comprising 1, 2, 3, or 4 amino acid substitutions; and/or (c) a light chain CDR3 comprising ALWYSNHWVFGGGTKL (SEQ ID NO:20), or a variant thereof comprising 1, 2, 3, or 4 amino acid substitutions. In some embodiments, the amino acid substitutions are conservative amino acid substitutions.

In some embodiments, the invention provides an antibody, 52M51, produced by the hybridoma cell line deposited with the ATCC under the conditions of the Budapest Treaty on Aug. 7, 2008 and assigned number PTA-9405. In some embodiments, the antibody is a humanized version of 52M51. In some embodiments, the antibody is a humanized version of 52M51, "52M51H4L3", as encoded by the DNA deposited with the ATCC under the conditions of the Budapest Treaty on Oct. 15, 2008 and assigned number PTA-9549. In some embodiments, the antibody is a humanized version of 52M51, "52M51H4L4". In some embodiments, the invention provides an antibody that binds to the same epitope as the epitope to which antibody 52M51 binds. In other embodiments, the invention provides an antibody that competes with any of the antibodies as described in the aforementioned embodiments and/or aspects, as well as other aspects/embodiments described elsewhere herein, for specific binding to a non-ligand binding membrane proximal region of the extracellular domain of a human Notch1 receptor. Pharmaceutical compositions comprising the antibodies and methods of treating cancer comprising administering therapeutically effective amounts of the antibodies are also provided.

In some embodiments, the invention provides an antibody, 52R43, as encoded by the DNA deposited with the ATCC under the conditions of the Budapest Treaty on Oct. 15, 2008 and assigned number PTA-9548. In some embodiments, the invention provides an antibody that binds to the same epitope as the epitope to which antibody 52R43 binds. In some embodiments, the invention provides an antibody that comprises one, two, three, four, five and/or six of the CDRs of 52R43. In other embodiments, the invention provides an antibody that competes with 52R43. Pharmaceutical compositions comprising the antibodies and methods of treating cancer comprising administering therapeutically effective amounts of the antibodies are also provided.

Alternatively monoclonal antibodies can also be made using recombinant DNA methods as described in U.S. Pat. No. 4,816,567. Polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. Isolated polynucleotides encoding the heavy and light chains are then cloned into suitable expression vectors are then transfected into host cells such as E. coli cells, simian COS cells, Chinese hamster ovary (CHO) cells, or myeloma cells that do not otherwise produce immunoglobulin protein. Host cells are screened for monoclonal antibody production and antibodies with the desired specificity are selected. Also, recombinant monoclonal antibodies or fragments thereof of the desired species can be isolated from phage display libraries as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity, affinity, etc. of a monoclonal antibody.

More generally, modified antibodies useful in the present invention may be obtained or derived from any antibody. Further, the parent or precursor antibody, or fragment thereof, used to generate the disclosed modified antibodies may be murine, human, chimeric, humanized, non-human primate or primatized. In other embodiments the modified antibodies of the present invention can comprise single chain antibody constructs (such as that disclosed in U.S. Pat. No. 5,892,019, which is incorporated herein by reference) having altered constant domains as described herein. Consequently, any of these types of antibodies modified in accordance with the teachings herein are compatible with this invention.

According to the present invention, techniques can be adapted for the production of single-chain antibodies specific to a polypeptide of the invention (see U.S. Pat. No. 4,946, 778). In addition, methods can be adapted for the construction of Fab expression libraries (Huse, et al., 1989, Science, 246: 1275-1281) to allow rapid and effective identification of monoclonal Fab fragments with the desired specificity for Notch or derivatives, fragments, analogs or homologs thereof. Antibody fragments that contain the idiotypes to a polypeptide of the invention may be produced by techniques in the art including, but not limited to: (a) an F(ab')$_2$ fragment produced by pepsin digestion of an antibody molecule; (b) an Fab fragment generated by reducing the disulfide bridges of an F(ab')$_2$ fragment, (c) an Fab fragment generated by the treatment of the antibody molecule with papain and a reducing agent, and (d) Fv fragments.

Bispecific antibodies are also within the scope of the invention. Bispecific antibodies are monoclonal, preferably human or humanized, antibodies that have binding specificities for at least two different antigens.

Methods for making bispecific antibodies are known in the art. For example, in the present case, one of the binding specificities is for an antigenic polypeptide of the invention (Notch1 or a fragment thereof), while the second binding target is any other antigen, and advantageously is a cell surface protein, or receptor or receptor subunit. Recombinant production of bispecific antibodies is based on the co-expression of two immunoglobulin heavy chain/light chain pairs, where the two heavy chains have different specificities (Milstein and Cuello, *Nature* 1983, 305:537-539). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography.

Antibody variable domains with the desired binding specificities can be fused to immunoglobulin constant domain sequences. The fusion is with an immunoglobulin heavy chain constant domain, comprising at least part of the hinge, CH2 and CH3 regions. The first heavy chain constant region (CH1) containing the site necessary for light chain binding can be present in at least one of the fusions. DNA encoding the immunoglobulin heavy chain fusions and, if desired, the immunoglobulin light chain, are inserted into separate expression vectors, and are co-transfected into a suitable host organism. Further details of generating bispecific antibodies can be found in Suresh et al., *Methods in Enzymology* 1986, 121:210.

Bispecific antibodies can be prepared as full-length antibodies or antibody fragments. Techniques for generating bispecific antibodies from antibody fragments have been described in the literature. For example, bispecific antibodies can be prepared using chemical linkage. In addition, Brennan et al., *Science* 1985, 229:81 describe a procedure wherein intact antibodies are proteolytically cleaved to generate F(ab')$_2$ fragments.

Additionally, Fab' fragments can be directly recovered from *E. coli* and chemically coupled to form bispecific antibodies (Shalaby et al., *J. Exp. Med.* 1992, 175:217-225). These methods can be used in the production of a fully humanized bispecific antibody F(ab')$_2$ molecule.

Antibodies with more than two valencies are also contemplated. For example, trispecific antibodies can be prepared (Tutt et al., 1991, *J. Immunol.* 147:60).

This invention also encompasses bispecific antibodies that specifically recognize the membrane proximal region of a extracellular domain of a Notch1 receptor. Bispecific antibodies are antibodies that are capable of specifically recognizing and binding at least two different epitopes. The different epitopes can either be within the same molecule (e.g. the same Notch1) or on different molecules such that both, for example, the antibodies can specifically recognize and bind a Notch1 receptor, as well as, for example, 1) an effector molecule on a leukocyte such as a T-cell receptor (e.g. CD3) or Fc receptor (e.g. CD64, CD32, or CD16) or 2) a cytotoxic agent as described in detail below. Bispecific antibodies can be intact antibodies or antibody fragments. Techniques for making bispecific antibodies are common in the art (Millstein et al., 1983, *Nature*, 305:537-539; Brennan et al., 1985, *Science*, 229:81; Suresh et al, 1986, *Methods in Enzymol.*, 121:120; Traunecker et al., 1991, *EMBO J.*, 10:3655-3659; Shalaby et al., 1992, *J. Exp. Med.*, 175:217-225; Kostelny et al., 1992, *J. Immunol.*, 148:1547-1553; Gruber et al., 1994, *J. Immunol.*, 152:5368; and U.S. Pat. No. 5,731,168).

Exemplary bispecific antibodies can bind to two different epitopes, at least one of which originates in a polypeptide of the invention. Alternatively, an anti-antigenic arm of an immunoglobulin molecule can be combined with an arm which binds to a triggering molecule on a leukocyte such as a T cell receptor molecule (e.g. CD2, CD3, CD28, or B7), or Fc receptors for IgG so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate antibodies are also within the scope of the present invention. Heteroconjugate antibodies are composed of two covalently joined antibodies. Such antibodies have, for example, been proposed to target immune cells to unwanted cells (U.S. Pat. No. 4,676,980). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate.

For the purposes of the present invention, it should be appreciated that modified antibodies can comprise any type of variable region that provides for the association of the antibody with a membrane proximal region of the extracellular domain of a Notch1 receptor. In this regard, the variable region may comprise or be derived from any type of mammal that can be induced to mount a humoral response and generate immunoglobulins against the desired tumor associated antigen. As such, the variable region of the modified antibodies can be, for example, of human, murine, non-human primate (e.g. cynomolgus monkeys, macaques, etc.) or lupine origin. In some embodiments both the variable and constant regions of the modified immunoglobulins are human. In other embodiments the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In some embodiments, of the present invention the monoclonal antibody against a membrane proximal region of the extracellular domain of a Notch1 receptor is a humanized antibody. Humanized antibodies are antibodies that contain minimal sequences from non-human (e.g., murine) antibodies within the variable regions. Such antibodies are used therapeutically to reduce antigenicity and HAMA (human anti-mouse antibody) responses when administered to a human subject. In practice, humanized antibodies are typically human antibodies with minimum to no non-human sequences. A human antibody is an antibody produced by a human or an antibody having an amino acid sequence corresponding to an antibody produced by a human.

Humanized antibodies can be produced using various techniques known in the art. An antibody can be humanized by substituting the CDR of a human antibody with that of a non-human antibody (e.g. mouse, rat, rabbit, hamster, etc.) having the desired specificity, affinity, and/or capability (Jones et al., 1986, *Nature,* 321:522-525; Riechmann et al., 1988, *Nature,* 332:323-327; Verhoeyen et al., 1988, *Science,* 239:1534-1536). The humanized antibody can be further modified by the substitution of additional residue either in the Fv framework region and/or within the replaced non-human residues to refine and optimize antibody specificity, affinity, and/or capability.

In some embodiments of the present invention, the antibody is a humanized antibody which specifically binds to a non-ligand binding membrane proximal region of the extracellular domain of a human Notch1 receptor. In some embodiments, the antibody comprises a heavy chain variable region having at least 90% sequence identity to SEQ ID NO:24; and/or a light chain variable region having at least 90% sequence identity to SEQ ID NO:28 or SEQ ID NO:32.

In some embodiments, the antibody comprises a heavy chain variable region having at least 95% sequence identity to SEQ ID NO:24, and/or a light chain variable region having at least 95% sequence identity to SEQ ID NO:28 or SEQ ID NO:32.

In some embodiments, the humanized antibody comprises a heavy chain variable region of SEQ ID NO:24, and a light chain variable region of SEQ ID NO:28. In some embodiments, the humanized antibody comprises a heavy chain variable region of SEQ ID NO:24, and a light chain variable region of SEQ ID NO:32.

Human antibodies can be directly prepared using various techniques known in the art. Immortalized human B lymphocytes immunized in vitro or isolated from an immunized individual that produces an antibody directed against a target antigen can be generated (See, for example, Cole et al., Monoclonal Antibodies and Cancer Therapy, Alan R. Liss, p. 77 (1985); Boemer et al., 1991, *J. Immunol.*, 147 (1):86-95; and U.S. Pat. No. 5,750,373). Also, the human antibody can be selected from a phage library, where that phage library expresses human antibodies (Vaughan et al., 1996, *Nature Biotechnology*, 14:309-314; Sheets et al., 1998, *PNAS*, 95:6157-6162; Hoogenboom and Winter, 1991, *J. Mol. Biol.*, 227:381; Marks et al., 1991, *J. Mol. Biol.*, 222:581). Humanized antibodies can also be made in transgenic mice containing human immunoglobulin loci that are capable, upon immunization, of producing the full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array into such germ-line mutant mice will result in the production of human antibodies upon antigen challenge. (See, for example, Jakobovits et al., 1993, *Proc. Natl. Acad. Sci. USA*, 90:2551; Jakobovits et al., 1993, *Nature*, 362:255-258; Bruggemann et al., 1993, *Year in Immuno.* 7:33; U.S. Pat. Nos. 5,545,807; 5,545,806; 5,569,825; 5,625,126; 5,633,425; and 5,661,016

Alternatively, phage display technology can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats. Several sources of V-gene segments can be used for phage display. A diverse array of anti-oxazolone antibodies have been isolated from a small random combinatorial library of V genes derived from the spleens of immunized mice. A repertoire of V genes from unimmunized human donors can be constructed and antibodies to a diverse array of antigens (including self-antigens) can be isolated.

As discussed above, human antibodies may also be generated by in vitro activated B cells (see U.S. Pat. Nos. 5,567,610 and 5,229,275).

It will be appreciated that grafting the entire non-human variable domains onto human constant regions will produce "classic" chimeric antibodies. In the context of the present application the term "chimeric antibodies" will be held to mean any antibody wherein the immunoreactive region or site is obtained or derived from a first species and the constant region (which may be intact, partial or modified in accordance with this invention) is obtained from a second species. In some embodiments, the antigen binding region or site will be from a non-human source (e.g. mouse) and the constant region is human. While the immunogenic specificity of the variable region is not generally affected by its source, a human constant region is less likely to elicit an immune response from a human subject than would the constant region from a non-human source.

The variable domains in both the heavy and light chains are altered by at least partial replacement of one or more CDRs and, if necessary, by partial framework region replacement and sequence changing. Although the CDRs may be derived from an antibody of the same class or even subclass as the antibody from which the framework regions are derived, it is envisaged that the CDRs will be derived from an antibody of different class and preferably from an antibody from a different species. It must be emphasized that it may not be necessary to replace all of the CDRs with the complete CDRs from the donor variable region to transfer the antigen binding capacity of one variable domain to another. Rather, it may only be necessary to transfer those residues that are necessary to maintain the activity of the antigen binding site. Given the explanations set forth in U.S. Pat. Nos. 5,585,089, 5,693,761 and 5,693,762, it will be well within the art, either by carrying out routine experimentation or by trial and error testing to obtain a functional antibody with reduced immunogenicity.

Alterations to the variable region notwithstanding, it will be appreciated that the modified antibodies of this invention will comprise antibodies, or immunoreactive fragments thereof, in which at least a fraction of one or more of the constant region domains has been deleted or otherwise altered so as to provide desired biochemical characteristics such as increased tumor localization or reduced serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies disclosed herein may comprise alterations or modifications to one or more of the three heavy chain constant domains (CH1, CH2 or CH3) and/or to the light chain constant domain (CL). In some embodiments of the invention modified constant regions wherein one or more domains are partially or entirely deleted are contemplated. In other embodiments the modified antibodies will comprise domain deleted constructs or variants wherein the entire CH2 domain has been removed (ΔCH2 constructs). In still other embodiments the omitted constant region domain will be replaced by a short amino acid spacer (e.g. 10 residues) that provides some of the molecular flexibility typically imparted by the absent constant region.

Besides their configuration, it is known in the art that the constant region mediates several effector functions. For example, binding of the C1 component of complement to antibodies activates the complement system. Activation of complement is important in the opsonization and lysis of cell pathogens. The activation of complement also stimulates the inflammatory response and can also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, or ADCC), release of inflammatory mediators, placental transfer and control of immunoglobulin production. Although various Fc receptors and receptor sites have been studied to a certain extent, there is still much which is unknown about their location, structure and functioning.

While not limiting the scope of the present invention, it is believed that antibodies comprising constant regions modified as described herein provide for altered effector functions that, in turn, affect the biological profile of the administered antibody. For example, the deletion or inactivation (through point mutations or other means) of a constant region domain may reduce Fc receptor binding of the circulating modified antibody thereby increasing tumor localization. In other cases it may be that constant region modifications, consistent with this invention, moderate complement binding and thus reduce the serum half life and nonspecific association of a conjugated cytotoxin. Yet other modifications of the constant region may be used to eliminate disulfide linkages or oligosaccharide moieties that allow for enhanced localization due to increased antigen specificity or antibody flexibility. Similarly, modifications to the constant region in accordance with this invention may easily be made using well known biochemical or molecular engineering techniques.

It will be noted that the modified antibodies may be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer may be added, for instance, to ensure that the regulatory elements of the constant domain remain free and accessible or that the hinge region remains flexible. However, it should be noted that amino acid spacers may, in some cases, prove to be immunogenic and elicit an unwanted immune response against the construct. Accordingly, any spacer added to the construct be relatively non-immunogenic or, even omitted altogether if the desired biochemical qualities of the modified antibodies may be maintained.

Besides the deletion of whole constant region domains, it will be appreciated that the antibodies of the present invention may be provided by the partial deletion or substitution of a few or even a single amino acid. For example, the mutation of a single amino acid in selected areas of the CH2 domain may be enough to substantially reduce Fc binding and thereby increase tumor localization. Similarly, it may be desirable to simply delete that part of one or more constant region domains that control the effector function (e.g. complement CLQ binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g. Fc binding) while substantially maintaining the configuration and immunogenic profile of the modified antibody. Yet other embodiments may comprise the addition of one or more amino acids to the constant region to enhance desirable characteristics such as effector function or provide for more cytotoxin or carbohydrate attachment. In such embodiments it can be desirable to insert or replicate specific sequences derived from selected constant region domains.

In certain embodiments of the invention, it can be desirable to use an antibody fragment, rather than an intact antibody, to increase tumor penetration, for example. Various techniques are known for the production of antibody fragments. Traditionally, these fragments are derived via proteolytic digestion of intact antibodies (for example Morimoto et al., 1993, *Journal of Biochemical and Biophysical Methods* 24:107-117 and Brennan et al., 1985, *Science,* 229:81). However, these fragments are now typically produced directly by recombinant host cells as described above. Thus Fab, Fv, and scFv antibody fragments can all be expressed in, and secreted from, *E. coli* or other host cells, thus allowing the production of large amounts of these fragments. Alternatively, such antibody fragments can be isolated from the antibody phage libraries discussed herein. The antibody fragment can also be linear antibodies as described in U.S. Pat. No. 5,641,870, for example, and can be monospecific or bispecific. Other techniques for the production of antibody fragments will be apparent to one of skill in the art.

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis).

The present invention further embraces variants and equivalents which are substantially homologous to the chimeric, humanized and human antibodies, or antibody fragments thereof, set forth herein. These can contain, for example, conservative substitution mutations, i.e. the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The invention also pertains to immunoconjugates comprising an antibody conjugated to a cytotoxic agent. Cytotoxic agents include chemotherapeutic agents, growth inhibitory agents, toxins (e.g., an enzymatically active toxin of bacterial, fungal, plant, or animal origin, or fragments thereof), radioactive isotopes (i.e., a radioconjugate), etc. Chemotherapeutic agents useful in the generation of such immunoconjugates include, for example, methotrexate, adriamicin, doxorubicin, melphalan, mitomycin C, chlorambucil, daunorubicin or other intercalating agents. Enzymatically active toxins and fragments thereof that can be used include diphtheria A chain, nonbinding active fragments of diphtheria toxin, exotoxin A chain, ricin A chain, abrin A chain, modeccin A chain, alphasarcin, *Aleurites fordii* proteins, dianthin proteins, *Phytolaca americana* proteins (PAPI, PAPII, and PAP-S), *Momordica charantia* inhibitor, curcin, crotin, *Sapaonaria officinalis* inhibitor, gelonin, mitogellin, restrictocin, phenomycin, enomycin, and the tricothecenes. In some embodiments, the antibodies can be conjugated to radioisotopes, such as $^{90}Y$, $^{125}I$, $^{131}$I, $^{123}$I, $^{111}$In, $^{105}$Rh, $^{153}$Sm, $^{67}$Cu, $^{67}$Ga, $^{166}$Ho, $^{177}$Lu, $^{186}$Re and $^{188}$Re using anyone of a number of well known chelators or direct labeling. In other embodiments, the disclosed compositions can comprise antibodies coupled to drugs, prodrugs, or lymphokines such as interferon. Conjugates of the antibody and cytotoxic agent are made using a variety of bifunctional protein-coupling agents such as N-succinimidyl-3-(2-pyridyidithiol)propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). Conjugates of an antibody and one or more small molecule toxins, such as a calicheamicin, maytansinoids, a trichothene, and CC1065, and the derivatives of these toxins that have toxin activity, can also be used. In some embodiments, the modified antibodies can be complexed with other immunologically active ligands (e.g., antibodies or fragments thereof) wherein the resulting molecule binds to both the neoplastic cell and an effector cell such as a T cell.

Regardless of how useful quantities are obtained, the antibodies of the present invention can be used in any one of a number of conjugated (i.e. an immunoconjugate) or unconjugated forms. Alternatively, the antibodies of this invention can be used in a nonconjugated or "naked" form to harness the subject's natural defense mechanisms including complement-dependent cytotoxicity (CDC) and antibody dependent cellular toxicity (ADCC) to eliminate the malignant cells. The selection of which conjugated or unconjugated modified antibody to use will depend of the type and stage of cancer, use of adjunct treatment (e.g., chemotherapy or external radiation) and patient condition. It will be appreciated that one could readily make such a selection in view of the teachings herein.

Competition assays can be used to determine whether two antibodies bind the same epitope by recognizing identical or sterically overlapping epitopes. Any method known to one of skill in the art for determining competitive binding (such as e.g., the immunoassays described elsewhere herein) may be used.

The antibodies of the present invention can be assayed for immunospecific binding by any method known in the art. The immunoassays which can be used include, but are not limited to, competitive and non-competitive assay systems using techniques such as Biacore analysis, FACS analysis, immunofluorescence, immunocytochemistry, Western blot analysis, radioimmunoassay, ELISA, "sandwich" immunoassay, immunoprecipitation assay, precipitin reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety).

In some embodiments, of the present invention the immunospecificity of an antibody against a membrane proximal region of the extracellular domain of a human Notch1 receptor is determined using ELISA. An ELISA assay comprises preparing antigen, coating wells of a 96 well microtiter plate with antigen, adding the antibody against a cancer stem cell marker conjugated to a detectable compound such as an enzymatic substrate (e.g. horseradish peroxidase or alkaline phosphatase) to the well, incubating for a period of time and detecting the presence of the antigen. Alternatively the antibody against a membrane proximal region of the extracellular domain of a human Notch1 receptor is not conjugated to a detectable compound, but instead a second conjugated antibody that recognizes the antibody against a membrane proximal region of the extracellular domain of a human Notch1 receptor is added to the well. Further, instead of coating the well with the antigen, the antibody against a membrane proximal region of the extracellular domain of a human Notch1 receptor can be coated to the well and a second antibody conjugated to a detectable compound can be added following the addition of the antigen to the coated well. It is known to one of skill in the art what parameters can be modified to increase the signal detected as well as other variations of ELISAs known in the art (see e.g. Ausubel et al, eds, 1994, Current Protocols in Molecular Biology, Vol. 1, John Wiley & Sons, Inc., New York at 11.2.1).

The binding affinity of an antibody to a membrane proximal region of the extracellular domain of Notch1 receptor and the off-rate of an antibody-antigen interaction can be determined by competitive binding assays. One example of a competitive binding assay is a radioimmunoassay comprising the incubation of labeled antigen (e.g. $^3$H or $^{135}$I), or fragment or variant thereof, with the antibody of interest in the presence of increasing amounts of unlabeled antigen followed by the detection of the antibody bound to the labeled antigen. The affinity of the antibody against a membrane proximal region of the extracellular domain of a human Notch1 receptor and the binding off-rates can be determined from the data by Scatchard plot analysis. In some embodiments, Biacore kinetic analysis is used to determine the binding on and off rates of antibodies against a membrane proximal region of the extracellular domain of a human Notch1 receptor. Biacore kinetic analysis comprises analyzing the binding and dissociation of antibodies from chips with immobilized antigen, for example, Notch1 receptors, on their surface.

In certain embodiments, the invention encompasses isolated polynucleotides that encode a polypeptide comprising an antibody or fragment thereof, against a non-ligand binding membrane proximal region of the extracellular domain of a human Notch1 receptor. The term "polynucleotide encoding a polypeptide" encompasses a polynucleotide which includes only coding sequences for the polypeptide as well as a polynucleotide which includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single stranded can be the coding strand or non-coding (anti-sense) strand. The polynucleotides of the invention can be in the form of RNA or in the form of DNA, which DNA includes cDNA, genomic DNA, and synthetic DNA. The DNA can be double-stranded or single-stranded, and if single stranded can be the coding strand or non-coding (anti-sense) strand.

The present invention further relates to variants of the hereinabove described polynucleotides which encode for fragments, analogs, and derivatives. The variant of the polynucleotide can be a naturally occurring allelic variant of the polynucleotide or a non-naturally occurring variant of the polynucleotide.

As hereinabove indicated, the polynucleotide can have a coding sequence which is a naturally occurring allelic variant of the coding sequence of the disclosed polypeptides. As known in the art, an allelic variant is an alternate form of a polynucleotide sequence which has a substitution, deletion or addition of one or more nucleotides, which does not substantially alter the function of the encoded polypeptide.

The present invention also includes polynucleotides, wherein the coding sequence for the mature polypeptide can be fused in the same reading frame to a polynucleotide which aids in expression and secretion of a polypeptide from a host cell, for example, a leader sequence which functions as a secretory sequence for controlling transport of a polypeptide from the cell. The polypeptide having a leader sequence is a preprotein and can have the leader sequence cleaved by the host cell to form the mature form of the polypeptide. The polynucleotides can also encode for a proprotein which is the mature protein plus additional 5' amino acid residues. A mature protein having a prosequence is a proprotein and is an inactive form of the protein. Once the prosequence is cleaved an active mature protein remains. Thus, for example, the polynucleotide of the present invention can encode for a mature protein, or for a protein having a prosequence or for a protein having both a prosequence and presequence (leader sequence).

The polynucleotides of the present invention can also have the coding sequence fused in frame to a marker sequence which allows for purification of the polypeptide of the present invention. The marker sequence can be a hexa-histidine tag supplied by a pQE-9 vector to provide for purification of the mature polypeptide fused to the marker in the case of a bacterial host, or, for example, the marker sequence can be a hemagglutinin (HA) tag when a mammalian host, e.g. COS-7 cells, is used. The HA tag corresponds to an epitope derived from the influenza hemagglutinin protein (Wilson et al., 1984, *Cell* 37:767).

Further embodiments of the invention include isolated nucleic acid molecules comprising a polynucleotide having a nucleotide sequence at least 90% identical, 95% identical, and in some embodiments, at least 96%, 97%, 98% or 99% identical to the disclosed sequences. In some embodiments, the polynucleotides have a nucleotide sequence at least 90% identical to SEQ ID NOs: 3, 5, 7, 9, 11, 13, 21, 25 or 29 (with or without signal sequence). In some embodiments, the polynucleotides have a nucleotide sequence at least 90% identical to SEQ ID NOs:7 or 13. In some embodiments, the invention provides a polynucleotide that hybridizes to a polynucleotide encoding the polypeptides of SEQ ID NOs:4, 6, 8, 10, 12, 14, 22, 23, 24, 26, 27, 28, 30, 31, or 32. In some embodiments, the polynucleotides hybridize to the polynucleotides of SEQ ID NOs:3, 5, 7, 9, 11, 13, 21, 25 or 29. In some embodiments, the polynucleotides hybridize under stringent hybridization conditions.

As used herein, the phrases "hybridizes" or "selectively hybridizes" or "specifically hybridizes" refer to the binding or duplexing of a molecule only to a particular nucleotide sequence under stringent hybridization conditions when that sequence is present in a complex mixture (e.g., a library of DNAs or RNAs). See, e.g., Andersen (1998) Nucleic Acid Hybridization Springer-Verlag; Ross (ed. 1997) Nucleic Acid Hybridization Wiley.

As used herein, the phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, Techniques in Biochemistry and Molecular Biology—Hybridization with Nucleic Probes, "Overview of principles of hybridization and the strategy of nucleic acid assays" (1993). Generally, stringent conditions are selected to be about 5-10° C. lower than the thermal melting point (Tm) for the specific sequence at a defined ionic strength. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For high stringency hybridization, a positive signal is at least two times background, or 10 times background hybridization. Exemplary high stringency or stringent hybridization conditions include: 50% formamide, 5×SSC, and 1% SDS incubated at 42° C. or 5×SSC and 1% SDS incubated at 65° C., with a wash in 0.2×SSC and 0.1% SDS at 65° C. For PCR, a temperature of about 36° C. is typical for low stringency amplification, although annealing temperatures can vary from about 32° C. to about 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C. to 95° C. for 30-120 sec, an annealing phase lasting 30-120 sec, and an extension phase of about 72° C. for 1-2 min.

By a polynucleotide having a nucleotide sequence at least, for example, 95% "identical" to a reference nucleotide sequence is intended that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the amino- or carboxy-terminal positions of the reference nucleotide sequence or anywhere between those terminal positions, interspersed either individually among nucleotides in the reference sequence or in one or more contiguous groups within the reference sequence.

As a practical matter, whether any particular nucleic acid molecule is at least 95%, 96%, 97%, 98% or 99% identical to a reference sequence can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, Advances in Applied Mathematics 2: 482 489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

The polynucleotide variants can contain alterations in the coding regions, non-coding regions, or both. In some embodiments the polynucleotide variants contain alterations which produce silent substitutions, additions, or deletions, but do not alter the properties or activities of the encoded polypeptide. In some embodiments, nucleotide variants are produced by silent substitutions due to the degeneracy of the genetic code. Polynucleotide variants can be produced for a variety of reasons, e.g., to optimize codon expression for a particular host (change codons in the human mRNA to those preferred by a bacterial host such as *E. coli*).

The polypeptides of the present invention can be recombinant polypeptides, natural polypeptides, or synthetic polypeptides comprising an antibody, or fragment thereof, against a non-ligand binding membrane proximal region of the extracellular domain of a human Notch1 receptor. It will be recognized in the art that some amino acid sequences of the invention can be varied without significant effect of the structure or function of the protein. Thus, the invention further includes variations of the polypeptides which show substantial activity or which include regions of an antibody, or fragment thereof, against a membrane proximal region of the extracellular domain of a human Notch1 receptor. Such mutants include deletions, insertions, inversions, repeats, and type substitutions.

The polypeptides and polynucleotides of the present invention are provided in an isolated form, and at times are purified to homogeneity.

The isolated polypeptides described herein can be produced by any suitable method known in the art. Such methods range from direct protein synthesis methods to constructing a DNA sequence encoding isolated polypeptide sequences and expressing those sequences in a suitable transformed host. For example, cDNA can be obtained by screening a human cDNA library with a labeled DNA fragment encoding a polypeptide (for example, nucleotide SEQ ID NO:1) and identifying positive clones by autoradiography. Further rounds of plaque purification and hybridization are performed using conventional methods.

In some embodiments of a recombinant method, a DNA sequence is constructed by isolating or synthesizing a DNA sequence encoding a wild-type protein of interest. Optionally, the sequence can be mutagenized by site-specific mutagenesis to provide functional analogs thereof. (See, e.g. Zoeller et al., 1984, *Proc.-Nat Acad. Sci. USA,* 81:5662-5066 and U.S. Pat. No. 4,588,585.) Another method of constructing a DNA sequence encoding a polypeptide of interest would be by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced.

Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5′ or 3′ overhangs for complementary assembly.

Once assembled (by synthesis, site-directed mutagenesis or another method), the mutant DNA sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene is operatively linked to transcriptional and translational expression control sequences that are functional in the chosen expression host.

Recombinant expression vectors are used to amplify and express DNA encoding cancer stem cell marker polypeptide fusions. Recombinant expression vectors are replicable DNA constructs which have synthetic or cDNA-derived DNA fragments encoding a cancer stem cell marker polypeptide fusion or a bioequivalent analog operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences, as described in detail below. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Generally, operatively linked means contiguous and, in the case of secretory leaders, means contiguous and in reading frame. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A wide variety of expression host/vector combinations can be employed. Useful expression vectors for eukaryotic hosts, include, for example, vectors comprising expression control sequences from SV40, bovine papilloma virus, adenovirus and cytomegalovirus. Useful expression vectors for bacterial hosts include known bacterial plasmids, such as plasmids from *Esherichia coli*, including pCR1, pBR322, pMB9 and their derivatives, and wider host range plasmids, such as M13 and filamentous single-stranded DNA phages.

Suitable host cells for expression of a cancer stem cell marker protein include prokaryotes, yeast, insect or higher eukaryotic cells. Prokaryotes include gram negative or gram positive organisms, for example *E. coli* or bacilli. Higher eukaryotic cells include established cell lines of mammalian origin as described below. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference.

Various mammalian or insect cell culture systems are also advantageously employed to express recombinant protein. Expression of recombinant proteins in mammalian cells can be performed because such proteins are generally correctly folded, appropriately modified and completely functional. Examples of suitable mammalian host cell lines include the COS-7 lines of monkey kidney cells, described by Gluzman (1981, Cell, 23:175), and other cell lines capable of expressing an appropriate vector including, for example, L cells, C127, 3T3, Chinese hamster ovary (CHO), HeLa and BHK cell lines. Mammalian expression vectors can comprise non-transcribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, 1988, Bio/Technology, 6:47.

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further purify a recombinant protein or cancer stem cell protein-Fc composition. Some or all of the foregoing purification steps, in various combinations, can also be employed to provide a homogeneous recombinant protein.

Recombinant protein produced in bacterial culture is usually isolated by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

The present invention also provides methods for inhibiting the growth of tumorigenic cells expressing a cancer stem cell marker using the antagonists of a cancer stem cell marker described herein. In some embodiments, the method of inhibiting the growth of tumorigenic cells expressing a cancer stem cell marker, for example Notch1 receptor, comprises contacting the cell with an antagonist against a cancer stem cell marker in vitro. For example, an immortalized cell line or a cancer cell line that expresses a cancer stem cell marker is cultured in medium to which is added an antagonist of the expressed cancer stem cell marker to inhibit cell growth. In some embodiments, tumor cells comprising tumor stem cells are isolated from a patient sample such as, for example, a tissue biopsy, pleural effusion, or blood sample and cultured in medium to which is added an antagonist of a cancer stem cell marker to inhibit cell growth. In some embodiments, the antagonist is an antibody that specifically recognizes an epitope of a cancer stem cell marker protein. For example, antibodies against a cancer stem cell marker protein can be added to the culture medium of isolated cancer stem cells to inhibit cell growth.

In some embodiments, the method of inhibiting the growth of tumorigenic cells expressing a cancer stem cell marker comprises contacting the cell with an antagonist against a cancer stem cell marker in vivo. In some embodiments, the method of inhibiting growth of tumorigenic cells expressing Notch1 comprises contacting the cells with an antibody that specifically binds to a non-ligand binding membrane proximal region of a human Notch1 receptor. In some embodiments, the antibody inhibits growth of tumorigenic cells by inhibiting the activity of Notch1. In some embodiments, the antibody inhibits growth of tumorigenic cells by inhibiting ligand-induced Notch1 signaling. In some embodiments, the antibody inhibits growth of tumorigenic cells by inhibiting the cleavage of Notch1. In some embodiments, the antibody inhibits growth of tumorigenic cells by reducing the frequency or the number of cancer stem cells in the tumor.

In certain embodiments, contacting a tumorigenic cell with an antagonist to a cancer stem cell marker is undertaken in an animal model. For example, xenografts expressing a cancer stem cell marker are grown in immunocompromised mice (e.g. NOD/SCID mice) that are administered an antagonist to a cancer stem cell marker to inhibit tumor growth. In some embodiments, cancer stem cells that express a cancer stem cell marker are isolated from a patient sample such as, for example, a tissue biopsy, pleural effusion, or blood sample and injected into immunocompromised mice that are then administered an antagonist against the cancer stem cell marker to inhibit tumor cell growth. In some embodiments, the antagonist of a cancer stem cell marker is administered at the same time or shortly after introduction of tumorigenic cells into the animal to prevent tumor growth. In other embodiments, the antibody against the cancer stem cell marker is administered as a therapeutic agent after the tumorigenic cells have grown to a specified size.

The present invention further provides pharmaceutical compositions comprising antibodies, polypeptides or other agents that target a cancer stem cell marker. These pharmaceutical compositions find use in inhibiting tumor growth, tumor cell growth and treating cancer in human patients.

Formulations are prepared for storage and use by combining a purified antagonist (e.g., antibody) of the present invention with a pharmaceutically acceptable vehicle (e.g., carrier, excipient, etc.) (Remington, The Science and Practice of Pharmacy 20th Edition Mack Publishing, 2000). Suitable pharmaceutically acceptable vehicles include, but are not limited to, nontoxic buffers such as phosphate, citrate, and other organic acids; salts such as sodium chloride; antioxidants including ascorbic acid and methionine; preservatives such as octadecyldimethylbenzyl ammonium chloride; hexamethonium chloride; benzalkonium chloride; benzethonium chloride; phenol, butyl or benzyl alcohol; alkyl parabens, such as methyl or propyl paraben; catechol; resorcinol; cyclohexanol; 3-pentanol; and m-cresol; low molecular weight polypeptides (less than about 10 amino acid residues); proteins such as serum albumin, gelatin, or immunoglobulins; hydrophilic polymers such as polyvinylpyrrolidone; amino acids such as glycine, glutamine, asparagine, histidine, arginine, or lysine; carbohydrates such as monosacchandes, disaccharides, glucose, mannose, or dextrins; chelating agents such as EDTA; sugars such as sucrose, mannitol, trehalose or sorbitol; salt-forming counter-ions such as sodium; metal complexes such as Zn-protein complexes; and/or nonionic surfactants such as TWEEN or polyethylene glycol (PEG).

The pharmaceutical composition of the present invention can be administered in any number of ways for either local or systemic treatment. Administration can be topical (such as to mucous membranes including vaginal and rectal delivery) such as transdermal patches, ointments, lotions, creams, gels, drops, suppositories, sprays, liquids and powders; pulmonary such as by inhalation or insufflation of powders or aerosols (including by nebulizer), intratracheal, intranasal, epidermal and transdermal; oral; parenteral including intravenous, intraarterial, intratumoral, subcutaneous, intraperitoneal or intramuscular injection or infusion; or intracranial such asintrathecal or intraventricular.

The therapeutic formulation can be in unit dosage form. Such formulations include tablets, pills, capsules, powders, granules, solutions or suspensions in water or non-aqueous media, or suppositories for oral, parenteral, or rectal administration or for administration by inhalation. In solid compositions such as tablets the principal active ingredient is mixed with a pharmaceutical carrier. Conventional tableting ingredients include corn starch, lactose, sucrose, sorbitol, talc, stearic acid, magnesium stearate, dicalcium phosphate or gums, and other diluents (e.g., water) to form a solid preformulation composition containing a homogeneous mixture of a compound of the present invention, or a non-toxic pharmaceutically acceptable salt thereof. The solid preformulation composition is then subdivided into unit dosage forms of the type described herein. The tablets, pills, etc of the novel composition can be coated or otherwise compounded to provide a dosage form affording the advantage of prolonged action. For example, the tablet or pill can comprise an inner composition covered by an outer component. Furthermore, the two components can be separated by an enteric layer that serves to resist disintegration and permits the inner component to pass intact through the stomach or to be delayed in release. A variety of materials can be used for such enteric layers or coatings, such materials including a number of polymeric acids and mixtures of polymeric acids with such materials as shellac, cetyl alcohol and cellulose acetate.

Pharmaceutical formulations include antibodies of the present invention complexed with liposomes (Epstein, et al., 1985, Proc. Natl. Acad. Sci. USA, 82:3688; Hwang, et al., 1980, Proc. Natl. Acad. Sci. USA, 77:4030; and U.S. Pat. Nos. 4,485,045 and 4,544,545). Liposomes with enhanced circulation time are disclosed in U.S. Pat. No. 5,013,556. Some liposomes can be generated by the reverse phase evaporation with a lipid composition comprising phosphatidylcholine, cholesterol, and PEG-derivatized phosphatidylethanolamine (PEG-PE). Liposomes are extruded through filters of defined pore size to yield liposomes with the desired diameter.

The antibodies can also be entrapped in microcapsules. Such microcapsules are prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions as described in Remington, The Science and Practice of Pharmacy 20th Ed. Mack Publishing (2000).

In addition sustained-release preparations can be prepared. Suitable examples of sustained-release preparations include semi-permeable matrices of solid hydrophobic polymers containing the antibody, which matrices are in the form of shaped articles (e.g. films, or microcapsules). Examples of sustained-release matrices include polyesters, hydrogels such as poly (2-hydroxyethyl-methacrylate) or poly(v nylalcohol), poly-lactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D(−)-3-hydroxybutyric acid. In some embodiments the antibodies can be used to treat various conditions characterized by expression and/or increased responsiveness of cells to a cancer stem cell marker. Particularly it is envisioned that the antibodies against a cancer stem cell marker, for example Notch1, will be used to treat proliferative disorders including but not limited to benign and malignant tumors of the kidney, liver, bladder, breast, stomach, ovary, colon, rectum, prostate, lung, vulva, thyroid, head and neck, brain (glioblastoma, astrocytoma, medulloblastoma, etc), blood and lymph (leukemias and lymphomas).

In some embodiments, the treatment involves the combined administration of an antibody or other agent of the present invention and a chemotherapeutic agent or cocktail of multiple different chemotherapeutic agents. Treatment with an antibody can occur prior to, concurrently with, or subsequent to administration of chemotherapies. Chemotherapies contemplated by the invention include chemical substances or drugs which are known in the art and are commercially available, such as doxorubicin, 5-fluorouracil, cytosine arabinoside ("Ara-C"), cyclophosphamide, thiotepa, busulfan, cytoxin, taxol, methotrexate, cisplatin, melphalan, vinblastine and carboplatin. Combined administration can include co-administration, either in a single pharmaceutical formulation or using separate formulations, or consecutive administration in either order but generally within a time period such that all active agents can exert their biological activities simultaneously. Preparation and dosing schedules for such chemotherapeutic agents can be used according to manufacturers' instructions or as determined empirically. Preparation and dosing schedules for such chemotherapy are also described in Chemotherapy Service Ed., M. C. Perry, Williams & Wilkins, Baltimore, Md. (1992).

Chemotherapeutic agents useful in the instant invention also include, but are not limited to, alkylating agents such as thiotepa and cyclophosphamide (Cytoxan); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamime nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, caminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, 5-FU; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elformithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK; razoxane; sizofuran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel (TAXOL, Bristol-Myers Squibb Oncology, Princeton, N.J.) and doxetaxel (Taxotere, Rhone-Poulenc Rorer, Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT11; topoisomerase inhibitor RFS 2000; difluoromethylornithine (DMFO); retinoic acid; esperamicins; capecitabine; and pharmaceutically acceptable salts, acids or derivatives of any of the above. Chemotherapeutic agents also include anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY117018, onapristone, and toremifene (Fareston); and antiandrogens such as flutamide, nilutamide, bicalutamide, leuprolide, and goserelin; and pharmaceutically acceptable salts, acids or derivatives of any of the above.

In certain embodiments, the chemotherapeutic agent is a topoisomerase inhibitor. Topoisomerase inhibitors are chemotherapy agents that interfere with the action of a topoisomerase enzyme (e.g., topoisomerase I or II). Topoisomerase inhibitors include, but are not limited to, doxorubicin HCL, daunorubicin citrate, mitoxantrone HCL, actinomycin D, etoposide, topotecan HCL, teniposide (VM-26), and irinotecan.

In certain embodiments, the chemotherapeutic agent is an anti-metabolite. An anti-metabolite is a chemical with a structure that is similar to a metabolite required for normal biochemical reactions, yet different enough to interfere with one or more normal functions of cells, such as cell division. Antimetabolites include, but are not limited to, gemcitabine, fluorouracil, capecitabine, methotrexate sodium, ralitrexed, Pemetrexed, tegafur, cytosine arabinoside, Thioguanine (GlaxoSmithKline), 5-azacytidine, 6-mercaptopurine, azathioprine, 6-thioguanine, pentostatin, fludarabine phosphate, and cladribine, as well as pharmaceutically acceptable salts, acids, or derivatives of any of these.

In other embodiments, the treatment involves the combined administration of an antibody or other agent of the present invention and radiation therapy. Treatment with an antibody can occur prior to, concurrently with, or subsequent to administration of radiation therapy. Any dosing schedules for such radiation therapy can be used as determined by the skilled practitioner.

In other embodiments, the treatment can involve the combined administration of antibodies of the present invention with other antibodies against additional tumor associated antigens including, but not limited to, antibodies that bind to the EGF receptor (EGFR) (Erbitux®), the erbB2 receptor (HER2) (Herceptin®), and vascular endothelial growth factor (VEGF) (Avastin®). Furthermore, treatment can include administration of one or more cytokines; can be accompanied by surgical removal of cancer cells; and/or any other therapy deemed necessary by a treating physician.

For the treatment of the disease, the appropriate dosage of an antibody or other agent of the present invention depends on the type of disease to be treated, the severity and course of the disease, the responsiveness of the disease, whether the antibody is administered for therapeutic or preventative purposes, previous therapy, patient's clinical history, and so on all at the discretion of the treating physician. The antibody or agent can be administered one time or over a series of treatments lasting from several days to several months, or until a cure is effected or a diminution of the disease state is achieved (e.g. reduction in tumor size). Optimal dosing schedules can be calculated from measurements of drug accumulation in the body of the patient and will vary depending on the relative potency of an individual antagonist. The administering physician can easily determine optimum dosages, dosing methodologies and repetition rates. In general, dosage is from 0.01 µg to 100 mg per kg of body weight, and can be given once or more daily, weekly, monthly or yearly. The treating physician can estimate repetition rates for dosing based on measured residence times and concentrations of the antibody or agent in bodily fluids or tissues.

The present invention provides kits comprising the antibodies described herein and that can be used to perform the methods described herein. In some embodiments, a kit comprises at least one purified antibody against a cancer stem cell marker, in one or more containers. In some embodiments, a kit comprises at least one purified antibody against a non-ligand binding membrane proximal region of the extracellular domain of a human Notch1 receptor, in one or more containers. In some embodiments, a kit comprises the antibody 52M51 or a humanized variant of 52M51. In some embodiments, a kit comprises the antibody 52R43. In some embodiments, the kits contain all of the components necessary and/or sufficient to perform a detection assay, including all controls, directions for performing assays, and any necessary software for analysis and presentation of results. One skilled in the art will readily recognize that the disclosed antibodies of the present invention can be readily incorporated into one of the established kit formats which are well known in the art.

In certain embodiments, the present invention provides a method of identifying a molecule that binds to a non-ligand binding membrane proximal region of the extracellular domain of a human Notch1 receptor and inhibits tumor growth, the method comprising: i) incubating the molecule with the non-ligand binding membrane proximal region of the extracellular domain of the human Notch1 receptor; ii) determining if the molecule binds to the membrane proximal region of the extracellular domain of the human Notch receptor; and iii) determining if the molecule inhibits tumor growth. Molecules that specifically bind a membrane proximal region of the extracellular domain of a human Notch1 receptor include, but are not limited to, polypeptides and antibodies.

Screening can be performed using any suitable method known in the art. In certain embodiments, screening is performed in vitro. In some embodiments, cells expressing a non-ligand binding membrane proximal region of the extracellular domain of a human Notch1 receptor are incubated with a labeled molecule and specific binding of the labeled molecule to a membrane proximal region of the extracellular domain of a human Notch1 receptor is determined by FACS analysis. In some embodiments, a non-ligand binding membrane proximal region of the extracellular domain of a human Notch1 receptor is expressed by phage display, and molecules that specifically binding to a membrane proximal region of the extracellular domain of a human Notch1 receptor are identified. Other suitable methods for identifying molecules that specifically bind to a non-ligand binding membrane proximal region of a human Notch1 receptor include, but are not limited to, ELISA; Western (or immuno) blotting; and yeast-two-hybrid.

Molecules that specifically bind to a non-ligand binding membrane proximal region of the extracellular domain of a human Notch1 receptor are then tested for inhibition of tumor cell growth. Testing can be performed using any suitable method known in the art. In certain embodiments, molecules that specifically bind to membrane proximal region of the extracellular domain of a human Notch1 receptor are tested for the ability to inhibit tumor growth in vitro. In some embodiments, molecules that specifically bind a membrane proximal region of the extracellular domain of a human Notch1 receptor are incubated with tumor cells in culture and proliferation of tumor cells in the presence of the molecule that specifically binds a membrane proximal region of the extracellular domain of a human Notch1 receptor is determined and compared to tumor cells incubated with a non-binding control molecule. In certain embodiments, molecules that specifically bind to non-ligand binding membrane proximal region of the extracellular domain of a human Notch1 receptor are tested for the ability to inhibit tumor growth in vivo. In certain embodiments, molecules that specifically bind a membrane proximal region of the extracellular domain of a human Notch1 receptor are injected into an animal xenograft model and the growth of tumors in animals treated with molecules that specifically bind to the membrane proximal region of the extracellular domain of a human Notch1 receptor is determined and compared to animals treated with a non-binding control molecule.

EXAMPLES

Example 1

Antibodies were generated against a non-ligand binding region of Notch1, specifically the non-ligand binding membrane proximal region of the extracellular domain. In certain embodiments, recombinant polypeptide fragments of the human Notch1 extracellular domain were generated as antigens for antibody production. Standard recombinant DNA technology was used to isolate polynucleotides encoding the membrane proximal region of the extracellular domain of human Notch1 amino acids 1427-1732 (SEQ ID NO:1). These polynucleotides were separately ligated in-frame N-terminal to a human Fc and histidine-tag and cloned into a transfer plasmid vector for baculovirus-mediated expression in insect cells. Standard transfection, infection, and cell culture protocols were used to produce recombinant insect cells expressing the corresponding Notch1 polypeptide corresponding to a membrane proximal region comprising amino acids 1427-1732 (SEQ ID NO:2) (O'Reilly et al., 1994, Baculovirus Expression Vectors: A Laboratory Manual, Oxford: Oxford University Press).

Notch1 membrane proximal region (Notch1 amino acids 1472-1732) polypeptide was purified from insect cell lysates using protein A and Ni++-chelate affinity chromatography as known to one skilled in the art. Purified Notch1 membrane proximal region polypeptide was dialyzed against PBS (pH=7), concentrated to approximately 1 mg/ml, and sterile filtered in preparation for immunization.

Mice (n=3) were immunized with purified Notch1 antigen protein (Antibody Solutions; Mountain View, Calif.) using standard techniques. Blood from individual mice was screened approximately 70 days after initial immunization for antigen recognition using ELISA and FACS analysis (as described herein). The two animals with the highest antibody titers were selected for final antigen boost after which spleen cells were isolated for hybridoma production. Hybridoma cells were plated at 1 cell per well in 96 well plates, and the supernatant from each well screened by ELISA and FACS analysis against Notch1 membrane proximal region polypeptide. Several hybridomas with high antibody titer were selected and scaled up in static flask culture. Antibodies were purified from the hybridoma supernatant using protein A or protein G agarose chromatography. Purified monoclonal antibodies were tested again by FACS as described herein. Several antibodies that recognized the membrane proximal region of the extracellular domain of human Notch1 were isolated. A hydridoma cell line expressing antibody 52M51 was deposited with ATCC under the conditions of the Budapest Treaty on Aug. 7, 2008 and assigned ATTC Patent Deposit Designation PTA-9405. The nucleotide and predicted protein sequences of both the heavy chain (SEQ ID NO:9 and 10) and light chain (SEQ ID NO:3 and 4) of antibody 52M51 were determined.

Human Antibodies

In alternative embodiments, human antibodies that specifically recognize the non-ligand binding membrane proximal region of the extracellular domain of a Notch1 receptor are isolated using phage display technology. In certain embodiments, a synthetic antibody library containing human antibody variable domains is screened for specific and high affinity recognition of a Notch receptor antigen described herein. In certain embodiments, a human Fab phage display library is screened using a series of recombinant proteins comprising the non-ligand binding membrane proximal region of the extracellular domain of a Notch 1 receptor. Briefly, $2\times10^{13}$ Fab displaying phage particles are incubated with recombinant protein (passively immobilized) in round one, the non-specific phage are washed off, and then specific phage are eluted with either low pH (cells) or DTT (recombinant protein). The eluted output is used to infect TG1 F+ bacteria, rescued with helper phage, and then Fab display induced with IPTG (0.25 mM). This process is repeated for two additional rounds and then round three is screened in ELISA against passively immobilized antigen (5 µg/ml).

CDR cassettes in the library are specifically exchanged via unique flanking restriction sites for antibody optimization. Optimized human variable regions are then cloned into an Ig expression vector containing human IgG1 heavy-chain and kappa light-chain for expression of human antibodies in CHO cells.

Epitope Mapping

To identify antibodies that recognize specific a non-ligand binding membrane proximal region of the Notch1 receptor extracellular domains, epitope mapping is performed. In certain embodiments, mammalian expression plasmid vectors comprising a CMV promoter upstream of polynucleotides that encode fragments of the extracellular Notch1 domain as Fc fusion proteins are generated using standard recombinant DNA technology. In certain embodiments, epitope mapping of the 52M series of non-ligand binding region antibodies is done using a series of fusion proteins and deletions of the membrane proximal region of the extracellular domain of a human Notch1 from about amino acid 1427 to about amino acid 1732. These recombinant fusion proteins are expressed in transiently transfected HEK 293 cells from which conditioned medium is collected twenty-four to forty-eight hours post-transfection for ELISA.

In certain embodiments, the Notch1 fusion protein fragments are separated on SDS-PAGE gels and probed with both anti-Fc antibodies to detect the presence of all fusion proteins versus anti-Notch1 antibodies to detect the domains recognized by each anti-Notch antibody.

To identify specific epitopes within the extracellular domains recognized by an antibody against Notch1 the SPOTs system is used (Sigma Genosys, The Woodlands, Tex.). A series of 10-residue linear peptides overlapping by one amino acid and covering the entire Notch1 extracellular domain are synthesized and covalently bound to a cellulose membrane by the SPOT synthesis technique. The membrane is preincubated for 8 hours at room temperature with blocking buffer and hybridized with antibody overnight at 4° C. The membrane is then washed, incubated with a secondary antibody conjugated to horseradish peroxidase (HRP) (Amersham Bioscience, Piscataway, N.J.), re-washed, and visualized with signal development solution containing 3-amino-9-ethylcarbazole. Specific epitopes recognized by an antibody are thus determined.

Chimeric Antibodies

After monoclonal antibodies that specifically recognize a non-ligand binding membrane proximal domain of the extracellular domain of a Notch1 receptor are identified, these antibodies are modified to overcome the human anti-mouse antibody (HAMA) immune response when rodent antibodies are used as therapeutics agents. The variable regions of the heavy-chain and light-chain of the selected monoclonal antibody are isolated by RT-PCR from hybridoma cells and ligated in-frame to human IgG1 heavy-chain and kappa light chain constant regions, respectively, in mammalian expression vectors. Alternatively a human Ig expression vector such as TCAE 5.3 is used that contains the human IgG1 heavy-chain and kappa light-chain constant region genes on the same plasmid (Preston et al., 1998, *Infection & Immunity* 66:4137-42). Expression vectors encoding chimeric heavy- and light-chains are then co-transfected into Chinese hamster ovary (CHO) cells for chimeric antibody production. Immunoreactivity and affinity of chimeric antibodies are compared to parental murine antibodies by ELISA and FACS.

Humanized Antibodies

As chimeric antibody therapeutics are still frequently antigenic, producing a human anti-chimeric antibody (HACA) immune response, chimeric antibodies against a non-ligand binding membrane proximal domain of the extracellular domain of a Notch1 receptor can require further humanization. To generate humanized antibodies the three short hypervariable sequences, or complementary determining regions (CDRs), of the chimeric antibody heavy- and light-chain variable domains described above are engineered using recombinant DNA technology into the variable domain framework of a human heavy- and light-chain sequences, respectively, and then cloned into a mammalian expression vector for expression in CHO cells. The immunoreactivity and affinity of the humanized antibodies are compared to parental chimeric antibodies by ELISA and FACS. Additionally, site-directed or high-density mutagenesis of the variable region can be used to optimize specificity, affinity, etc. of the humanized antibody.

Example 2

Humanized antibodies against a membrane proximal region of the extracellular domain of a human Notch1 were generated. The variable domains of the murine monoclonal antibody 52M51 were isolated and sequenced from the hybridoma line using degenerate PCR essentially as described in Larrick, J. M., et al., 1989, *Biochem. Biophys. Res. Comm.* 160: 1250 and Jones, S. T. & Bendig, M. M., 1991, *Bio/Technology* 9: 88. Human heavy and light chain variable framework regions likely to be structurally similar to the parental 52M51 antibody amino acid sequences are then considered as reference human framework regions to help guide the design of novel synthetic frameworks. To identify the human framework regions bearing similarity to 52M51 murine frameworks, the predicted protein sequences encoded by the $V_H$ and $V_L$ murine variable domains of 52M51 are compared with human antibody sequences encoded by expressed human cDNA using BLAST searches for human sequence deposited in Genbank. Using this method, expressed human cDNA sequences (e.g. genbank DA975021, DB242412) and germline Vh domains (e.g. IGHV1-24) were selected for further analysis in designing heavy chain frameworks. Similarly, expressed human cDNA sequences (e.g. genbank CD709370, CD707373) and germline Vl (e.g. IGLV7-46, IGLV8-61) were considered in designing light chain frameworks.

The amino acid differences between candidate humanized framework heavy chains and the parent murine monoclonal antibody 52M51 heavy chain variable domain and light chain variable domains were evaluated for likely importance, and a judgment made as to whether each difference in position contributes to proper folding and function of the variable domain. This analysis was guided by examination of solved crystal structures of other antibody fragments (e.g., the structure of Fab 2E8 as described in Trakhanov et al, *Acta Crystallogr D Biol Crystallogr,* 1999, 55:122-28, as well as other protein crystal structures (e.g., protein data bank structures 1ADQ and 1GIG)). Structures were modeled using computer software including Jmol, quick PDB, and Pymol. Consideration was given to the potential impact of an amino acid at a given position on the packing of the β-sheet framework, the interaction between the heavy and light chain variable domains, the degree of solvent exposure of the amino acid side chain, and the likelihood that an amino acid would impact the positioning of the CDR loops. From this analysis, nine candidate $V_H$ chains fused in-frame to the human IgG2 constant region and eight candidate Vl chains fused in frame with the human IgLC1 constant region were conceived and chemically synthesized. The candidate heavy chains comprise: i) a synthetic framework designed to resemble natural human frameworks and ii) the parental 52M51 murine antibody CDRs.

The functionality of each candidate variant humanized heavy and light chain was tested by cotransfection into mammalian cells. Each of the nine candidate humanized 52M51 heavy chains described above was cotransfected into HEK 293 cells with the murine 52M51 light chain cDNA, and conditioned media was assayed by ELISA for Notch1 binding activity. The 52M51 heavy chain variant exhibiting the most robust binding was selected. This variant "52M51-H4" (SEQ ID NO:22) contains, in addition to murine CDRs, variation at 3 framework positions within the Vh framework, Kabat positions 20, 48, and 71 in comparison with an example human framework (e.g. IGHV1-24). The 52M51-H4 humanized heavy chain was then cotransfected into HEK293 cells with each of the eight candidate humanized light chains, and conditioned media was again assayed for antigen binding by ELISA. Two light chain variants "2M51 L3" (SEQ ID NO:26) and "52M51 L4" (SEQ ID NO:30) were found to exhibit better binding than the other candidates and were chosen for further study. Variant 52M51-L3 contains, in addition to murine CDRs, variation at 1 framework position at Kabat position 49 in comparison to an example human framework (e.g., IGLV7-46). Two humanized variant antibodies, 52M51H4L3 and 52M51H4L4, were developed. 52M51H4L3, as encoded by DNA deposited with the ATCC, under the conditions of the Budapest Treaty on Oct. 15, 2008, and assigned designation number PTA-9549.

The affinities for human and mouse Notch1 were determined using a Biacore 2000 instrument. Briefly, recombinant human and mouse Notch1 proteins were immobilized on a CM5 chip using standard amine based chemistry (NHS/EDC). Different antibody concentrations were injected over the protein surfaces and kinetic data were collected over time. The data was fit using the simultaneous global fit equation to yield dissociation constants ($K_D$, nM) for each Notch1 (Table 2).

TABLE 2

| IgG Dissociation Constants ($K_D$) | | |
|---|---|---|
| Antibody | Human Notch1 (nM) | Mouse Notch1 (nM) |
| 52M51 | 2.86 | NB |
| 52M51H4L3 | 4.33 | NB |
| 52M51H4L4 | 7.35 | NB |

Example 3

Notch Receptor Signaling

In certain embodiments, the ability of Notch1 receptor antibodies to block ligand-mediated Notch signaling was determined. In certain embodiments, HeLa cells engineered to overexpress Notch1 (Notch1-Hela) cultured in DMEM supplemented with antibiotics and 10% FCS were co-transfected with 1) pGL4 8×CBS firefly luciferase containing a Notch responsive promoter upstream of a firefly luciferase reporter gene to measure Notch signaling levels in response to DLL4 ligand; and 2) a *Renilla luciferase* reporter (Promega; Madison, Wis.) as an internal control for transfection efficiency. Transfected cells were added to cultures plates coated overnight with 200 ng/well of hDLL4-fc protein, and antibodies to Notch1 were then added to the cell culture medium. Forty-eight hours following transfection, luciferase levels were measured using a dual luciferase assay kit (Promega; Madison, Wis.) with firefly luciferase activity normalized to *Renilla luciferase* activity. The ability of antibodies to inhibit Notch1 pathway activation was thus determined. Antibodies 52M51, 52M63, 52M74, and 52M80, generated against a membrane proximal region of the extracellular domain of a human Notch1 (FIG. 1A) significantly reduced luciferase activity indicative of reduced Notch1 signaling as compared to other Notch1 antibodies (FIG. 1B). Further, a humanized variant of antibody 52M51, variant 52M51 H4/L3 displayed similar potency in reducing luciferase activity (FIG. 1C).

Notch Receptor Activation and ICD Formation

Cleavage of Notch receptors by furin, ADAM, and gamma-secretase results in formation of the Notch intracellular domain (ICD) that then triggers downstream Notch signaling in the nucleus. In certain embodiments, the ability of Notch1 receptor antibodies to block ligand-mediated receptor activation was determined by Western blot analysis. Notch1-Hela cells were grown in suspension culture in 293-SMII media (Gibco). Cultured cells were transferred to 96-well plates in which select wells had been pre-coated with human DLL4-fc fusion protein (2 µg/ml) in DMEM plus 2% FBS and 1 µM MG132 (Calbiochem). Antibodies to generated against a membrane proximal region of the extracellular domain of human Notch1 were added to the cell culture medium, and cells were incubated at 37° C. for five hours. Wells were then aspirated and the cells resuspended in 2×SDS running buffer. Samples were sonicated at room temperature, and then subjected to SDS-PAGE and western blot analysis using an antibody specific for the cleaved Notch1 ICD according to the manufacturer's recommendations (Cell Signaling Technology). 52M51 along with 52M63, 52M74, and 52M80 all significantly inhibited the generation of ICD after ligand stimulation (FIG. 1D).

Example 4

In vivo Prevention of Tumor Growth Using Non-Ligand Binding Region Anti-Notch Receptor Antibodies Tumor cells from a patient sample that have been passaged as a xenograft in mice were prepared for injection into experimental animals. Tumors were established at OncoMed Pharmaceuticals by adhering to procedures described previously (See Al-Hajj et al., 2003; Dalerba et al., 2007) and include: UM-PE13 and T3 (breast carcinoma cells), OMP-C9, OMP-C8, OMP-C6, and Colo-205 (colon tumor cells); and OMP-PN4 (pancreatic carcinoma cells). Tumor tissue was removed under sterile conditions, cut up into small pieces, minced completely using sterile blades, and single cell suspensions obtained by enzymatic digestion and mechanical disruption. The resulting tumor pieces were mixed with ultra-pure collagenase III in culture medium (200-250 units of collagenase per mL) and incubated at 37° C. for 3-4 hours with pipetting up and down through a 10-mL pipette every 15-20 min. Digested cells were filtered through a 45 ul nylon mesh, washed with RPMI/20% FBS, and washed twice with HBSS. Dissociated tumor cells were then injected subcutaneously into NOD/SCID mice at 6-8 weeks to elicit tumor growth. For UM-PE13 and T3 breast tumor cells, 50,000 cells in 100 ul were injected into the right mammary fat pad (n=20) along with the implantation of an estrogen pellet. For OMP-C9 colon tumor cells, 50,000 cells in 100 ul were injected into the right flank region (n=20). For OMP-C8 colon tumor cells, 10,000 cells in 100 ul were injected into the right flank area (n=10). For OMP-C6 colon tumor cells, 10,000 cells in 100 ul were injected into the right flank (n=10). All tumor cells were injected in a mixture of PBS (without magnesium or calcium) and BD Matrigel (BD Biosciences) at a 1:1 ratio.

Three days after tumor cell injection, antibody treatment was commenced. Each injected animal received 10 mg/kg anti-Notch1 antibodies or PBS as a control intraperitoneal (i.p.) two times per week for a total of 6 to 8 weeks. Animals injected with PE13 cells received injections into the right upper mammary fat pad in addition to estrogen pellet injections. Animals injected with C9, C8, or C6 cells received injections in the right lower quadrant of the abdomen. Tumor size was assessed twice a week.

In certain embodiments, antibodies against a membrane proximal region of the extracellular domain of human Notch1 were tested for an effect on the formation of breast tumors. PE13 breast tumor cells (50,000 cells per injection) were implanted subcutaneously into the mammary fat pads. Two days following cell implantation, animals were treated with either control antibody or 52M antibodies 52M1, 52M2, and 52M8 (which were without anti-Notch signaling capability, see FIG. 1B) at 10 mg/kg dosed i.p. twice a week. Treatment with non-Notch1 inhibitor antibodies had no effect on tumor growth compared to control treated animals (FIGS. 2C and 2D). In certain embodiments, animals injected with PE13 breast tumor cells are treated with either control antibody or 52M51 at 10 mg/kg dosed i.p. twice a week. Tumor volume is measured twice weekly, and the effect of 52M51 on breast tumor growth is determined.

In alternative embodiments, dissociated tumor cells are first sorted into tumorigenic and non-tumorigenic cells based on cell surface markers before injection into experimental animals. Specifically, tumor cells dissociated as described above are washed twice with Hepes buffered saline solution (HBSS) containing 2% heat-inactivated calf serum (HICS) and resuspended at $10^6$ cells per 100 ul. Antibodies are added and the cells incubated for 20 min on ice followed by two washes with HBSS/2% HICS. Antibodies include anti-ESA (Biomeda, Foster City, Calif.), anti-CD44, anti-CD24, and Lineage markers anti-CD2, -CD3, -CD10, -CD16, -CD18, -CD31, -CD64, and -CD140b (collectively referred to as Lin; PharMingen, San Jose, Calif.). Antibodies are directly conjugated to fluorochromes to positively or negatively select cells expressing these markers. Mouse cells are eliminated by selecting against H2Kd+ cells, and dead cells are eliminated by using the viability dye 7AAD. Flow cytometry is performed on a FACSVantage (Becton Dickinson, Franklin Lakes, N.J.). Side scatter and forward scatter profiles are used to eliminate cell clumps. Isolated ESA+, CD44+, CD24−/low, Lin-tumorigenic cells are then injected subcutaneously into NOD/SCID mice to elicit tumor growth.

Example 5

In vivo Treatment of Tumors Using Anti-Notch1 Receptor Antibodies

Tumor cells from a patient sample (solid tumor biopsy or pleural effusion) that have been passaged as a xenograft in mice were prepared for repassaging into experimental animals. Tumor tissue was removed, cut up into small pieces, minced completely using sterile blades, and single cell suspensions obtained by enzymatic digestion and mechanical disruption. Dissociated tumor cells were then injected subcutaneously into the mammary fat pads, for breast tumors, or into the flank, for non-breast tumors, of NOD/SCID mice to elicit tumor growth. In certain embodiments, ESA+, CD44+, CD24−/low, Lin-tumorigenic tumor cells are isolated as described in detail above and injected.

In certain embodiments, freshly isolated C8 colon tumor cells (225 cells per animal) were implanted subcutaneously into NOD/SCID mice. Following tumor cell injection, animals were monitored for tumor growth. Tumors were allowed to grow for 48 days until they reached an average size of approximately 210 mm$^3$ and randomized into two groups (n=10 per group). The animals were treated with either control antibody or antibody that binds to the membrane proximal region of the extracellular domain of human Notch1, 52M51, (10 mg/kg) dosed i.p. twice a week. Tumor size was assessed on days 55, 57, and 62. Animals treated with 52M51 showed a statistically significant (p=0.0006) inhibition of tumor growth compared to control treated animals (FIGS. 2A and 2B).

At the end point of antibody treatment, tumors are harvested for further analysis. In some embodiments, a portion of the tumor is analyzed by immunofluorescence to assess antibody penetration into the tumor and tumor response. A portion of each harvested tumor from anti-Notch1 receptor treated and control antibody treated mice is flash-frozen in liquid nitrogen, embedded in O.C.T., and cut on a cryostat as 10 um sections onto glass slides. Alternatively a portion of each tumor is formalin-fixed, paraffin-embedded, and cut on a microtome as 10 um section onto glass slides. Sections are post-fixed and incubated with chromophore labeled antibodies that specifically recognize injected antibodies to detect anti-NOTCH1 receptor or control antibodies present in the tumor biopsy. Furthermore antibodies that detect different tumor and tumor recruited cell types such as, for example, anti-VE cadherin (CD144) or anti-PECAM-1 (CD31) antibodies to detect vascular endothelial cells, anti-smooth muscle alpha-actin antibodies detect vascular smooth muscle cells, anti-Ki67 antibodies to detect proliferating cells, TUNEL assays to detect dying cells, and anti-intracellular domain (ICD) Notch fragment antibodies to detect Notch signaling can be used to assess affects of antibody treatment on angiogenesis, tumor growth and tumor morphology.

The effect of anti-Notch1 receptor antibody treatment on tumor cell gene expression is also assessed. Total RNA is extracted from a portion of each harvested tumor from Notch1 antibody treated and control antibody treated mice and used for quantitative RT-PCR. Expression levels of Notch1, components of Notch signaling pathway including, as well as addition cancer stem cell markers previously identified including, for example, CD44 are analyzed relative to the house-keeping gene GAPDH as an internal control. Changes in tumor cell gene expression upon Notch1 receptor antibody treatment are thus determined.

In addition, the effect of anti-Notch1 receptor antibody treatment on the presence of cancer stem cells in a tumor is assessed. Tumor samples from Notch1 versus control antibody treated mice are cut up into small pieces, minced completely using sterile blades, and single cell suspensions obtained by enzymatic digestion and mechanical disruption. Dissociated tumor cells are then analyzed by FACS analysis for the presence of tumorigenic cancer stem cells based on ESA+, CD44+, CD24−/low, Lin-surface cell marker expression as described in detail above.

The tumorigenicity of cells isolated based on ESA+, CD44+, CD24−/low, Lin-expression following anti-Notch1 antibody treatment can then be assessed. 5,000, 1,000, 500, and 100 isolated ESA+, CD44+, CD24−/low, Lin-cancer stem cells from Notch1 antibody treated versus control antibody treated mice are re-injected subcutaneously into the mammary fat pads of NOD/SCID mice. The tumorigenicity of cancer stem cells based on the number of injected cells required for consistent tumor formation is thus determined.

In contrast to the in vivo efficacy of 52M51, an antibody that inhibits Notch1 signaling, in a colon xenograft model described above, certain other antibodies that recognize the membrane proximal region of Notch 1, but don't inhibit Notch 1 signaling, were found to not have anti-tumor efficacy in vivo in a breast xenograft model. The antibodies 52M51, 52M2, and 52M8, each of which had been found to not appreciably inhibit Notch signaling (Example 3 and FIG. 1B), were injected in NOD/SCID mice which had been previously injected with PE13 breast tumor cells. Each of the antibodies 52M1, 52M2, and 52M8 failed to effect tumor growth in the xenograft model when compared against control-treated animals (FIG. 2C (52M1, 52M2) and FIG. 2D (52M8)).

Example 6

Treatment of Human Cancer Using Anti-Notch Receptor Antibodies

This example describes methods for treating cancer using antibodies against a Notch receptor to target tumors comprising cancer stem cells and/or tumor cells in which Notch receptor expression has been detected.

The presence of cancer stem cell marker expression can first be determined from a tumor biopsy. Tumor cells from a biopsy from a patient diagnosed with cancer are removed under sterile conditions. In some embodiments, the tissue biopsy is fresh-frozen in liquid nitrogen, embedded in O.C.T., and cut on a cryostat as 10 um sections onto glass slides. Alternatively the tissue biopsy is formalin-fixed, paraffin-embedded, and cut on a microtome as 10 um section onto glass slides. Sections are incubated with antibodies against a Notch receptor to detect protein expression. Additionally, the presence of cancer stem cells can be determined. Tissue biopsy samples are cut up into small pieces, minced completely using sterile blades, and cells subject to enzymatic digestion and mechanical disruption to obtain a single cell suspension. Dissociated tumor cells are then incubated with anti-ESA, -CD44, -CD24, -Lin, and -Notch1 antibodies to detect cancer stem cells, and the presence of ESA+, CD44+, CD24−/low, Lin−, Notch+ tumor stem cells is determined by flow cytometry as described in detail above.

Cancer patients whose tumors are diagnosed as expressing a Notch receptor are treated with anti-Notch receptor antibodies. Humanized or human monoclonal anti-Notch receptor antibodies generated as described above are purified and formulated with a suitable pharmaceutical carrier in PBS for injection. Patients are treated with the Notch antibodies once a week for at least 10 weeks, but in certain cases once a week for at least about 14 weeks. Each administration of the antibody should be a pharmaceutically effective dose about 2 to about 100 mg/ml and in certain cases between about 5 to about 40 mg/ml. The antibody can be administered prior to, concurrently with, or after standard radiotherapy regimens or chemotherapy regimens using one or more chemotherapeutic agent, such as oxaliplatin, fluorouracil, leucovorin, or streptozocin. Patients are monitored to determine whether such treatment has resulted in an anti-tumor response, for example, based on tumor regression, reduction in the incidences of new tumors, lower tumor antigen expression, decreased numbers of cancer stem cells, or other means of evaluating disease prognosis.

Example 7

Additional Studies of in vivo Treatment of Tumors Using Anti-Notch1 Receptor Antibodies In one embodiment, M2 melanoma cells (10,000) were injected subcutaneously in NOD-SCID mice. Tumors were allowed to grow for 35 days until they had reached a volume of approximately 110 mm$^3$. Tumor-bearing mice were randomized into two groups (n=10) and treated with either control antibody or anti-Notch1 antibody 52R43. Antibodies were dosed twice weekly at 10 mg/kg. Tumor volumes were measured on the indicated days. As shown in FIG. 3A, anti-Notch1 treatment with 52R43 reduced tumor growth relative to the control group (p=0.02).

In one embodiment, Lu24 lung tumor cells (30,000) were injected subcutaneously in NOD-SCID mice. Tumors were allowed to grow for 35 days until they had reached a volume of approximately 205 mm$^3$. Tumor-bearing mice were randomized into two groups (n=8) and treated with either control antibody or anti-Notch1 antibody 52R43. Antibodies were dosed twice weekly at 10 mg/kg. Tumor volumes were measured on the indicated days. As shown in FIG. 3B, anti-Notch1 treatment with 52R43 reduced tumor growth relative to the control group (p=0.04).

In one embodiment, PN8 pancreatic tumor cells (50,000) were injected subcutaneously in NOD-SCID mice. Tumors were allowed to grow for 27 days until they had reached a volume of approximately 115 mm$^3$. Tumor bearing mice were randomized into two groups (n=8) and treated with either control antibody or anti-Notch1 antibody 52R43. Antibodies were dosed twice weekly at 10 mg/kg. Tumor volumes were measured on the indicated days. As shown in FIG. 3C, anti-Notch1 treatment with 52R43 reduced tumor growth relative to the control group (p=0.005).

In one embodiment, T1 breast tumor cells (300,000) were injected subcutaneously in NOD-SCID mice. Tumors were allowed to grow for 27 days until they had reached a volume of approximately 130 mm$^3$. Tumor bearing mice were randomized into four groups (n=10) and treated with either control antibody, anti-Notch1 52R43, taxol, or a combination of 52R43 and taxol. Antibodies were dosed once weekly at 15 mg/kg and taxol was dosed once weekly at 12 mg/kg. Tumor volumes were measured on the indicated days. As shown in FIG. 3D, anti-Notch1 treatment with 52R43 reduced tumor growth relative to the control group (p<0.0001), and the combination group was reduced relative to taxol alone (p=0.001)

All publications and patents mentioned in the above specification are herein incorporated by reference. Various modifications and variations of the described method and system of the invention will be apparent to those in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those in the relevant fields are intended to be within the scope of the following claims.

```
                                 SEQUENCES

SEQ ID NO: 1
Notch1 Polynucleotide encoding amino acids 1427-1732.
CACATCCTGGACTACAGCTTCGGGGGTGGGGCCGGGCGCGACATCCCCCGCCGCTGATC
GAGGAGGCGTGCGAGCTGCCCGAGTGCCAGGAGGACGCGGGCAACAAGGTCTGCAGCCTG
CAGTGCAACAACCACGCGTGCGGCTGGGACGGCGGTGACTGCTCCCTCAACTTCAATGAC
CCCTGGAAGAACTGCACGCAGTCTCTGCAGTGCTGGAAGTACTTCAGTGACGGCCACTGT
GACAGCCAGTGCAACTCAGCCGGCTGCCTCTTCGACGGCTTTGACTGCCAGCGTGCGGAA
```

```
GGCCAGTGCAACCCCCTGTACGACCAGTACTGCAAGGACCACTTCAGCGACGGGCACTGC
GACCAGGGCTGCAACAGCGCGGAGTGCGAGTGGGACGGGCTGGACTGTGCGGAGCATGTA
CCCGAGAGGCTGGCGGCCGGCACGCTGGTGGTGGTGGTGCTGATGCCGCCGGAGCAGCTG
CGCAACAGCTCCTTCCACTTCCTGCGGGAGCTCAGCCGCGTGCTGCACACCAACGTGGTC
TTCAAGCGTGACGCACACGGCCAGCAGATGATCTTCCCCTACTACGGCCGCGAGGAGGAG
CTGCGCAAGCACCCCATCAAGCGTGCCGCCGAGGGCTGGGCCGCACCTGACGCCCTGCTG
GGCCAGGTGAAGGCCTCGCTGCTCCCTGGTGGCAGCGAGGGTGGCGGCGGCGGAGGGAG
CTGGACCCCATGGACGTCCGCGGCTCCATCGTCTACCTGGAGATTGACAACCGGCAGTGT
GTGCAGGCCTCCTCGCAGTGCTTCCAGAGTGCCACCGACGTGGCCGCATTCCTGGGAGCG
CTCGCCTCGCTGGGCAGCCTCAACATCCCCTACAAGATCGAGGCCGTGCAGAGTGAGACC
GTGGAGCCGCCCCCGCCG

SEQ ID NO: 2
Notch1 amino acids 1427-1732
HILDYSFGGGAGRDIPPPLIEEACELPECQEDAGNKVCSLQCNNHACGWDGGDCSLNFND
PWKNCTQSLQCWKYFSDGHCDSQCNSAGCLFDGFDCQRAEGQCNPLYDQYCKDHFSDGHC
DQGCNSAECEWDGLDCAEHVPERLAAGTLVVVVLMPPEQLRNSSFHFLRELSRVLHTNVV
FKRDAHGQQMIFPYYGREEELRKHPIKRAAEGWAAPDALLGQVKASLLPGGSEGGRRRRE
LDPMDVRGSIVYLEIDNRQCVQASSQCFQSATDVAAFLGALASLGSLNIPYKIEAVQSET
VEPPPP
```

Mouse antibody 52M51 sequences:

```
SEQ ID NO: 3
52M51 Light chain polynucleotide sequence
(Putative signal sequence is underlined)
ATGGCCTGGATTTCACTTATACTCTCTCCTGGCTCTCAGCTCAGGGGCCATTTCCCAG
GCTGTTGTGACTCAGGAATCTGCACTCACCACATCACCTGGTGAAACAGTCACACTCACT
TGTCGCTCAAGTACTGGGGCTGTTACAACTAGTAACTACGCCAACTGGGTCCAAGAAAAA
CCTGATCATTTATTCACTGGTCTAATAGGTGGTACCAACAACCGAGCTCCAGGTGTTCCT
GCCAGATTCTCAGGCTCCCTGATTGGAGACAAGGCTGCCCTCACCATCACAGGGGCACAG
ACTGAGGATGAGGCAATATATTTCTGTGCTCTATGGTACAGCAACCACTGGGTGTTCGGT
GGAGGAACCAAACTGACTGTCCTAGGCCAGCCCAAGTCTTCGCCATCAGTCACCCTGTTT
CCACCTTCCTCTGAAGAGCTCGAGACTAACAAGGCCACACTGGTGTGTACGATCACTGAT
TTCTACCCAGGTGTGGTGACAGTGGACTGGAAGGTAGATGGTACCCCTGTCACTCAGGGT
ATGGAGACAACCCAGCCTTCCAAACAGAGCAACAACAAGTACATGGCTAGCAGCTACCTG
ACCCTGACAGCAAGAGCATGGGAAAGGCATAGCAGTTACAGCTGCCAGGTCACTCATGAA
GGTCACACTGTGGAGAAGAGTTTGTCCCGTGCTGACTGTTCCTAG SEQ ID NO: 4
52M51 Light chain amino acid sequence
(Putative signal sequence is underlined)
MAWISLILSLLALSSGAISQAVVTQESALTTSPGETVTLTCRSSTGAVTTSNYANWVQEK
PDHLFTGLIGGTNNRAPGVPARFSGSLIGDKAALTITGAQTEDEAIYFCALWYSNHWVFG
GGTKLTVLGQPKSSPSVTLFPPSSEELETNKATLVCTITDFYPGVVTVDWKVDGTPVTQG
METTQPSKQSNNKYMASSYLTLTARAWERHSSYSCQVTHEGHTVEKSLSRADCS SEQ ID NO: 5
52M51 Light chain variable region polynucleotide sequence
(Putative signal sequence is underlined)
ATGGCCTGGATTTCACTTATACTCTCTCCTGGCTCTCAGCTCAGGGGCCATTTCCCAG
GCTGTTGTGACTCAGGAATCTGCACTCACCACATCACCTGGTGAAACAGTCACACTCACT
TGTCGCTCAAGTACTGGGGCTGTTACAACTAGTAACTACGCCAACTGGGTCCAAGAAAAA
CCTGATCATTTATTCACTGGTCTAATAGGTGGTACCAACAACCGAGCTCCAGGTGTTCCT
GCCAGATTCTCAGGCTCCCTGATTGGAGACAAGGCTGCCCTCACCATCACAGGGGCACAG
ACTGAGGATGAGGCAATATATTTCTGTGCTCTATGGTACAGCAACCACTGGGTGTTCGGT
GGAGGAACCAAACTGACTGTCCTAGGC SEQ ID NO: 6
52M51 Light chain variable region amino acid sequence
(Putative signal sequence is underlined)
MAWISLILSLLALSSGAISQAVVTQESALTTSPGETVTLTCRSSTGAVTTSNYANWVQEK
PDHLFTGLIGGTNNRAPGVPARFSGSLIGDKAALTITGAQTEDEAIYFCALWYSNHWVFG
GGTKLTVLGQPKSSPSVTLFPPSSEELETNKATLVCTITDFYPGVVTVDWKVDGTPVTQG SEQ ID NO: 7
52M51 Light chain variable region polynucleotide sequence
without putative signal sequence
CAGGCTGTTGTGACTCAGGAATCTGCACTCACCACATCACCTGGTGAAACAGTCACACTC
ACTTGTCGCTCAAGTACTGGGGCTGTTACAACTAGTAACTACGCCAACTGGGTCCAAGAA
AAACCTGATCATTTATTCACTGGTCTAATAGGTGGTACCAACAACCGAGCTCCAGGTGTT
CCTGCCAGATTCTCAGGCTCCCTGATTGGAGACAAGGCTGCCCTCACCATCACAGGGGCA
CAGACTGAGGATGAGGCAATATATTTCTGTGCTCTATGGTACAGCAACCACTGGGTGTTC
GGTGGAGGAACCAAACTGACTGTCCTAGGC
```

SEQ ID NO: 8
52M51 Light chain variable region amino acid sequence
without putative signal sequence
QAVVTQESALTTSPGETVTLTCRSSTGAVTTSNYANWVQEKPDHLFTGLIGGTNNRAPGV
PARFSGSLIGDKAALTITGAQTEDEAIYFCALWYSNHWVFGGGTKLTVLG SEQ ID NO: 9
52M51 Heavy chain polynucleotide sequence
(Putative signal sequence is underlined)
<u>ATGGAATGGACCTGGGTCTTTCTCTTCCTCCTGTCAGTAACTGCAGGTGTCCACTCCCAG</u>
GTTCAGCTGCAGCAGTCTGGAGCTGAGCTGATGAAGCCTGGGGCCTCAGTGAAGATATCC
TGCAAGGCTGCTGGCTACACAATGAGAGGCTACTGGATAGAGTGGATAAAGCAGAGGCCT
GGACATGGCCTTGAGTGGATTGGACAGATTTTACCTGGAACTGGGAGAACTAACTACAAT
GAGAAGTTCAAGGGCAAGGCCACATTCACTGCAGATACATCCTCCAACACAGCCAACATG
CAACTCAGCAGCCTGACATCTGAGGACTCTGCCGTCTATTACTGTGCAAGATTTGATGGT
AACTACGGTTACTATGCTATGGACTACTGGGGTCAAGGATCCTCAGTCACCGTCTCCTCA
GCCAAAACGACACCCCCATCTGTCTATCCACTGGCCCCTGGATCTGCTGCCCAAACTAAC
TCCATGGTGACCCTGGGATGCCTGGTCAAGGGCTATTTCCCTGAGCCAGTGACAGTGACC
TGGAACTCTGGATCCCTGTCCAGCGGTGTGCACACCTTCCCAGCTGTCCTGCAGTCTGAC
CTCTACACTCTGAGCAGCTCAGTGACTGTCCCCTCCAGCCCTCGGCCCAGCGAGACCGTC
ACCTGCAACGTTGCCCACCCGGCCAGCAGCACCAAGGTGGACAAGAAATTGTGCCCAGG
GATTGTGGTTGTAAGCCTTGCATATGTACAGTCCCAGAAGTATCATCTGTCTTCATCTTC
CCCCCAAAGCCCAAGGATGTCCTCACCATTACTCTGACTCCTAAGGTCACGTGTGTTGTG
GTAGACATCAGCAAGGATGATCCCGAGGTCCAGTTCAGCTGGTTTGTAGATGATGTGGAG
GTGCACACAGCTCAGACGCAACCCGGGAGGAGCAGTTCAACAGCACTTTCCGCTCAGTC
AGTGAACTTCCCATCATGCACCAGGACTGGCTCAATGGCAAGGAGTTCAAATGCAGGGTC
AACAGTGCAGCTTTCCCTGCCCCCATCGAGAAAACCATATCCAAAACCAAAGGCAGACCG
AAGGCTCCACAGGTGTACACCATTCCACCTCCCAAGGAGCAGATGGCCAAGGATAAAGTC
AGTCTGACCTGCATGATAACAGACTTCTTCCCTGAAGACATAACAGTGGAGTGGCAGTGG
AATGGGCAGCCAGCGGAGAACTACAAGAACACTCAGCCCATCATGAACACGAATGGCTCT
TACTTCGTCTACAGCAAGCTCAATGTGCAGAAGAGCAACTGGGAGGCAGGAAATACTTTC
ACCTGCTCTGTGTTACATGAGGGCCTGCACAACCACCATACTGAGAAGAGCCTCTCCCAC
TCTCCTGGTAAATGA SEQ ID NO: 10
52M51 Heavy chain amino acid sequence
(Putative signal sequence is underlined)
<u>MEWTWVFLFLLSVTAGVHS</u>QVQLQQSGAELMKPGASVKISCKAAGYTMRGYWIEWIKQRP
GHGLEWIGQILPGTGRTNYNEKFKGKATFTADTSSNTANMQLSSLTSEDSAVYYCARFDG
NYGYYAMDYWGQGSSVTVSSAKTTPPSVYPLAPGSAAQTNSMVTLGCLVKGYFPEPVTVT
WNSGSLSSGVHTFPAVLQSDLYTLSSSVTVPSSPRPSETVTCNVAHPASSTKVDKKIVPR
DCGCKPCICTVPEVSSVFIFPPKPKDVLTITLTPKVTCVVVDISKDDPEVQFSWFVDDVE
VHTAQTQPREEQFNSTFRSVSELPIMHQDWLNGKEFKCRVNSAAFPAPIEKTISKTKGRP
KAPQVYTIPPPKEQMAKDKVSLTCMITDFFPEDITVEWQWNGQPAENYKNTQPIMNTNGS
YFVYSKLNVQKSNWEAGNTFTCSVLHEGLHNHHTEKSLSHSPGK SEQ ID NO: 11
52M51 Heavy chain variable region polynucleotide sequence
(Putative signal sequence is underlined)
<u>ATGGAATGGACCTGGGTCTTTCTCTTCCTCCTGTCAGTAACTGCAGGTGTCCACTCCCAG</u>
GTTCAGCTGCAGCAGTCTGGAGCTGAGCTGATGAAGCCTGGGGCCTCAGTGAAGATATCC
TGCAAGGCTGCTGGCTACACAATGAGAGGCTACTGGATAGAGTGGATAAAGCAGAGGCCT
GGACATGGCCTTGAGTGGATTGGACAGATTTTACCTGGAACTGGGAGAACTAACTACAAT
GAGAAGTTCAAGGGCAAGGCCACATTCACTGCAGATACATCCTCCAACACAGCCAACATG
CAACTCAGCAGCCTGACATCTGAGGACTCTGCCGTCTATTACTGTGCAAGATTTGATGGT
AACTACGGTTACTATGCTATGGACTACTGGGGTCAAGGATCCTCAGTCACCGTCTCCTCA SEQ ID NO: 12
52M51 Heavy chain variable region amino acid sequence
(Putative signal sequence is underlined)
<u>MEWTWVFLFLLSVTAGVHS</u>QVQLQQSGAELMKPGASVKISCKAAGYTMRGYWIEWIKQRP
GHGLEWIGQILPGTGRTNYNEKFKGKATFTADTSSNTANMQLSSLTSEDSAVYYCARFDG
NYGYYAMDYWGQGSSVTVSSAKTTPPSVYPLAPGSAAQTNVTLGCLVKGYFPEPVTVT SEQ ID NO: 13
52M51 Heavy chain variable region polynucleotide sequence
without putative signal sequence
CAGGTTCAGCTGCAGCAGTCTGGAGCTGAGCTGATGAAGCCTGGGGCCTCAGTGAAGATA
TCCTGCAAGGCTGCTGGCTACACAATGAGAGGCTACTGGATAGAGTGGATAAAGCAGAGG
CCTGGACATGGCCTTGAGTGGATTGGACAGATTTTACCTGGAACTGGGAGAACTAACTAC
AATGAGAAGTTCAAGGGCAAGGCCACATTCACTGCAGATACATCCTCCAACACAGCCAAC
ATGCAACTCAGCAGCCTGACATCTGAGGACTCTGCCGTCTATTACTGTGCAAGATTTGAT
GGTAACTACGGTTACTATGCTATGGACTACTGGGGTCAAGGATCCTCAGTCACCGTCTCC
TCA

SEQUENCES

SEQ ID NO: 14
52M51 Heavy chain variable region amino acid sequence
without putative signal sequence
QVQLQQSGAELMKPGASVKISCKAAGYTMRGYWIEWIKQRPGHGLEWIGQILPGTGRTNY
NEKFKGKATFTADTSSNTANMQLSSLTSEDSAVYYCARFDGNYGYYAMDYWGQGSSVTVS
SA SEQ ID NO: 15
52M51 Heavy chain CDR1
RGYWIE SEQ ID NO: 16
52M51 Heavy chain CDR2
QILPGTGRTNYNEKFKG SEQ ID NO: 17
52M51 Heavy chain CDR3
FDGNYGYYAMDY SEQ ID NO: 18
52M51 Light chain CDR1
RSSTGAVTTSNYAN SEQ ID NO: 19
52M51 Light chain CDR2
GTNNRAP SEQ ID NO: 20
52M51 Light chain CDR3
ALWYSNHWVFGGGTKL

Humanized 52M51 sequences:

SEQ ID NO: 21
52M51-H4 Heavy chain polynucleotide sequence
(Putative signal sequence underlined)
<u>ATGGATTGGACATGGAGGGTGTTCTGCCTCCTCGCTGTGGCTCCTGGAGTCCTGAGCCAG</u>
GTCCAGCTCGTCCAGAGCGGGGCTGAAGTCAAGAAGCCTGGCGCTAGCGTCAAAATCAGC
TGTAAGGTCAGCGGATACACACTGAGGGGATACTGGATCGAGTGGGTGAGGCAGGCTCCA
GGAAAGGGCCTGGAATGGATCGGCCAGATCCTGCCTGGAACCGGAAGGACAAATTACAAT
GAGAAGTTTAAGGGAAGGGTCACAATGACAGCAGACACAAGCACAGACAGCTTATATG
GAACTCAGCTCCCTCAGATCCGAGGACACCGCTGTCTACTATTGTGCCAGGTTCGATGGA
AATTACGGATACTATGCCATGGATTACTGGGGACAGGGGACAACGGTCACCGTGAGCTCA
GCCAGCACAAAGGGCCCCTAGCGTCTTCCCTCTGGCTCCCTGCAGCAGGAGCACCAGCGAG
AGCACAGCCGCCCTGGGCTGCCTGGTCAAGGACTACTTCCCCGAACCGGTGACGGTGTCG
TGGAACTCAGGCGCTCTGACCAGCGGCGTGCACACCTTCCCAGCTGTCCTACAGTCCTCA
GGACTCTACTCCCTCAGCAGCGTGGTGACCGTGCCCTCCAGCAACTTCGGCACCCAGACC
TACACCTGCAACGTAGATCACAAGCCCAGCAACACCAAGGTGGACAAGACAGTTGAGCGC
AAATGTTGTGTCGAGTGCCCACCGTGCCCAGCACCACCTGTGGCAGGACCGTCAGTCTTC
CTCTTCCCCCCAAAACCCAAGGACACCCTCATGATCTCCCGGACCCCTGAGGTCACGTGC
GTGGTGGTGGACGTGAGCCACGAAGACCCCGAGGTCCAGTTCAACTGGTACGTGGACGGC
GTGGAGGTGCATAATGCCAAGACAAAGCCACGGGAGGAGCAGTTCAACAGCACGTTCCGT
GTGGTCAGCGTCCTCACCGTTGTGCACCAGGACTGGCTGAACGGCAAGGAGTACAAGTGC
AAGGTCTCCAACAAAGGCCTCCCAGCCCCCATCGAGAAAACCATCTCCAAAACCAAAGGG
CAGCCCCGAGAACCACAGGTGTACACCCTGCCCCCATCCCGGGAGGAGATGACCAAGAAC
CAGGTCAGCCTGACCTGCCTGGTCAAAGGCTTCTACCCCAGCGACATCGCCGTGGAGTGG
GAGAGCAATGGGCAGCCGGAGAACAACTACAAGACCACACCTCCCATGCTGGACTCCGAC
GGCTCCTTCTTCCTCTACAGCAAGCTCACCGTGGACAAGAGCAGGTGGCAGCAGGGGAAC
GTCTTCTCATGCTCCGTGATGCATGAGGCTCTGCACAACCACTACACGCAGAAGAGCCTC
TCCCTGTCTCCGGGTAAATGA SEQ ID NO: 22
52M51 H4 Heavy chain amino acid sequence
(Putative signal sequence underlined)
<u>MDWTWRVFCLLAVAPGVLS</u>QVQLVQSGAEVKKPGASVKISCKVSGYTLRGYWIEWVRQAP
GKGLEWIGQILPGTGRTNYNEKFKGRVTMTADTSTDTAYMELSSLRSEDTAVYYCARFDG
NYGYYAMDYWGQGTTVTVSSASTKGPSVFPLAPCSRSTSESTAALGCLVKDYFPEPVTVS
WNSGALTSGVHTFPAVLQSSGLYSLSSVVTVPSSNFGTQTYTCNVDHKPSNTKVDKTVER
KCCVECPPCPAPPVAGPSVFLFPPKPKDTLMISRTPEVTCVVVDVSHEDPEVQFNWYVDG
VEVHNAKTKPREEQFNSTFRVVSVLTVVHQDWLNGKEYKCKVSNKGLPAPIEKTISKTKG
QPREPQVYTLPPSREEMTKNQVSLTCLVKGFYPSDIAVEWESNGQPENNYKTTPPMLDSD
GSFFLYSKLTVDKSRWQQGNVFSCSVMHEALHNHYTQKSLSLSPGK SEQ ID NO: 23
52M51-H4 Heavy chain variable region amino acid sequence
(Putative signal sequence underlined)
<u>MDWTWRVFCLLAVAPGVLS</u>QVQLVQSGAEVKKPGASVKISCKVSGYTLRGYWIEWVRQAP GKGLEWIGQILPGTGRTNYNEKFKGRVTMTADTSTDTAYMELSSLRSEDTAVYYCARFDG
NYGYYAMDYWGQGTTVTVSSA SEQ ID NO: 24
52M51-H4 Heavy chain variable region amino acid sequence
without putative signal sequence
QVQLVQSGAEVKKPGASVKISCKVSGYTLRGYWIEWVRQAPGKGLEWIGQILPGTGRTNY
NEKFKGRVTMTADTSTDTAYMELSSLRSEDTAVYYCARFDGNYGYYAMDYWGQGTTVTVS
SA SEQ ID NO: 25
52M51-L3 Light chain polynucleotide sequence
(Putative signal sequence is underlined)
ATGAGCGTCCCTACAATGGCTTGGATGATGCTCCTGCTGGGACTCCTGGCTTATGGAAGC
GGAGTGGATAGCCAGGCCGTCGTCACACAGGAACCTAGCCTCACCGTTAGCCCTGGAGGA
ACAGTCACACTGACCTGTAGGAGCTCCACAGGAGCTGTGACAACAAGCAATTACGCTAAC
TGGTTCCAGCAGAAGCCCGGTCAAGCCCCTAGAACCCTCATCGGCGGCACCAATAACAGA
GCTCCCGGAGTCCCCGCCAGGTTCTCCGGCTCCCTCCTGGGTGGCAAGGCTGCTCTGACA
CTCAGCGGTGCCCAGCCAGAGGATGAAGCGGAGTACTACTGTGCACTGTGGTACAGCAAC
CATTGGGTTTTCGGAGGCGGAACAAAGTTAACCGTCCTCGGGCAGCCTAAGGCTGCTCCT
AGCGTCACACTGTTCCCCCATCTAGCGAGGAGCTGCAGGCTAACAAGGCAACCCTCGTC
TGCCTGGTTAGCGACTTCTACCCTGGCGCTGTCACAGTGGCCTGGAAAGCTGACGGCTCC
CCTGTGAAAGTTGGCGTCGAAACCACAAAGCCTTCTAAGCAGAGCAATAATAAATATGCC
GCAAGCTCCTACCTCTCCCTGACTCCTGAGCAGTGGAAAAGCCATAGGAGCTACTCCTGC
CGGGTCACACACGAAGGAAGCACAGTGGAAAAGACAGTCGCCCCTGCTGAGTGTAGCTGA SEQ ID NO: 26
52M51-L3 Light chain amino acid sequence
(Putative signal sequence is underlined)
MSVPTMAWMMLLLGLLAYGSGVDSQAVVTQEPSLTVSPGGTVTLTCRSSTGAVTTSNYAN
WFQQKPGQAPRTLIGGTNNRAPGVPARFSGSLLGGKAALTLSGAQPEDEAEYYCALWYSN
HWVFGGGTKLTVLGQPKAAPSVTLFPPSSEELQANKATLVCLVSDFYPGAVTVAWKADGS
PVKVGVETTKPSKQSNNKYAASSYLSLTPEQWKSHRSYSCRVTHEGSTVEKTVAPAECS SEQ ID NO: 27
52M51-L3 Light chain variable region amino acid sequence
(Putative signal sequence is underlined)
MSVPTMAWMMLLLGLLAYGSGVDSQAVVTQEPSLTVSPGGTVTLTCRSSTGAVTTSNYAN
WFQQKPGQAPRTLIGGTNNRAPGVPARFSGSLLGGKAALTLSGAQPEDEAEYYCALWYSN
HWVFGGGTKLTVLG SEQ ID NO: 28
52M51-L3 Light chain variable region amino acid sequence
without putative signal sequence
SGVDSQAVVTQEPSLTVSPGGTVTLTCRSSTGAVTTSNYANWFQQKPGQAPRTLIGGTNN
RAPGVPARFSGSLLGGKAALTLSGAQPEDEAEYYCALWYSNHWVFGGGTKLTVLG SEQ ID NO: 29
52M51-L4 Light chain polynucleotide sequence
(Putative signal sequence is underlined)
ATGAGCGTCCCTACAATGGCTTGGATGATGCTCCTGCTGGGACTCCTGGCTTATGGAAGC
GGAGTGGATAGCCAGACCGTCGTCACACAGGAACCTAGCTTTTCCGTTAGCCCTGGAGGA
ACAGTCACACTGACCTGTAGGAGCTCCACAGGAGCTGTGACAACAAGCAATTACGCTAAC
TGGTATCAGCAGACTCCCGGTCAAGCCCCTAGAACCCTCATCGGCGGCACCAATAACAGA
GCTCCCGGAGTCCCCGACAGGTTCTCCGGCTCCATCCTGGGAAATAAAGCTGCTCTGACA
ATCACAGGTGCCCAGGCTGACGATGAAAGCGACTACTACTGTGCACTGTGGTACAGCAAC
CATTGGGTTTTCGGAGGCGGAACAAAGTTAACCGTCCTCGGGCAGCCTAAGGCTGCTCCT
AGCGTCACACTGTTCCCCCATCTAGCGAGGAGCTGCAGGCTAACAAGGCAACCCTCGTC
TGCCTGGTTAGCGACTTCTACCCTGGCGCTGTCACAGTGGCCTGGAAAGCTGACGGCTCC
CCTGTGAAAGTTGGCGTCGAAACCACAAAGCCTTCTAAGCAGAGCAATAATAAATATGCC
GCAAGCTCCTACCTCTCCCTGACTCCTGAGCAGTGGAAAAGCCATAGGAGCTACTCCTGC
CGGGTCACACACGAAGGAAGCACAGTGGAAAAGACAGTCGCCCCTGCTGAGTGTAGCTGA SEQ ID NO: 30
52M51-L4 Light chain amino acid sequence
(Putative signal sequence is underlined)
MSVPTMAWMMLLLGLLAYGSGVDSQTVVTQEPSFSVSPGGTVTLTCRSSTGAVTTSNYAN
WYQQTPGQAPRTLIGGTNNRAPGVPDRFSGSILGNKAALTITGAQADDESDYYCALWYSN
HWVFGGGTKLTVLGQPKAAPSVTLFPPSSEELQANKATLVCLVSDFYPGAVTVAWKADGS
PVKVGVETTKPSKQSNNKYAASSYLSLTPEQWKSHRSYSCRVTHEGSTVEKTVAPAECS SEQ ID NO: 31
52M51-L4 Light chain variable region amino acid sequence
(Putative signal sequence is underlined)
MSVPTMAWMMLLLGLLAYGSGVDSQTVVTQEPSFSVSPGGTVTLTCRSSTGAVTTSNYAN
WYQQTPGQAPRTLIGGTNNRAPGVPDRFSGSILGNKAALTITGAQADDESDYYCALWYSN
HWVFGGGTKLTVLG

SEQUENCES

SEQ ID NO: 32
52M51-L4 Light chain variable region amino acid sequence without putative signal sequence
SGVDSQTVVTQEPSFSVSPGGTVTLTCRSSTGAVTTSNYANWYQQTPGQAPRTLIGGTNN
RAPGVPDRFSGSILGNKAALTITGAQADDESDYYCALWYSNHWVFGGGTKLTVLG

---

What is claimed is:

1. An isolated antibody that specifically binds human Notch1, which comprises:
   (a) a heavy chain CDR1 comprising RGYWIE (SEQ ID NO:15); a heavy chain CDR2 comprising QILPGTGRTNYNEKFKG (SEQ ID NO:16); and a heavy chain CDR3 comprising FDGNYGYYAMDY (SEQ ID NO:17); and
   (b) a light chain CDR1 comprising RSSTGAVTTSNYAN (SEQ ID NO:18); a light chain CDR2 comprising GTNNRAP (SEQ ID NO:19); and a light chain CDR3 comprising ALWYSNHWVFGGGTKL (SEQ ID NO:20).

2. The antibody of claim 1, which binds to a non-ligand binding membrane proximal region of an extracellular domain of human Notch1 receptor.

3. The antibody of claim 2, wherein the non-ligand binding membrane proximal region of an extracellular domain of human Notch1 receptor comprises SEQ ID NO:2.

4. The isolated antibody of claim 1, wherein the antibody comprises:
   (a) a heavy chain variable region having at least 90% sequence identity to SEQ ID NO:14 or SEQ ID NO:24; and/or
   (b) a light chain variable region having at least 90% sequence identity to SEQ ID NO:8, SEQ ID NO:28, or SEQ ID NO:32.

5. The antibody of claim 1, which comprises:
   (a) a heavy chain variable region comprising SEQ ID NO:24; and
   (b) a light chain variable region comprising SEQ ID NO:28.

6. The antibody of claim 1, which is a recombinant antibody, a monoclonal antibody, a chimeric antibody, a humanized antibody, a human antibody, an antibody fragment, a bispecific antibody, a monospecific antibody, a monovalent antibody, an IgG1 antibody, or an IgG2 antibody.

7. A pharmaceutical composition comprising the antibody of claim 1.

8. A cell line producing the antibody of claim 1.

9. An isolated polynucleotide molecule comprising a polynucleotide that encodes the antibody of claim 1.

10. A method of inhibiting growth of a tumor or a tumor cell, comprising contacting the tumor or tumor cell with an effective amount of the antibody of claim 1.

11. The method of claim 10, wherein the tumor is selected from the group consisting of a breast tumor, colorectal tumor, hepatic tumor, renal tumor, lung tumor, pancreatic tumor, ovarian tumor, prostate tumor, and head and neck tumor.

12. A method of reducing tumorigenicity of a tumor in a subject, comprising administering to the subject a therapeutically effective amount of the antibody of claim 1, wherein the tumor comprises cancer stem cells and the frequency of the cancer stem cells in the tumor is reduced by administration of the antibody.

13. The antibody of claim 1, which comprises:
 (a) a heavy chain variable region comprising SEQ ID NO:24; and
 (b) a light chain variable region comprising SEQ ID NO:32.

14. The antibody of claim 1, which is a monoclonal antibody.

15. The antibody of claim 14, which is a humanized antibody.

16. The antibody of claim 1, which is 52M51H4L3.

17. An isolated monoclonal antibody comprising heavy and light chain variable regions identical in sequence to the heavy and light chain variable regions encoded by the plasmid on deposit as ATCC Patent Deposit Designation PTA-9549.

18. A method of treating cancer in a subject, comprising administering to the subject a therapeutically effective amount of an antibody that specifically binds human Notch1, wherein the antibody comprises:
 (a) a heavy chain CDR1 comprising RGYWIE (SEQ ID NO:15), a heavy chain CDR2 comprising QILPGTGRT-NYNEKFKG (SEQ ID NO:16), and a heavy chain CDR3 comprising FDGNYGYYAMDY (SEQ ID NO:17);
 (b) a light chain CDR1 comprising RSSTGAVTTSNYAN (SEQ ID NO:18), a light chain CDR2 comprising GTNNRAP (SEQ ID NO:19), and a light chain CDR3 comprising ALWYSNHWVFGGGTKL (SEQ ID NO:20).

19. The method of claim 18, wherein the cancer is selected from the group consisting of a breast cancer, colorectal cancer, hepatic cancer, kidney cancer, liver cancer, lung cancer, pancreatic cancer, gastrointestinal cancer, melanoma, ovarian cancer, prostate cancer, cervical cancer, bladder cancer, glioblastoma, and head and neck cancer.

20. The method of claim 18, further comprising administering to the subject at least one additional anti-cancer or therapeutic agent.

21. The method of claim 20, wherein the additional therapeutic agent is a chemotherapeutic agent.

22. The method of claim 18, wherein the antibody is 52M51H4L3.

* * * * *

SEQUENCE LISTING

<160> NUMBER OF SEQ ID NOS: 32

<210> SEQ ID NO 1
<211> LENGTH: 918
<212> TYPE: DNA
<213> ORGANISM: Homo sapiens

<400> SEQUENCE: 1

```
cacatcctgg actacagctt cggggtggg gccgggcgcg acatcccccc gccgctgatc      60
gaggaggcgt gcgagctgcc cgagtgccag gaggacgcgg caacaaggt ctgcagcctg      120
cagtgcaaca ccacgcgtg cggctgggac ggcggtgact gctccctcaa cttcaatgac      180
ccctggaaga actgcacgca gtctctgcag tgctggaagt acttcagtga cggccactgt      240
gacagccagt gcaactcagc cggctgcctc ttcgacggct tgactgcca gcgtgcggaa      300
ggccagtgca ccccctgta cgaccagtac tgcaaggacc acttcagcga cgggcactgc      360
gaccagggct gcaacagcgc ggagtgcgag tgggacgggc tggactgtgc ggagcatgta      420
cccgagaggc tggcggccgg cacgctggtg gtggtggtgc tgatgccgcc ggagcagctg      480
cgcaacagct ccttccactt cctgcgggag ctcagccgcg tgctgcacac caacgtggtc      540
ttcaagcgtg acgcacacgg ccagcagatg atcttcccct actacggccg cgaggaggag      600
ctgcgcaagc accccatcaa gcgtgccgcc gagggctggg ccgcacctga cgccctgctg      660
ggccaggtga aggcctcgct gctccctggt ggcagcgagg gtgggcggcg gcggagggag      720
ctggaccca tggacgtccg cggctccatc gtctacctgg agattgacaa ccggcagtgt      780
gtgcaggcct cctcgcagtg cttccagagt gccaccgacg tggccgcatt cctgggagcg      840
ctcgcctcgc tgggcagcct caacatcccc tacaagatcg aggccgtgca gagtgagacc      900
gtggagccgc ccccgccg                                                    918
```

<210> SEQ ID NO 2
<211> LENGTH: 306
<212> TYPE: PRT
<213> ORGANISM: Homo sapiens

<400> SEQUENCE: 2

```
His Ile Leu Asp Tyr Ser Phe Gly Gly Gly Ala Gly Arg Asp Ile Pro
1               5                   10                  15

Pro Pro Leu Ile Glu Glu Ala Cys Glu Leu Pro Glu Cys Gln Glu Asp
                20                  25                  30

Ala Gly Asn Lys Val Cys Ser Leu Gln Cys Asn Asn His Ala Cys Gly
            35                  40                  45

Trp Asp Gly Gly Asp Cys Ser Leu Asn Phe Asn Asp Pro Trp Lys Asn
        50                  55                  60

Cys Thr Gln Ser Leu Gln Cys Trp Lys Tyr Phe Ser Asp Gly His Cys
65                  70                  75                  80
```

```
Asp Ser Gln Cys Asn Ser Ala Gly Cys Leu Phe Asp Gly Phe Asp Cys
                 85                  90                  95
Gln Arg Ala Glu Gly Gln Cys Asn Pro Leu Tyr Asp Gln Tyr Cys Lys
            100                 105                 110
Asp His Phe Ser Asp Gly His Cys Asp Gln Gly Cys Asn Ser Ala Glu
        115                 120                 125
Cys Glu Trp Asp Gly Leu Asp Cys Ala Glu His Val Pro Glu Arg Leu
    130                 135                 140
Ala Ala Gly Thr Leu Val Val Val Leu Met Pro Pro Glu Gln Leu
145                 150                 155                 160
Arg Asn Ser Ser Phe His Phe Leu Arg Glu Leu Ser Arg Val Leu His
                165                 170                 175
Thr Asn Val Val Phe Lys Arg Asp Ala His Gly Gln Gln Met Ile Phe
            180                 185                 190
Pro Tyr Tyr Gly Arg Glu Glu Leu Arg Lys His Pro Ile Lys Arg
        195                 200                 205
Ala Ala Glu Gly Trp Ala Ala Pro Asp Ala Leu Leu Gly Gln Val Lys
    210                 215                 220
Ala Ser Leu Leu Pro Gly Gly Ser Glu Gly Gly Arg Arg Arg Arg Glu
225                 230                 235                 240
Leu Asp Pro Met Asp Val Arg Gly Ser Ile Val Tyr Leu Glu Ile Asp
                245                 250                 255
Asn Arg Gln Cys Val Gln Ala Ser Ser Gln Cys Phe Gln Ser Ala Thr
            260                 265                 270
Asp Val Ala Ala Phe Leu Gly Ala Leu Ala Ser Leu Gly Ser Leu Asn
        275                 280                 285
Ile Pro Tyr Lys Ile Glu Ala Val Gln Ser Glu Thr Val Glu Pro Pro
    290                 295                 300
Pro Pro
305

<210> SEQ ID NO 3
<211> LENGTH: 705
<212> TYPE: DNA
<213> ORGANISM: Artificial Sequence
<220> FEATURE:
<223> OTHER INFORMATION: Synthetic light chain of antibody 52M51

<400> SEQUENCE: 3
atggcctgga tttcacttat actctctctc ctggctctca gctcaggggc catttcccag      60
gctgttgtga ctcaggaatc tgcactcacc acatcacctg gtgaaacagt cacactcact     120
tgtcgctcaa gtactggggc tgttacaact agtaactacg ccaactgggt ccaagaaaaa     180
cctgatcatt tattcactgg tctaataggt ggtaccaaca accgagctcc aggtgttcct     240
gccagattct caggctccct gattggagac aaggctgccc tcaccatcac aggggcacag     300
actgaggatg aggcaatata tttctgtgct ctatggtaca gcaaccactg ggtgttcggt     360
ggaggaacca aactgactgt cctaggccag cccaagtctt cgccatcagt caccctgttt     420
ccaccttcct ctgaagagct cgagactaac aaggccacac tggtgtgtac gatcactgat     480
ttctacccag gtgtggtgac agtggactgg aaggtagatg gtacccctgt cactcagggt     540
atggagacaa cccagccttc caaacagagc aacaacaagt acatggctag cagctacctg     600
accctgacag caagagcatg ggaaaggcat agcagttaca gctgccaggt cactcatgaa     660
ggtcacactg tggagaagag tttgtcccgt gctgactgtt cctag                    705
```

<210> SEQ ID NO 4
<211> LENGTH: 234
<212> TYPE: PRT
<213> ORGANISM: Artificial Sequence
<220> FEATURE:
<223> OTHER INFORMATION: Synthetic light chain of antibody 52M51

<400> SEQUENCE: 4

```
Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125

Gly Gln Pro Lys Ser Ser Pro Ser Val Thr Leu Phe Pro Pro Ser Ser
    130                 135                 140

Glu Glu Leu Glu Thr Asn Lys Ala Thr Leu Val Cys Thr Ile Thr Asp
145                 150                 155                 160

Phe Tyr Pro Gly Val Val Thr Val Asp Trp Lys Val Asp Gly Thr Pro
                165                 170                 175

Val Thr Gln Gly Met Glu Thr Thr Gln Pro Ser Lys Gln Ser Asn Asn
            180                 185                 190

Lys Tyr Met Ala Ser Ser Tyr Leu Thr Leu Thr Ala Arg Ala Trp Glu
        195                 200                 205

Arg His Ser Ser Tyr Ser Cys Gln Val Thr His Glu Gly His Thr Val
    210                 215                 220

Glu Lys Ser Leu Ser Arg Ala Asp Cys Ser
225                 230
```

<210> SEQ ID NO 5
<211> LENGTH: 387
<212> TYPE: DNA
<213> ORGANISM: Artificial Sequence
<220> FEATURE:
<223> OTHER INFORMATION: Synthetic light chain of antibody 52M51

<400> SEQUENCE: 5

```
atggcctgga tttcacttat actctctctc ctggctctca gctcaggggc catttcccag      60
gctgttgtga ctcaggaatc tgcactcacc acatcacctg gtgaaacagt cacactcact     120
tgtcgctcaa gtactgggc tgttacaact agtaactacg ccaactgggt ccaagaaaaa     180
cctgatcatt tattcactgg tctaataggt ggtaccaaca accgagctcc aggtgttcct     240
gccagattct caggctccct gattggagac aaggctgccc tcaccatcac aggggcacag     300
actgaggatg aggcaatata tttctgtgct ctatggtaca gcaaccactg ggtgttcggt     360
ggaggaacca aactgactgt cctaggc                                         387
```

<210> SEQ ID NO 6
<211> LENGTH: 180
<212> TYPE: PRT
<213> ORGANISM: Artificial Sequence
<220> FEATURE:
<223> OTHER INFORMATION: Synthetic light chain of antibody 52M51

<400> SEQUENCE: 6

```
Met Ala Trp Ile Ser Leu Ile Leu Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Ser Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Asn Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asn His Trp Val Phe Gly Gly Gly Thr Lys Leu Thr Val Leu
        115                 120                 125

Gly Gln Pro Lys Ser Ser Pro Ser Val Thr Leu Phe Pro Pro Ser Ser
    130                 135                 140

Glu Glu Leu Glu Thr Asn Lys Ala Thr Leu Val Cys Thr Ile Thr Asp
145                 150                 155                 160

Phe Tyr Pro Gly Val Val Thr Val Asp Trp Lys Val Asp Gly Thr Pro
                165                 170                 175

Val Thr Gln Gly
            180
```

<210> SEQ ID NO 7
<211> LENGTH: 330
<212> TYPE: DNA
<213> ORGANISM: Artificial Sequence
<220> FEATURE:
<223> OTHER INFORMATION: Synthetic light chain of antibody 52M51

<400> SEQUENCE: 7

```
caggctgttg tgactcagga atctgcactc accacatcac ctggtgaaac agtcacactc      60
acttgtcgct caagtactgg ggctgttaca actagtaact acgccaactg ggtccaagaa     120
aaacctgatc atttattcac tggtctaata ggtggtacca acaaccgagc tccaggtgtt     180
cctgccagat tctcaggctc cctgattgga gacaaggctg ccctcaccat cacaggggca     240
cagactgagg atgaggcaat atatttctgt gctctatggt acagcaacca ctgggtgttc     300
ggtggaggaa ccaaactgac tgtcctaggc                                      330
```

<210> SEQ ID NO 8
<211> LENGTH: 110
<212> TYPE: PRT
<213> ORGANISM: Artificial Sequence
<220> FEATURE:
<223> OTHER INFORMATION: Synthetic light chain of antibody 52M51

<400> SEQUENCE: 8

Gln Ala Val Val Thr Gln Glu Ser Ala Leu Thr Thr Ser Pro Gly Glu

```
 1               5                   10                  15
Thr Val Thr Leu Thr Cys Arg Ser Ser Thr Gly Ala Val Thr Thr Ser
                20                  25                  30

Asn Tyr Ala Asn Trp Val Gln Glu Lys Pro Asp His Leu Phe Thr Gly
                35                  40                  45

Leu Ile Gly Gly Thr Asn Asn Arg Ala Pro Gly Val Pro Ala Arg Phe
        50                  55                  60

Ser Gly Ser Leu Ile Gly Asp Lys Ala Ala Leu Thr Ile Thr Gly Ala
 65                 70                  75                  80

Gln Thr Glu Asp Glu Ala Ile Tyr Phe Cys Ala Leu Trp Tyr Ser Asn
                    85                  90                  95

His Trp Val Phe Gly Gly Gly Thr Lys Leu Thr Val Leu Gly
                100                 105                 110
```

<210> SEQ ID NO 9
<211> LENGTH: 1395
<212> TYPE: DNA
<213> ORGANISM: Artificial Sequence
<220> FEATURE:
<223> OTHER INFORMATION: Synthetic heavy chain of antibody 52M51

<400> SEQUENCE: 9

```
atggaatgga cctgggtctt tctcttcctc ctgtcagtaa ctgcaggtgt ccactcccag      60
gttcagctgc agcagtctgg agctgagctg atgaagcctg gggcctcagt gaagatatcc     120
tgcaaggctg ctggctacac aatgagaggc tactggatag gtggataaa gcagaggcct      180
ggacatggcc ttgagtggat tggacagatt ttacctggaa ctgggagaac taactacaat     240
gagaagttca gggcaaggc cacattcact gcagatacat cctccaacac agccaacatg     300
caactcagca gcctgacatc tgaggactct gccgtctatt actgtgcaag atttgatggt     360
aactacggtt actatgctat ggactactgg ggtcaaggat cctcagtcac cgtctcctca     420
gccaaaacga cacccccatc tgtctatcca ctggcccctg gatctgctgc ccaaactaac     480
tccatggtga ccctgggatg cctggtcaag ggctatttcc ctgagccagt gacagtgacc     540
tggaactctg gatccctgtc cagcggtgtg cacaccttcc cagctgtcct gcagtctgac     600
ctctacactc tgagcagctc agtgactgtc ccctccagcc tcggcccag cgagaccgtc      660
acctgcaacg ttgcccaccc ggccagcagc accaaggtgg acaagaaaat tgtgcccagg     720
gattgtggtt gtaagccttg catatgtaca gtcccagaag tatcatctgt cttcatcttc     780
cccccaaagc ccaaggatgt cctcaccatt actctgactc ctaaggtcac gtgtgttgtg     840
gtagacatca gcaaggatga tcccgaggtc cagttcagct ggtttgtaga tgatgtggag     900
gtgcacacag ctcagacgca accccgggag gagcagttca acagcacttt ccgctcagtc     960
agtgaacttc ccatcatgca ccaggactgg ctcaatggca aggagttcaa atgcagggtc    1020
aacagtgcag ctttccctgc ccccatcgag aaaaccatat ccaaaaccaa aggcagaccg    1080
aaggctccac aggtgtacac cattccacct cccaaggagc agatggccaa ggataaagtc    1140
agtctgacct gcatgataac agacttcttc cctgaagaca taacagtgga gtggcagtgg    1200
aatgggcagc cagcggagaa ctacaagaac actcagccca tcatgaacac gaatggctct    1260
tacttcgtct acagcaagct caatgtgcag aagagcaact gggaggcagg aaatactttc    1320
acctgctctg tgttacatga gggcctgcac aaccaccata ctgagaagag cctctcccac    1380
tctcctggta aatga                                                     1395
```

<210> SEQ ID NO 10

```
<211> LENGTH: 464
<212> TYPE: PRT
<213> ORGANISM: Artificial Sequence
<220> FEATURE:
<223> OTHER INFORMATION: Synthetic heavy chain of antibody 52M51

<400> SEQUENCE: 10

Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Ala Gly Tyr Thr Met
        35                  40                  45

Arg Gly Tyr Trp Ile Glu Trp Ile Lys Gln Arg Pro Gly His Gly Leu
    50                  55                  60

Glu Trp Ile Gly Gln Ile Leu Pro Gly Thr Gly Arg Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Asn Met Gln Leu Ser Ser Leu Thr Ser Glu Asp Ser Ala Val
            100                 105                 110

Tyr Tyr Cys Ala Arg Phe Asp Gly Asn Tyr Gly Tyr Tyr Ala Met Asp
        115                 120                 125

Tyr Trp Gly Gln Gly Ser Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
                165                 170                 175

Val Thr Val Thr Trp Asn Ser Gly Ser Leu Ser Ser Gly Val His Thr
            180                 185                 190

Phe Pro Ala Val Leu Gln Ser Asp Leu Tyr Thr Leu Ser Ser Ser Val
        195                 200                 205

Thr Val Pro Ser Ser Pro Arg Pro Ser Glu Thr Val Thr Cys Asn Val
    210                 215                 220

Ala His Pro Ala Ser Ser Thr Lys Val Asp Lys Lys Ile Val Pro Arg
225                 230                 235                 240

Asp Cys Gly Cys Lys Pro Cys Ile Cys Thr Val Pro Glu Val Ser Ser
                245                 250                 255

Val Phe Ile Phe Pro Pro Lys Pro Lys Asp Val Leu Thr Ile Thr Leu
            260                 265                 270

Thr Pro Lys Val Thr Cys Val Val Val Asp Ile Ser Lys Asp Asp Pro
        275                 280                 285

Glu Val Gln Phe Ser Trp Phe Val Asp Asp Val Glu Val His Thr Ala
    290                 295                 300

Gln Thr Gln Pro Arg Glu Glu Gln Phe Asn Ser Thr Phe Arg Ser Val
305                 310                 315                 320

Ser Glu Leu Pro Ile Met His Gln Asp Trp Leu Asn Gly Lys Glu Phe
                325                 330                 335

Lys Cys Arg Val Asn Ser Ala Ala Phe Pro Ala Pro Ile Glu Lys Thr
            340                 345                 350

Ile Ser Lys Thr Lys Gly Arg Pro Lys Ala Pro Gln Val Tyr Thr Ile
        355                 360                 365

Pro Pro Pro Lys Glu Gln Met Ala Lys Asp Lys Val Ser Leu Thr Cys
    370                 375                 380
```

```
Met Ile Thr Asp Phe Phe Pro Glu Asp Ile Thr Val Glu Trp Gln Trp
385                 390                 395                 400

Asn Gly Gln Pro Ala Glu Asn Tyr Lys Asn Thr Gln Pro Ile Met Asn
            405                 410                 415

Thr Asn Gly Ser Tyr Phe Val Tyr Ser Lys Leu Asn Val Gln Lys Ser
        420                 425                 430

Asn Trp Glu Ala Gly Asn Thr Phe Thr Cys Ser Val Leu His Glu Gly
    435                 440                 445

Leu His Asn His His Thr Glu Lys Ser Leu Ser His Ser Pro Gly Lys
    450                 455                 460
```

<210> SEQ ID NO 11
<211> LENGTH: 420
<212> TYPE: DNA
<213> ORGANISM: Artificial Sequence
<220> FEATURE:
<223> OTHER INFORMATION: Synthetic heavy chain of antibody 52M51

<400> SEQUENCE: 11

```
atggaatgga cctgggtctt tctcttcctc ctgtcagtaa ctgcaggtgt ccactcccag    60
gttcagctgc agcagtctgg agctgagctg atgaagcctg gggcctcagt gaagatatcc   120
tgcaaggctg ctggctacac aatgagaggc tactggatag agtggataaa gcagaggcct   180
ggacatggcc ttgagtggat tggacagatt ttacctggaa ctgggagaac taactacaat   240
gagaagttca gggcaaggc cacattcact gcagatacat cctccaacac agccaacatg   300
caactcagca gcctgacatc tgaggactct gccgtctatt actgtgcaag atttgatggt   360
aactacggtt actatgctat ggactactgg ggtcaaggat cctcagtcac cgtctcctca   420
```

<210> SEQ ID NO 12
<211> LENGTH: 180
<212> TYPE: PRT
<213> ORGANISM: Artificial Sequence
<220> FEATURE:
<223> OTHER INFORMATION: Synthetic heavy chain of antibody 52M51

<400> SEQUENCE: 12

```
Met Glu Trp Thr Trp Val Phe Leu Phe Leu Leu Ser Val Thr Ala Gly
1               5                   10                  15

Val His Ser Gln Val Gln Leu Gln Gln Ser Gly Ala Glu Leu Met Lys
            20                  25                  30

Pro Gly Ala Ser Val Lys Ile Ser Cys Lys Ala Ala Gly Tyr Thr Met
        35                  40                  45

Arg Gly Tyr Trp Ile Glu Trp Ile Lys Gln Arg Pro Gly His Gly Leu
    50                  55                  60

Glu Trp Ile Gly Gln Ile Leu Pro Gly Thr Gly Arg Thr Asn Tyr Asn
65                  70                  75                  80

Glu Lys Phe Lys Gly Lys Ala Thr Phe Thr Ala Asp Thr Ser Ser Asn
                85                  90                  95

Thr Ala Asn Met Gln Leu Ser Ser Leu Thr Ser Glu Asp Ser Ala Val
            100                 105                 110

Tyr Tyr Cys Ala Arg Phe Asp Gly Asn Tyr Gly Tyr Tyr Ala Met Asp
        115                 120                 125

Tyr Trp Gly Gln Gly Ser Ser Val Thr Val Ser Ser Ala Lys Thr Thr
    130                 135                 140

Pro Pro Ser Val Tyr Pro Leu Ala Pro Gly Ser Ala Ala Gln Thr Asn
145                 150                 155                 160

Ser Met Val Thr Leu Gly Cys Leu Val Lys Gly Tyr Phe Pro Glu Pro
```

Val Thr Val Thr
        180

<210> SEQ ID NO 13
<211> LENGTH: 363
<212> TYPE: DNA
<213> ORGANISM: Artificial Sequence
<220> FEATURE:
<223> OTHER INFORMATION: Synthetic heavy chain of antibody 52M51

<400> SEQUENCE: 13
caggttcagc tgcagcagtc tggagctgag ctgatgaagc ctggggcctc agtgaagata    60
tcctgcaagg ctgctggcta cacaatgaga ggctactgga tagagtggat aaagcagagg    120
cctggacatg gccttgagtg gattggacag attttacctg gaactgggag aactaactac    180
aatgagaagt tcaagggcaa ggccacattc actgcagata catcctccaa cacagccaac    240
atgcaactca gcagcctgac atctgaggac tctgccgtct attactgtgc aagatttgat    300
ggtaactacg gttactatgc tatggactac tggggtcaag gatcctcagt caccgtctcc    360
tca                                                                  363

<210> SEQ ID NO 14
<211> LENGTH: 122
<212> TYPE: PRT
<213> ORGANISM: Artificial Sequence
<220> FEATURE:
<223> OTHER INFORMATION: Synthetic heavy chain of antibody 52M51

<400> SEQUENCE: 14

Gln Val Gln Leu Gln Gln Ser Gly Ala Glu Leu Met Lys Pro Gly Ala
1               5                   10                  15

Ser Val Lys Ile Ser Cys Lys Ala Ala Gly Tyr Thr Met Arg Gly Tyr
            20                  25                  30

Trp Ile Glu Trp Ile Lys Gln Arg Pro Gly His Gly Leu Glu Trp Ile
        35                  40                  45

Gly Gln Ile Leu Pro Gly Thr Gly Arg Thr Asn Tyr Asn Glu Lys Phe
    50                  55                  60

Lys Gly Lys Ala Thr Phe Thr Ala Asp Thr Ser Ser Asn Thr Ala Asn
65                  70                  75                  80

Met Gln Leu Ser Ser Leu Thr Ser Glu Asp Ser Ala Val Tyr Tyr Cys
                85                  90                  95

Ala Arg Phe Asp Gly Asn Tyr Gly Tyr Tyr Ala Met Asp Tyr Trp Gly
            100                 105                 110

Gln Gly Ser Ser Val Thr Val Ser Ser Ala
        115                 120

<210> SEQ ID NO 15
<211> LENGTH: 6
<212> TYPE: PRT
<213> ORGANISM: Artificial Sequence
<220> FEATURE:
<223> OTHER INFORMATION: Synthetic heavy chain CDR1 antibody

<400> SEQUENCE: 15

Arg Gly Tyr Trp Ile Glu
1               5

<210> SEQ ID NO 16
<211> LENGTH: 17
<212> TYPE: PRT

```
<213> ORGANISM: Artificial Sequence
<220> FEATURE:
<223> OTHER INFORMATION: Synthetic heavy chain CDR2 antibody

<400> SEQUENCE: 16

Gln Ile Leu Pro Gly Thr Gly Arg Thr Asn Tyr Asn Glu Lys Phe Lys
1               5                   10                  15

Gly

<210> SEQ ID NO 17
<211> LENGTH: 12
<212> TYPE: PRT
<213> ORGANISM: Artificial Sequence
<220> FEATURE:
<223> OTHER INFORMATION: Synthetic heavy chain CDR3 antibody

<400> SEQUENCE: 17

Phe Asp Gly Asn Tyr Gly Tyr Tyr Ala Met Asp Tyr
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic light chain CDR1 antibody

<400> SEQUENCE: 18

Arg Ser Ser Thr Gly Ala Val Thr Thr Ser Asn Tyr Ala Asn
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic light chain CDR2 antibody

<400> SEQUENCE: 19

Gly Thr Asn Asn Arg Ala Pro
1               5

<210> SEQ ID NO 20
<211> LENGTH: 16
<212> TYPE: PRT
<213> ORGANISM: Artificial Sequence
<220> FEATURE:
<223> OTHER INFORMATION: Synthetic light chain CDR3 antibody

<400> SEQUENCE: 20

Ala Leu Trp Tyr Ser Asn His Trp Val Phe Gly Gly Gly Thr Lys Leu
1               5                   10                  15

<210> SEQ ID NO 21
<211> LENGTH: 1401
<212> TYPE: DNA
<213> ORGANISM: Artificial Sequence
<220> FEATURE:
<223> OTHER INFORMATION: Synthetic heavy chain 52M51 antibody

<400> SEQUENCE: 21
atggattgga catggagggt gttctgcctc ctcgctgtgg ctcctggagt cctgagccag      60
gtccagctcg tccagagcgg ggctgaagtc aagaagcctg gcgctagcgt caaaatcagc     120
tgtaaggtca gcggatacac actgagggga tactggatcg agtgggtgag gcaggctcca     180
ggaaagggcc tggaatggat cggccagatc ctgcctggaa ccggaaggac aaattacaat     240
```

```
gagaagttta agggaagggt cacaatgaca gcagacacaa gcacagacac agcttatatg    300
gaactcagct ccctcagatc cgaggacacc gctgtctact attgtgccag gttcgatgga    360
aattacggat actatgccat ggattactgg ggacagggga caacggtcac cgtgagctca    420
gccagcacaa agggccctag cgtcttccct ctggctccct gcagcaggag caccagcgag    480
agcacagccg ccctgggctg cctggtcaag gactacttcc ccgaaccggt gacggtgtcg    540
tggaactcag gcgctctgac cagcggcgtg cacaccttcc cagctgtcct acagtcctca    600
ggactctact ccctcagcag cgtggtgacc gtgccctcca gcaacttcgg cacccagacc    660
tacacctgca acgtagatca caagcccagc aacaccaagg tggacaagac agttgagcgc    720
aaatgttgtg tcgagtgccc accgtgccca gcaccacctg tggcaggacc gtcagtcttc    780
ctcttccccc caaaacccaa ggacaccctc atgatctccc ggacccctga ggtcacgtgc    840
gtggtggtgg acgtgagcca cgaagacccc gaggtccagt tcaactggta cgtggacggc    900
gtggaggtgc ataatgccaa gacaaagcca cgggaggagc agttcaacag cacgttccgt    960
gtggtcagcg tcctcaccgt tgtgcaccag gactggctga acggcaagga gtacaagtgc   1020
aaggtctcca acaaaggcct cccagccccc atcgagaaaa ccatctccaa aaccaaaggg   1080
cagccccgag aaccacaggt gtacaccctg cccccatccc gggaggagat gaccaagaac   1140
caggtcagcc tgacctgcct ggtcaaaggc ttctacccca gcgacatcgc cgtggagtgg   1200
gagagcaatg ggcagccgga gaacaactac aagaccacac ctcccatgct ggactccgac   1260
ggctccttct tcctctacag caagctcacc gtggacaaga gcaggtggca gcagggaac    1320
gtcttctcat gctccgtgat gcatgaggct ctgcacaacc actacacgca gaagagcctc   1380
tccctgtctc cgggtaaatg a                                             1401

<210> SEQ ID NO 22
<211> LENGTH: 466
<212> TYPE: PRT
<213> ORGANISM: Artificial Sequence
<220> FEATURE:
<223> OTHER INFORMATION: Synthetic heavy chain 52M51 antibody

<400> SEQUENCE: 22

Met Asp Trp Thr Trp Arg Val Phe Cys Leu Leu Ala Val Ala Pro Gly
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Val Ser Gly Tyr Thr Leu
        35                  40                  45

Arg Gly Tyr Trp Ile Glu Trp Val Arg Gln Ala Pro Gly Lys Gly Leu
    50                  55                  60

Glu Trp Ile Gly Gln Ile Leu Pro Gly Thr Gly Arg Thr Asn Tyr Asn
65                  70                  75                  80

Glu Lys Phe Lys Gly Arg Val Thr Met Thr Ala Asp Thr Ser Thr Asp
                85                  90                  95

Thr Ala Tyr Met Glu Leu Ser Ser Leu Arg Ser Glu Asp Thr Ala Val
            100                 105                 110

Tyr Tyr Cys Ala Arg Phe Asp Gly Asn Tyr Gly Tyr Tyr Ala Met Asp
        115                 120                 125

Tyr Trp Gly Gln Gly Thr Thr Val Thr Val Ser Ser Ala Ser Thr Lys
    130                 135                 140

Gly Pro Ser Val Phe Pro Leu Ala Pro Cys Ser Arg Ser Thr Ser Glu
145                 150                 155                 160
```

```
Ser Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
    195                 200                 205

Val Thr Val Pro Ser Ser Asn Phe Gly Thr Gln Thr Tyr Thr Cys Asn
210                 215                 220

Val Asp His Lys Pro Ser Asn Thr Lys Val Asp Lys Thr Val Glu Arg
225                 230                 235                 240

Lys Cys Cys Val Glu Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys
465

<210> SEQ ID NO 23
<211> LENGTH: 141
<212> TYPE: PRT
<213> ORGANISM: Artificial Sequence
<220> FEATURE:
<223> OTHER INFORMATION: Synthetic heavy chain 52M51 antibody

<400> SEQUENCE: 23

Met Asp Trp Thr Trp Arg Val Phe Cys Leu Leu Ala Val Ala Pro Gly
1               5                   10                  15

Val Leu Ser Gln Val Gln Leu Val Gln Ser Gly Ala Glu Val Lys Lys
            20                  25                  30

Pro Gly Ala Ser Val Lys Ile Ser Cys Lys Val Ser Gly Tyr Thr Leu
        35                  40                  45
```

Arg Gly Tyr Trp Ile Glu Trp Val Arg Gln Ala Pro Gly Lys Gly Leu
            50                  55                  60

Glu Trp Ile Gly Gln Ile Leu Pro Gly Thr Gly Arg Thr Asn Tyr Asn
 65                  70                  75                  80

Glu Lys Phe Lys Gly Arg Val Thr Met Thr Ala Asp Thr Ser Thr Asp
                 85                  90                  95

Thr Ala Tyr Met Glu Leu Ser Ser Leu Arg Ser Glu Asp Thr Ala Val
            100                 105                 110

Tyr Tyr Cys Ala Arg Phe Asp Gly Asn Tyr Gly Tyr Tyr Ala Met Asp
            115                 120                 125

Tyr Trp Gly Gln Gly Thr Thr Val Thr Val Ser Ser Ala
            130                 135                 140

<210> SEQ ID NO 24
<211> LENGTH: 122
<212> TYPE: PRT
<213> ORGANISM: Artificial Sequence
<220> FEATURE:
<223> OTHER INFORMATION: Synthetic heavy chain 52M51 antibody

<400> SEQUENCE: 24

Gln Val Gln Leu Val Gln Ser Gly Ala Glu Val Lys Lys Pro Gly Ala
 1               5                  10                  15

Ser Val Lys Ile Ser Cys Lys Val Ser Gly Tyr Thr Leu Arg Gly Tyr
             20                  25                  30

Trp Ile Glu Trp Val Arg Gln Ala Pro Gly Lys Gly Leu Glu Trp Ile
         35                  40                  45

Gly Gln Ile Leu Pro Gly Thr Gly Arg Thr Asn Tyr Asn Glu Lys Phe
     50                  55                  60

Lys Gly Arg Val Thr Met Thr Ala Asp Thr Ser Thr Asp Thr Ala Tyr
 65                  70                  75                  80

Met Glu Leu Ser Ser Leu Arg Ser Glu Asp Thr Ala Val Tyr Tyr Cys
                 85                  90                  95

Ala Arg Phe Asp Gly Asn Tyr Gly Tyr Tyr Ala Met Asp Tyr Trp Gly
            100                 105                 110

Gln Gly Thr Thr Val Thr Val Ser Ser Ala
            115                 120

<210> SEQ ID NO 25
<211> LENGTH: 720
<212> TYPE: DNA
<213> ORGANISM: Artificial Sequence
<220> FEATURE:
<223> OTHER INFORMATION: Synthetic light chain 52M51 antibody

<400> SEQUENCE: 25
atgagcgtcc ctacaatggc ttggatgatg ctcctgctgg gactcctggc ttatggaagc      60
ggagtggata gccaggccgt cgtcacacag aacctagcc tcaccgttag ccctggagga     120
acagtcacac tgacctgtag gagctccaca ggagctgtga acaacaagcaa ttacgctaac    180 tggttccagc agaagcccgg tcaagcccct agaacccctca tcggcggcac caataacaga   240
gctcccggag tccccgccag gttctccggc tccctcctgg gtggcaaggc tgctctgaca    300
ctcagcggtg cccagccaga ggatgaagcg agtactact gtgcactgtg gtacagcaac    360
cattgggttt tcggaggcgg aacaaagtta accgtcctcg gcagcctaa ggctgctcct     420 agcgtcacac tgttcccccc atctagcgag gagctgcagg ctaacaaggc aaccctcgtc    480
tgcctggtta gcgacttcta ccctggcgct gtcacagtgg cctggaaagc tgacggctcc    540

```
cctgtgaaag ttggcgtcga aaccacaaag ccttctaagc agagcaataa taaatatgcc    600
gcaagctcct acctctccct gactcctgag cagtggaaaa gccataggag ctactcctgc    660
cgggtcacac acgaaggaag cacagtggaa aagacagtcg cccctgctga gtgtagctga    720
```

<210> SEQ ID NO 26
<211> LENGTH: 239
<212> TYPE: PRT
<213> ORGANISM: Artificial Sequence
<220> FEATURE:
<223> OTHER INFORMATION: Synthetic light chain 52M51 antibody

<400> SEQUENCE: 26

```
Met Ser Val Pro Thr Met Ala Trp Met Met Leu Leu Leu Gly Leu Leu
1               5                   10                  15

Ala Tyr Gly Ser Gly Val Asp Ser Gln Ala Val Val Thr Gln Glu Pro
            20                  25                  30

Ser Leu Thr Val Ser Pro Gly Gly Thr Val Thr Leu Thr Cys Arg Ser
        35                  40                  45

Ser Thr Gly Ala Val Thr Thr Ser Asn Tyr Ala Asn Trp Phe Gln Gln
    50                  55                  60

Lys Pro Gly Gln Ala Pro Arg Thr Leu Ile Gly Gly Thr Asn Asn Arg
65                  70                  75                  80

Ala Pro Gly Val Pro Ala Arg Phe Ser Gly Ser Leu Leu Gly Gly Lys
                85                  90                  95

Ala Ala Leu Thr Leu Ser Gly Ala Gln Pro Glu Asp Glu Ala Glu Tyr
            100                 105                 110

Tyr Cys Ala Leu Trp Tyr Ser Asn His Trp Val Phe Gly Gly Gly Thr
        115                 120                 125

Lys Leu Thr Val Leu Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Val Ser Asp Phe Tyr Pro Gly Ala Val Thr Val Ala Trp Lys
                165                 170                 175

Ala Asp Gly Ser Pro Val Lys Val Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Arg Val Thr His
    210                 215                 220

Glu Gly Ser Thr Val Glu Lys Thr Val Ala Pro Ala Glu Cys Ser
225                 230                 235
```

<210> SEQ ID NO 27
<211> LENGTH: 134
<212> TYPE: PRT
<213> ORGANISM: Artificial Sequence
<220> FEATURE:
<223> OTHER INFORMATION: Synthetic light chain 52M51 antibody

<400> SEQUENCE: 27

```
Met Ser Val Pro Thr Met Ala Trp Met Met Leu Leu Leu Gly Leu Leu
1               5                   10                  15

Ala Tyr Gly Ser Gly Val Asp Ser Gln Ala Val Val Thr Gln Glu Pro
            20                  25                  30

Ser Leu Thr Val Ser Pro Gly Gly Thr Val Thr Leu Thr Cys Arg Ser
        35                  40                  45
```

```
Ser Thr Gly Ala Val Thr Thr Ser Asn Tyr Ala Asn Trp Phe Gln Gln
 50                  55                  60

Lys Pro Gly Gln Ala Pro Arg Thr Leu Ile Gly Gly Thr Asn Asn Arg
 65                  70                  75                  80

Ala Pro Gly Val Pro Ala Arg Phe Ser Gly Ser Leu Leu Gly Gly Lys
                 85                  90                  95

Ala Ala Leu Thr Leu Ser Gly Ala Gln Pro Glu Asp Glu Ala Glu Tyr
            100                 105                 110

Tyr Cys Ala Leu Trp Tyr Ser Asn His Trp Val Phe Gly Gly Gly Thr
            115                 120                 125

Lys Leu Thr Val Leu Gly
            130

<210> SEQ ID NO 28
<211> LENGTH: 115
<212> TYPE: PRT
<213> ORGANISM: Artificial Sequence
<220> FEATURE:
<223> OTHER INFORMATION: Synthetic light chain 52M51 antibody

<400> SEQUENCE: 28

Ser Gly Val Asp Ser Gln Ala Val Val Thr Gln Glu Pro Ser Leu Thr
 1               5                  10                  15

Val Ser Pro Gly Gly Thr Val Thr Leu Thr Cys Arg Ser Ser Thr Gly
             20                  25                  30

Ala Val Thr Thr Ser Asn Tyr Ala Asn Trp Phe Gln Gln Lys Pro Gly
         35                  40                  45

Gln Ala Pro Arg Thr Leu Ile Gly Gly Thr Asn Asn Arg Ala Pro Gly
 50                  55                  60

Val Pro Ala Arg Phe Ser Gly Ser Leu Leu Gly Gly Lys Ala Ala Leu
 65                  70                  75                  80

Thr Leu Ser Gly Ala Gln Pro Glu Asp Glu Ala Glu Tyr Tyr Cys Ala
             85                  90                  95

Leu Trp Tyr Ser Asn His Trp Val Phe Gly Gly Gly Thr Lys Leu Thr
            100                 105                 110

Val Leu Gly
       115

<210> SEQ ID NO 29
<211> LENGTH: 720
<212> TYPE: DNA
<213> ORGANISM: Artificial Sequence
<220> FEATURE:
<223> OTHER INFORMATION: Synthetic light chain 52M51 antibody

<400> SEQUENCE: 29
atgagcgtcc ctacaatggc ttggatgatg ctcctgctgg gactcctggc ttatggaagc      60
ggagtggata gccagaccgt cgtcacacag gaacctagct tttccgttag ccctggagga     120
acagtcacac tgacctgtag gagctccaca ggagctgtga acaacaagca ttacgctaac     180
tggtatcagc agactcccgg tcaagcccct agaacccctc tcggcggcac caataacaga     240
gctcccggag tccccgacag gttctccggc tccatcctgg gaaataaagc tgctctgaca     300
atcacaggtg cccaggctga cgatgaaagc gactactact gtgcactgtg gtacagcaac     360
cattgggttt tcggaggcgg aacaaagtta accgtcctcg gcagcctaa ggctgctcct      420 agcgtcacac tgttccccccc atctagcgag gagctgcagg ctaacaaggc aaccctcgtc     480
tgcctggtta gcgacttcta ccctggcgct gtcacagtgg cctggaaagc tgacggctcc     540
```

```
cctgtgaaag ttggcgtcga aaccacaaag ccttctaagc agagcaataa taaatatgcc    600
gcaagctcct acctctccct gactcctgag cagtggaaaa gccataggag ctactcctgc    660
cgggtcacac acgaaggaag cacagtggaa aagacagtcg cccctgctga gtgtagctga    720
```

<210> SEQ ID NO 30
<211> LENGTH: 239
<212> TYPE: PRT
<213> ORGANISM: Artificial Sequence
<220> FEATURE:
<223> OTHER INFORMATION: Synthetic light chain 52M51 antibody

<400> SEQUENCE: 30

Met Ser Val Pro Thr Met Ala Trp Met Met Leu Leu Leu Gly Leu Leu
1               5                   10                  15

Ala Tyr Gly Ser Gly Val Asp Ser Gln Thr Val Val Thr Gln Glu Pro
            20                  25                  30

Ser Phe Ser Val Ser Pro Gly Gly Thr Val Thr Leu Thr Cys Arg Ser
        35                  40                  45

Ser Thr Gly Ala Val Thr Thr Ser Asn Tyr Ala Asn Trp Tyr Gln Gln
    50                  55                  60

Thr Pro Gly Gln Ala Pro Arg Thr Leu Ile Gly Gly Thr Asn Asn Arg
65                  70                  75                  80

Ala Pro Gly Val Pro Asp Arg Phe Ser Gly Ser Ile Leu Gly Asn Lys
                85                  90                  95

Ala Ala Leu Thr Ile Thr Gly Ala Gln Ala Asp Asp Glu Ser Asp Tyr
            100                 105                 110

Tyr Cys Ala Leu Trp Tyr Ser Asn His Trp Val Phe Gly Gly Gly Thr
        115                 120                 125

Lys Leu Thr Val Leu Gly Gln Pro Lys Ala Ala Pro Ser Val Thr Leu
    130                 135                 140

Phe Pro Pro Ser Ser Glu Glu Leu Gln Ala Asn Lys Ala Thr Leu Val
145                 150                 155                 160

Cys Leu Val Ser Asp Phe Tyr Pro Gly Ala Val Thr Val Ala Trp Lys
                165                 170                 175

Ala Asp Gly Ser Pro Val Lys Val Gly Val Glu Thr Thr Lys Pro Ser
            180                 185                 190

Lys Gln Ser Asn Asn Lys Tyr Ala Ala Ser Ser Tyr Leu Ser Leu Thr
        195                 200                 205

Pro Glu Gln Trp Lys Ser His Arg Ser Tyr Ser Cys Arg Val Thr His
    210                 215                 220

Glu Gly Ser Thr Val Glu Lys Thr Val Ala Pro Ala Glu Cys Ser
225                 230                 235

<210> SEQ ID NO 31
<211> LENGTH: 134
<212> TYPE: PRT
<213> ORGANISM: Artificial Sequence
<220> FEATURE:
<223> OTHER INFORMATION: Synthetic light chain 52M51 antibody

<400> SEQUENCE: 31

Met Ser Val Pro Thr Met Ala Trp Met Met Leu Leu Leu Gly Leu Leu
1               5                   10                  15

Ala Tyr Gly Ser Gly Val Asp Ser Gln Thr Val Val Thr Gln Glu Pro
            20                  25                  30

Ser Phe Ser Val Ser Pro Gly Gly Thr Val Thr Leu Thr Cys Arg Ser
        35                  40                  45

```
Ser Thr Gly Ala Val Thr Thr Ser Asn Tyr Ala Asn Trp Tyr Gln Gln
 50                  55                  60

Thr Pro Gly Gln Ala Pro Arg Thr Leu Ile Gly Gly Thr Asn Asn Arg
 65                  70                  75                  80

Ala Pro Gly Val Pro Asp Arg Phe Ser Gly Ser Ile Leu Gly Asn Lys
                 85                  90                  95

Ala Ala Leu Thr Ile Thr Gly Ala Gln Ala Asp Asp Glu Ser Asp Tyr
                100                 105                 110

Tyr Cys Ala Leu Trp Tyr Ser Asn His Trp Val Phe Gly Gly Thr
            115                 120                 125

Lys Leu Thr Val Leu Gly
            130

<210> SEQ ID NO 32
<211> LENGTH: 115
<212> TYPE: PRT
<213> ORGANISM: Artificial Sequence
<220> FEATURE:
<223> OTHER INFORMATION: Synthetic light chain 52M51 antibody

<400> SEQUENCE: 32

Ser Gly Val Asp Ser Gln Thr Val Val Thr Gln Glu Pro Ser Phe Ser
 1               5                  10                  15

Val Ser Pro Gly Gly Thr Val Thr Leu Thr Cys Arg Ser Ser Thr Gly
                 20                  25                  30

Ala Val Thr Thr Ser Asn Tyr Ala Asn Trp Tyr Gln Gln Thr Pro Gly
             35                  40                  45

Gln Ala Pro Arg Thr Leu Ile Gly Gly Thr Asn Asn Arg Ala Pro Gly
 50                  55                  60

Val Pro Asp Arg Phe Ser Gly Ser Ile Leu Gly Asn Lys Ala Ala Leu
 65                  70                  75                  80

Thr Ile Thr Gly Ala Gln Ala Asp Asp Glu Ser Asp Tyr Tyr Cys Ala
                 85                  90                  95

Leu Trp Tyr Ser Asn His Trp Val Phe Gly Gly Gly Thr Lys Leu Thr
            100                 105                 110

Val Leu Gly
        115
```